US012741983B2

(12) United States Patent
Yoshikawa et al.

(10) Patent No.: US 12,741,983 B2
(45) Date of Patent: Sep. 22, 2026

(54) ARTIFICIAL NUCLEIC ACID, METHOD FOR PRODUCING SAME, AND USE THEREOF

(71) Applicant: RIKEN GENESIS CO., LTD., Tokyo (JP)

(72) Inventors: Haruhisa Yoshikawa, Tokyo (JP); Ikuya Ban, Tokyo (JP); Takeshi Imanishi, Tokyo (JP)

(73) Assignee: RIKEN GENESIS CO., LTD., Tokyo (JP)

( * ) Notice: Subject to any disclaimer, the term of this patent is extended or adjusted under 35 U.S.C. 154(b) by 631 days.

(21) Appl. No.: 18/189,914

(22) Filed: Mar. 24, 2023

(65) Prior Publication Data

US 2023/0257413 A1 Aug. 17, 2023

Related U.S. Application Data

(63) Continuation of application No. PCT/JP2021/035003, filed on Sep. 24, 2021.

(30) Foreign Application Priority Data

Sep. 25, 2020 (JP) ................................ 2020-161113

(51) Int. Cl.
*C07H 19/10* (2006.01)
*C07H 19/207* (2006.01)

(52) U.S. Cl.
CPC .......... *C07H 19/10* (2013.01); *C07H 19/207* (2013.01)

(58) Field of Classification Search
None
See application file for complete search history.

(56) References Cited

U.S. PATENT DOCUMENTS

2003/0105309 A1 6/2003 Imanishi et al.
2003/0207841 A1 11/2003 Kaneko et al.
2007/0167387 A1 7/2007 Imanishi et al.
2018/0223281 A1 8/2018 Iba et al.
2022/0089634 A1 3/2022 Ban et al.

FOREIGN PATENT DOCUMENTS

WO 2005/021570 A1 3/2005
WO 2010/021344 A1 2/2010
WO 2011/085102 A1 7/2011
WO 2017/047097 A1 3/2017
WO 2019/122277 A1 6/2019
WO 2020/203896 A1 10/2020

OTHER PUBLICATIONS

Surender Kumar, et al., "Synthesis of Functionalized Carbocyclic Locked Nucleic Acid Analogues by Ring-Closing Diene and Enyne Metathesis and Their Influence on Nucleic Acid Stability and Structure", The Journal of Organic Chemistry, 2009, vol. 74, No. 17, pp. 6756-6769.
Yuta Ito, et al., "Synthesis of the Methyl Analog of 2'-O, 4'-C-Ethylene-Bridged 5-Methyluridine via Intramolecular Radical Cyclization and Properties of Modified Oligonucleotides", The Journal of Organic Chemistry, 2019, vol. 84, No. 14, pp. 9093-9100.
Chuanzheng Zhou, et al., "Fine Tuning of Electrostatics around the Internucleotidic Phosphate through Incorporation of Modified 2',4'-Carbocyclic-LNAs and -ENAs Leads to Significant Modulation of Antisense Properties", The Journal of Organic Chemistry, 2009, vol. 74, No. 1, pp. 118-134.
Hideto Miyabe, et al., "Highly Diastereoselective Radical Addition to Oxime Ethers: Asymmetric Synthesis of β-Amino Acids", Organic Letters, 1999, vol. 1, No. 4, pp. 569-572.
J. Alberto Marco, et al., "Diastereoselective Additions of Organolithium and Organomagnesium Reagents to the C=N Bond of A Chiral, Cyclic Nitrone Derived from Erythrulose", Tetrahedron Letters, 1998, vol. 39, pp. 3237-3240.
International Search Report for PCT/JP2021/035003 dated Nov. 22, 2021 [PCT/ISA/210].

*Primary Examiner* — Patrick T Lewis
(74) *Attorney, Agent, or Firm* — Sughrue Mion, PLLC

(57) ABSTRACT

Disclosed is a compound represented by formula (1) or a salt thereof wherein: "Base" represents an aromatic heterocyclic group which may have a substituent, or an aromatic hydrocarbon ring group which may have a substituent; $A^1$ represents a single bond or an alkylene group; $R^1$ to $R^5$ represent an atom or a group disclosed in the specification.

19 Claims, 4 Drawing Sheets

Specification includes a Sequence Listing.

DNA OLIGONUCLEOTIDE
S OLIGONUCLEOTIDE
NH−T OLIGONUCLEOTIDE
NMe−T OLIGONUCLEOTIDE
LNA−T OLIGONUCLEOTIDE
(R)M−T OLIGONUCLEOTIDE
(R)E−T OLIGONUCLEOTIDE

ARTIFICIAL NUCLEIC ACID, METHOD FOR PRODUCING SAME, AND USE THEREOF

CROSS REFERENCE TO RELATED APPLICATIONS AND INCORPORATION BY REFERENCE OF SEQUENCE LISTING

This application claims priority from prior Japanese Patent Application No. 2020-16113, filed on Sep. 25, 2020, entitled "NOVEL ARTIFICIAL NUCLEIC ACID, METHOD FOR PRODUCING SAME, AND USE OF SAME", the entire contents of which are incorporated herein by reference. The content of the electronically submitted sequence listing, file name: Q284268_sequence listing as filed.XML; size: 7,041 bytes; and date of creation: Mar. 24, 2023, filed herewith, is incorporated herein by reference in its entirety.

FIELD OF THE INVENTION

The present invention relates to a novel artificial nucleic acid, a method for producing the artificial nucleic acid, a use of the artificial nucleic acid, and others.

BACKGROUND

An oligonucleotide is a short sequence of naturally occurring DNA, naturally occurring RNA or an artificial nucleic acid. It has been shown that an oligonucleotide can regulate the expression of a gene at various gene transcription or translation levels and can examine the state of the sequence for a gene and is therefore very useful for the treatment or diagnosis of a specific disease.

The technique for the regulation of the expression of a gene and the examination/diagnosis of genetic information is roughly classified into two types depending on the types of targets. The first case is a case where a target is single-stranded RNA or single-stranded DNA such as messenger RNA (mRNA) or micro RNA (miRNA), and the second case is a case where the target is double-stranded genomic DNA.

When the target is single-stranded RNA or single-stranded DNA, the process of the translation of a gene can be inhibited (or the genetic diagnosis can be performed) by an antisense method in which an oligonucleotide binds to the single-stranded RNA or the single-stranded DNA complementary to form a double strand. When the oligonucleotide is a double-stranded RNA molecule, the complementary binding of the oligonucleotide to target mRNA can cause the decomposition of the target mRNA with a "slicer" enzyme in an RISC complex (RNA interference method). In the case of RNA interference method, the oligonucleotide may be an oligonucleotide which is equivalent to endogenous microRNA that can bind to a 3'-UTR region (a 3'-untranslated region) in target mRNA and can inhibit the translation of the target mRNA as the result of the incomplete complementary (microRNA mimics).

An oligonucleotide can induce the activation of a gene or the increase in transcription of the gene through, for example, the complementary binding of the oligonucleotide to long antisense non-coding RNA or the inhibition of complementary microRNA by the oligonucleotide, and, as a result, can increase the translation of target mRNA in the microRNA (anti microRNA).

An oligonucleotide which can be used as a functional material for use in a technique for regulating gene expression or examining/diagnosing genetic information has been required to have properties such as excellent sequence-specific binding affinity for a target nucleic acid, high resistance to degradation enzymes and safety in living bodies. DNA and RNA which are naturally occurring materials have poor resistance to degradation enzymes and insufficient binding affinity, and are therefore unsuitable as functional materials. For these reasons, numerous artificial nucleic acids have been developed so far for the purpose of improving the functionalities of oligonucleotides.

Typical examples of the artificial nucleic acid include a peptide nucleic acid (PNA), a crosslinked nucleic acid, a morpholino nucleic acid (PMO), and a phosophorothioate-type nucleic acid (S oligonucleotide) which has such a structure that one of non-binding oxygen atoms in a phosphoric acid diester moiety in a nucleic acid is substituted by a sulfur atom. Typical examples of the crosslinked nucleic acid include LNA (Structural formula 1), $BNA^{NC}$ (Structural formula 2) and ENA (Structural formula 3).

[Formula 1]

Structural formula 1

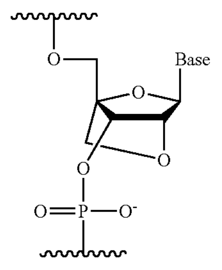

Structural formula 2

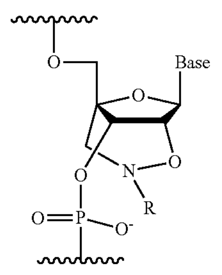

R = H, alkyl, aryl, acyl, sulfonyl

Structural formula 3

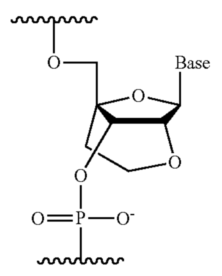

The structure of the phosophorothioate-type nucleic acid is represented by structural formula 4.

[Formula 2]

Structural formula 4

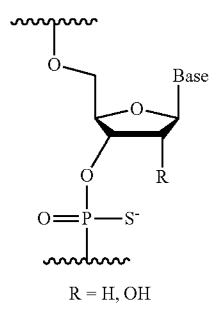

R = H, OH

It has been demonstrated that these crosslinked nucleic acids have excellent capability of binding to single-stranded RNA with high sequence selectivity through Watson-Crick-type hydrogen bonds (US Patent Application Publication No. 2003/105309, US Patent Application Publication No. 2007/167387, and US Patent Application Publication No. 2003/207841). As mentioned above, the conventional artificial nucleic acids have been used as functional materials for regulating the expression of a specific gene or for confirming/diagnosing the genetic sequence for the gene with high sensitivity and high accuracy.

However, amid the diversification in use applications of oligonucleotides, there is still a room for improving the functionalities of the already developed artificial nucleic acids and it has been demanded to develop a novel artificial nucleic acid aiming at the further improvement in the functionality of the artificial nucleic acid.

The object of the present invention is to provide a novel artificial nucleic acid which is useful in various genome technologies, a method for producing the artificial nucleic acid, a use of the artificial nucleic acid, and others.

SUMMARY OF THE INVENTION

The scope of the present invention is defined solely by the appended claims, and is not affected to any degree by the statements within this summary.

The present inventors have studied intensively and extensively in order to achieve the above-mentioned object. As a result, it has been found that an artificial nucleic acid having such a structure that an alkyl group optionally having a substituent or an aryl group optionally having a substituent is bound onto a carbon atom located between a carbon atom at position-4 in a furanose and a nitrogen atom to which R is bound in $BNA^{Nc}$ represented by structural formula 2 has both of highly sequence-selective and stiff capability of binding to single-stranded DNA and single-stranded RNA and excellent resistance capability against digestive enzymes. The present inventors have further made studies on the basis of these findings. As a result, the present invention has been accomplished.

The present invention includes the following aspects.

Item 1.

A compound represented by formula (1) or a salt thereof:

[Formula 3]

(1)

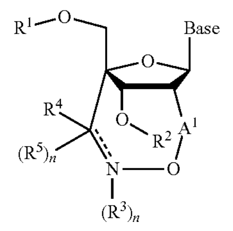

[wherein:

"Base" represents an aromatic heterocyclic group which may have a substituent, or an aromatic hydrocarbon ring group which may have a substituent;

$A^1$ represents a single bond or an alkylene group;

$R^1$ and $R^2$ are the same as or different from each other and independently represent a hydrogen atom, an alkyl group which may have a substituent, an alkenyl group which may have a substituent, a cycloalkyl group which may have a substituent, a cycloalkenyl group which may have a substituent, an aryl group which may have a substituent, a protecting group for a hydroxyl group, a phosphino group which has a substituent, a dihydroxyphosphinyl group which may have a substituent, or a hydroxymercaptophosphinyl group which may have a substituent, or $R^1$, $R^2$, two oxygen atoms respectively adjacent to $R^1$ and $R^2$ and carbon atoms at position-3 to position-5 in a furanose together form a ring which may have a substituent;

$R^3$ represents a hydrogen atom, an alkyl group which may have a substituent, an alkenyl group which may have a substituent, a cycloalkyl group which may have a substituent, an aryl group which may have a substituent, an acyl group which may have a substituent, a sulfonyl group which has a substituent, a silyl group which has a substituent, a functional molecule unit substituent, or a group represented by the formula: $R^{31}$—X— (wherein $R^{31}$ represents an amino group which may have a substituent; and X represents an alkylene group which may have a substituent, or a group having such a structure that at least one methylene group moiety in the alkylene group is substituted by —N($R^{32}$)— (wherein $R^{32}$ represents a hydrogen atom or an alkyl group), —O— or —S(=O)$_k$— (wherein k represents 0, 1 or 2));

$R^4$ represents a hydrogen atom, an alkyl group which may have a substituent, or an aryl group which may have a substituent;

$R^5$ represents a hydrogen atom, an alkyl group which may have a substituent, or an aryl group which may have a substituent;

$R^4$ and $R^5$ do not represent hydrogen atoms coincidentally;

a symbol represented by the following formula:

[Formula 4]

represents a single bond or a double bond;

when the symbol represents a single bond, n represents 1; and when the symbol represents a double bond, n represents 0].

Item 2.

The compound or the salt thereof according to item 1, wherein A' represents a single bond.

Item 3.

The compound or the salt thereof according to item 1 or 2, wherein the symbol represented by the following formula:

[Formula 5]

represents a single bond and n represents 1.

Item 4.

The compound or the salt thereof according to any one of items 1 to 3, wherein $R^4$ represents an alkyl group.

Item 5.

The compound or the salt thereof according to any one of items 1 to 4, wherein $R^5$ represents a hydrogen atom or an alkyl group.

Item 6.

The compound or the salt thereof according to any one of items 1 to 5, wherein $R^3$ represents a hydrogen atom, an alkyl group, an alkenyl group, a cycloalkyl group, an aryl group, an aralkyl group, an acyl group, an alkylsulfonyl group, an arylsulfonyl group, a group represented by the formula: $—Si(R^6)_3$ (wherein $R^6$'s are the same as or different from each other and independently represent an alkyl group or an aryl group), a labeling functional group, a group having intercalating capability, a group having capability of binding to a nucleic acid, a functional group having a cleavage activity, a group having cellular or nuclear translocation capability, or a group having metal chelating capability.

Item 7.

The compound or the salt thereof according to any one of items 1 to 5, wherein:

$R^3$ represents a group represented by the formula: $R^{31}—X—$;

$R^{31}$ represents a group represented by formula (A):

[Formula 6]

(A)

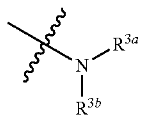

(wherein $R^{3a}$ and $R^{3b}$ are the same as or different from each other and independently represent a hydrogen atom, an alkyl group which may have a substituent, an alkenyl group which may have a substituent, a cycloalkyl group which may have a substituent, a cycloalkenyl group which may have a substituent, an aryl group which may have a substituent, or a protecting group for an amino group, or $R^{3a}$, $R^{3b}$ and a nitrogen atom adjacent to $R^{3a}$ and $R^{3b}$ together form a ring which may have a substituent), or a group represented by formula (B):

[Formula 7]

(B)

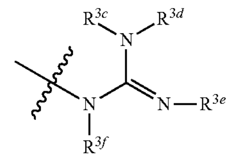

(wherein $R^{3c}$ to $R^{3f}$ are the same as or different from each other and independently represent a hydrogen atom, an alkyl group, or a protecting group for an amino group); and X represents $—C_mH_{2m}—$ (wherein m represents an integer of 1 to 10).

Item 8.

The compound or the salt thereof according to any one of items 1 to 7, wherein:

$R^1$ and $R^2$ are the same as or different from each other and independently represent a hydrogen atom, an alkyl group which may have a substituent, an aryl group which may have a substituent, an alkylcarbonyl group, an arylcarbonyl group, an alkylsulfonyl group, an arylsulfonyl group, a group represented by the formula: $—Si(R^6)_3$ (wherein $R^6$'s are the same as or different from each other and independently represent an alkyl group or an aryl group), a group represented by the formula: $—P(R^7)(R^8)$ (wherein $R^7$ and $R^8$ are the same as or different from each other and independently represent a hydroxyl group, a mercapto group, an amino group, an alkoxy group, a haloalkoxy group, a cyanoalkoxy group, an alkylthio group, a haloalkylthio group, a cyanoalkylthio group, or an alkylamino group), a dihydroxyphosphinyl group, or a hydroxymercaptophosphinyl group; or $R^1$, $R^2$, two oxygen atoms respectively adjacent to $R^1$ and $R^2$ and carbon atoms at position-3 to position-5 in a furanose together form a ring which may have a substituent.

Item 9.

The compound or the salt thereof according to any one of items 1 to 8, wherein "Base" represents a 2,4-dioxo-1,2,3,4-tetrahydropyrimidin-1-yl group which may have a substituent, a 2-oxo-1,2-dihydropyrimidin-1-yl group which may have a substituent, a purin-9-yl group which may have a substituent, or a 6-oxo-1,6-dihydro-9H-purin-9-yl group which may have a substituent.

Item 10.

The compound or the salt thereof according to item 1, wherein the compound or the salt thereof is a compound represented by formula (1A):

[Formula 8]

(1A)

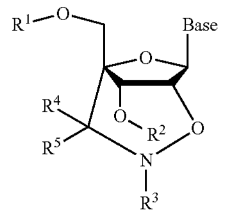

(wherein "Base" and $R^1$ to $R^5$ are as defined above) or a salt thereof.

Item 11.

The compound or the salt thereof according to item 1, wherein the compound or the salt thereof is a compound represented by formula (1B):

[Formula 9]

(1B)

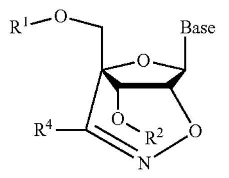

(wherein "Base", $R^1$, $R^2$, and $R^4$ are as defined above) or a salt thereof.

Item 12.

A method for producing the compound or the salt thereof according to item 1, wherein n represents 0 or n represents 1 and $R^5$ represents a hydrogen atom, the method comprising:

(I) a step of reacting a compound represented by formula (1E):

[Formula 10]

(1E)

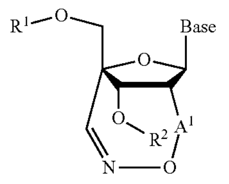

(wherein "Base", $A^1$, $R^1$ and $R^2$ are as defined in item 1) with radical represented by the formula: $R^4$ (wherein $R^4$ is as defined in item 1) or an organometallic reagent represented by the formula: $R^4M$ (wherein M represents a metal atom or an atomic group comprising a metal atom; and $R^4$ is as defined in claim 1), in which the method may further comprise:

(II) a step of dehydrogenating a compound produced in the step (I);

(III) a step of dehydrogenating and then hydrogenating the compound produced in the step (I); or (IV) a step of reacting the compound produced in the step (I) or a compound produced by dehydrogenating and then hydrogenating the compound produced in the step (I) with a compound represented by the formula: $R^3$-L (wherein L represents a leaving group; and $R^3$ is as defined in item 1 but does not represent a hydrogen atom).

Item 13.

A method for producing the compound or the salt thereof according to item 1, wherein n represents 1, $R^3$ represents a methyl group which may have one or two substituents and $R^5$ represents a hydrogen atom, the method comprising:

(I) a step of reacting a compound represented by formula (1E):

[Formula 11]

(1E)

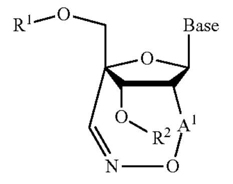

(wherein "Base", $A^1$, $R^1$ and $R^2$ are as defined in item 1) with radical represented by the formula: $R^4$ (wherein $R^4$ is as defined in item 1) or an organometallic reagent represented by the formula: $R^4M$ (wherein M represents a metal atom or an atomic group comprising a metal atom; and $R^4$ is as defined in item 1); and (II) a step of reacting the compound produced in the step (I) or a compound produced by dehydrogenating and then hydrogenating the compound produced in the step (I) with a carbonyl compound.

Item 14.

An oligonucleotide or a salt thereof, the oligonucleotide comprising a unit represented by formula (6):

[Formula 12]

(6)

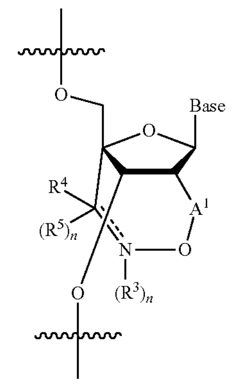

[wherein:

"Base" represents an aromatic heterocyclic group which may have a substituent, or an aromatic hydrocarbon ring group which may have a substituent;

$A^1$ represents a single bond or an alkylene group;

$R^3$ represents a hydrogen atom, an alkyl group which may have a substituent, an alkenyl group which may have a substituent, a cycloalkyl group which may have a substituent, an aryl group which may have a substituent, an acyl group which may have a substituent, a sulfonyl group which has a substituent, a silyl group which has a substituent, a functional molecule unit substituent, or a group represented by the formula: $R^{31}$—X— (wherein $R^{31}$ represents an amino group which may have a substituent; and X represents an alkylene group which may have a substituent, or a group having such a structure that at least one methylene group moiety in the alkylene group is substituted by —N($R^{32}$)— (wherein $R^{32}$ represents a hydrogen atom or an alkyl group), —O— or —S(═O)$_k$— (wherein k represents 0, 1 or 2));

$R^4$ represents a hydrogen atom, an alkyl group which may have a substituent, or an aryl group which may have a substituent;

$R^5$ represents a hydrogen atom, an alkyl group which may have a substituent, or an aryl group which may have a substituent;

$R^4$ and $R^5$ do not represent hydrogen atoms coincidentally;

a symbol represented by the following formula:

 [Formula 13]

represents a single bond or a double bond;

when the symbol represents a single bond, n represents 1; and when the symbol represents a double bond, n represents 0].

Item 15.

A method for detecting a target nucleic acid, the method comprising:

(I) a step of amplifying the target nucleic acid selectively by a nucleic acid amplification method; and (II) a step of detecting the target nucleic acid that has been amplified in the step (I), in which an oligonucleotide that is used for the amplification or the detection comprises the oligonucleotide or the salt thereof according to item 14.

Item 16.

A kit for detecting or selectively amplifying a target nucleic acid, in which:

(a) the kit comprises a primer and/or a probe, in which at least one of the primer and the probe comprises the oligonucleotide or the salt thereof according to item 14; or (b) the kit comprises a clamp nucleic acid and a primer, in which at least one of the clamp nucleic acid and the primer comprises the oligonucleotide or the salt thereof according to item 14.

Item 17.

A pharmaceutical composition which comprises the compound or the salt thereof according to any one of items 1 to 11 or comprises the oligonucleotide or the salt thereof according to item 14.

According to the present invention, a novel artificial nucleic acid can be provided, which us useful in various genome technologies.

DETAILED DESCRIPTION OF THE PREFERRED EMBODIMENTS

Definitions of Terms

Figure 1A:
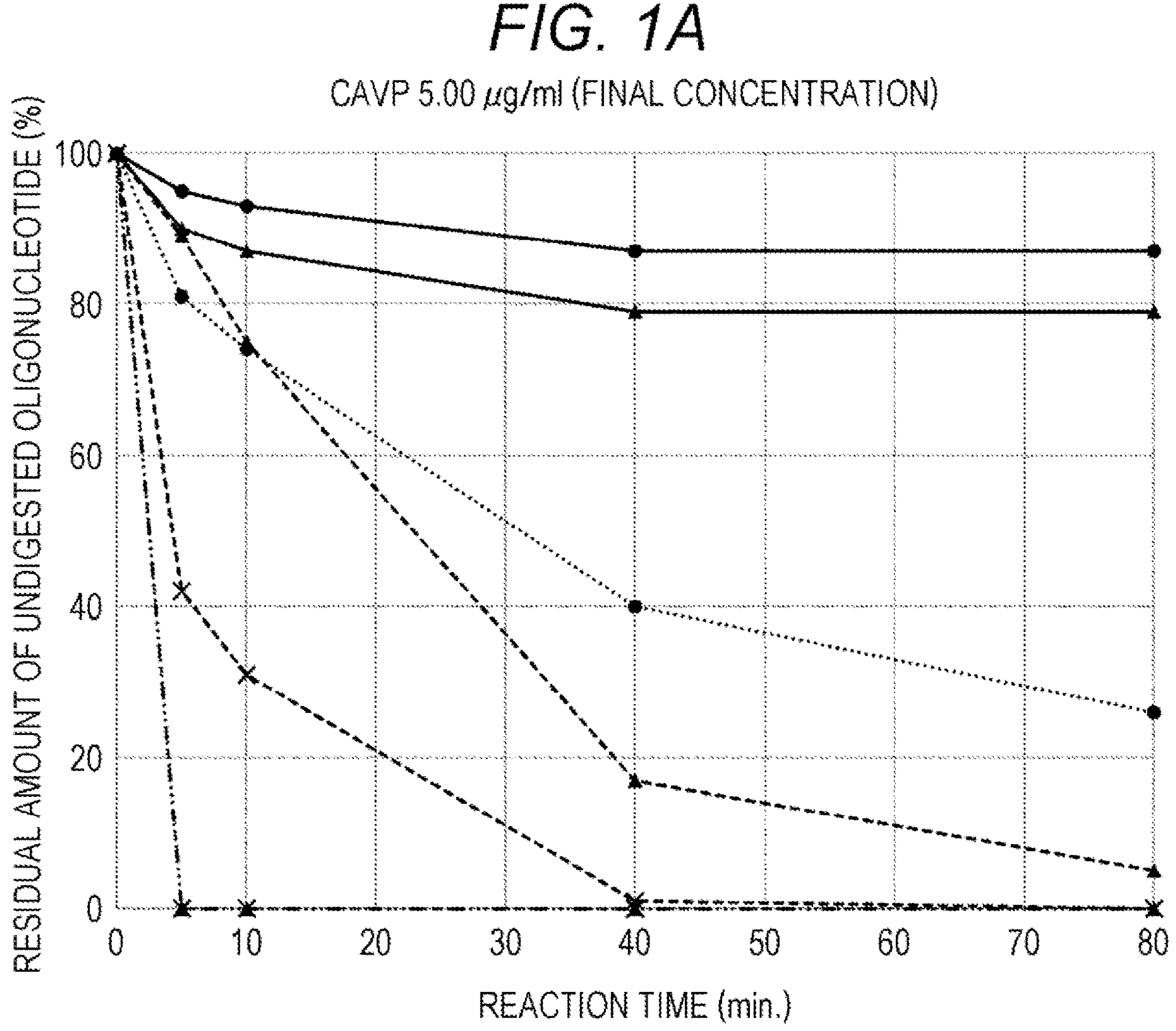
FIG. 1A shows graphs illustrating the relationship between the reaction time of a digestive enzyme at a final concentration of 5.0011 g/mL and the residual ratio of an undigested oligonucleotide.

In the present description, the term "alkyl group" refers to a monovalent group having such a structure that one hydrogen atom is removed from a linear or branched saturated hydrocarbon.

The number of carbon atoms in the alkyl group is not particularly limited, and is for example 1 to 20, preferably 1 to 10, more preferably 1 to 6, particularly preferably 1 to 4.

Examples of the alkyl group include a methyl group, an ethyl group, a propyl group (e.g., a n-propyl group, an i-propyl group), a butyl group (e.g., a n-butyl group, an i-butyl group, an s-butyl group, a t-butyl group), a pentyl group (e.g., a n-pentyl group, an i-pentyl group, a neopentyl group), a hexyl group, a heptyl group, an octyl group (e.g., a n-octyl group, a 2-ethylhexyl group), a nonyl group, and a decyl group.

In the present description, the term "alkylene group" refers to a bivalent group having such a structure that two hydrogen atoms are removed from a linear or branched saturated hydrocarbon.

The number of carbon atoms in the alkylene group is not particularly limited, and is for example 1 to 10, preferably 1 to 8, more preferably 1 to 6.

Examples of the alkylene group include a $C_1$-alkylene group (e.g., a methylene group), a $C_2$-alkylene group (e.g., a methylmethylene group, a dimethylene group), a $C_3$-alkylene group (e.g., a trimethylene group, a dimethylmethylene group), a $C_4$-alkylene group (e.g., a tetramethylene group), a $C_5$-alkylene group (e.g., a pentamethylene group), and a $C_6$-alkylene group (e.g., a hexamethylene group).

In the present description, the term "alkenyl group" refers to a monovalent group having such a structure that one hydrogen atom is removed from a linear or branched unsaturated hydrocarbon containing a carbon-carbon double bond.

The number of carbon atoms in the alkenyl group is not particularly limited, and is for example 2 to 20, preferably 2 to 10, more preferably 2 to 6.

Examples of the alkenyl group include an ethenyl group (i.e., a vinyl group), a propenyl group (e.g., a 1-propenyl group, an allyl group), a butenyl group, a pentenyl group, a hexenyl group, a geranyl group, and a farnesyl group.

In the present description, the term "alkynyl group" refers to a monovalent group having such a structure that one hydrogen atom is removed from a linear or branched unsaturated hydrocarbon containing a carbon-carbon triple bond.

The number of carbon atoms in the alkynyl group is not particularly limited, and is for example 2 to 20, preferably 2 to 10, more preferably 2 to 6.

Examples of the alkynyl group include an ethynyl group, a propargyl group, and a 1-butynyl group.

In the present description, the term "cycloalkyl group" refers to a monovalent group derived from a saturated aliphatic hydrocarbon ring.

The number of carbon atoms in the cycloalkyl group is not particularly limited, and is for example 3 to 20, preferably 5 to 12, more preferably 5 to 10.

Examples of the cycloalkyl group include a cyclopropyl group, a cyclobutyl group, a cyclopentyl group, a cyclohexyl group, a cycloheptyl group, a cyclooctyl group, a norbornyl group, and an adamantyl group.

In the present description, the term "cycloalkenyl group" refers to a monovalent group derived from an unsaturated aliphatic hydrocarbon ring containing a carbon-carbon double bond.

The number of carbon atoms in the cycloalkenyl group is not particularly limited, and is for example 3 to 20, preferably 5 to 12, more preferably 5 to 10.

Examples of the cycloalkenyl group include a cyclopropenyl group, a cyclobutenyl group, a cyclopentenyl group, a cyclohexenyl group, a norbornenyl group, and an adamantenyl group.

In the present description, the term "aromatic hydrocarbon ring group" refers to a monovalent group derived from an aromatic hydrocarbon ring, and is also referred to as an "aryl group".

The number of constituent atoms in the aromatic hydrocarbon ring is not particularly limited, and is for example 6 to 20, preferably 6 to 14, more preferably 6 to 12, particularly preferably 6 to 10.

The aromatic hydrocarbon ring may be a monocyclic ring or a condensed ring (e.g., a di- to tri-cyclic condensed ring).

Examples of the aromatic hydrocarbon ring group include a phenyl group, an indenyl group, a naphthyl group, a fluorenyl group, a phenanthrenyl group, and an anthracenyl group.

In the present description, the term "heterocyclic ring" is used in the meaning that an "aliphatic heterocyclic ring" and an "aromatic heterocyclic ring" are included.

In the present description, the term "aliphatic heterocyclic ring" refers to an aliphatic ring which contains, as ring constituent atoms, a carbon atom and at least one hetero atom selected from the group consisting of a nitrogen atom, an oxygen atom, a sulfur atom, a silicon atom and the like.

The number of constituent atoms in the aliphatic heterocyclic ring is not particularly limited, and is for example 5 to 20, preferably 5 to 12, more preferably 6 to 10.

The number of hetero atom(s) among the constituent atoms of the aliphatic heterocyclic ring is not particularly limited, and is for example 1 to 4.

Examples of the aliphatic heterocyclic ring include an oxygenated aliphatic heterocyclic ring (e.g., tetrahydrofuran, dioxolane, pyran, tetrahydropyran, dioxane), a sulfur-containing aliphatic heterocyclic ring (e.g., tetrahydrothiophene, thiopyran, tetrahydrothiopyran), a nitrogenated aliphatic heterocyclic ring (e.g., pyrrolidine, piperidine, azepane), a nitrogenated and oxygenated aliphatic heterocyclic ring (e.g., morpholine), a nitrogenated and sulfur-containing aliphatic heterocyclic ring (e.g., thiomorpholine), and an aliphatic heterocyclic ring containing a siloxane bond.

In the present description, the term "aromatic heterocyclic ring" refers to an aromatic ring containing, as ring constituent atoms, a carbon atom and at least one hetero atom selected from the group consisting of a nitrogen atom, an oxygen atom, a sulfur atom and the like.

The number of constituent atoms in the aromatic heterocyclic ring is not particularly limited, and is for example 5 to 20, preferably 5 to 12, more preferably 6 to 10.

The number of hetero atom(s) among the constituent atoms of the aromatic heterocyclic ring is not particularly limited, and is for example 1 to 4.

The aromatic heterocyclic ring may be a monocyclic ring or a condensed ring (e.g., a di- or tri-cyclic condensed ring).

Examples of the aromatic heterocyclic ring include an oxygenated aromatic heterocyclic ring (e.g., furan, benzofuran, isobenzofuran, chromene, benzopyran, xanthene), a sulfur-containing aromatic heterocyclic ring (e.g., thiophene, thianthrene), a nitrogenated aromatic heterocyclic ring (e.g., pyrrole, imidazole, pyrazole, triazole, pyridine, pyrazine, pyrimidine, pyridazine, indole, isoindole, indolizine, purine, quinoline, isoquinoline, 1,8-naphthyridine, quinoxaline, quinazoline, cinnoline, phthalazine, pteridine, carbazole, phenanthridine, acridine, perimidine, phenazine), an oxygenated and sulfur-containing aromatic heterocyclic ring (e.g., phenoxathiin), a nitrogenated and oxygenated aromatic heterocyclic ring (e.g., oxazole, isoxazole, furazan, phenoxazine), and a nitrogenated and sulfur-containing aromatic heterocyclic ring (e.g., thiazole, isothiazole, phenothiazine).

In the present description, the term "heterocyclic group" refers to a monovalent group having such a structure that one hydrogen atom is removed from the heterocyclic ring.

In the present description, the wording "may have a substituent" or "may be substituted by a substituent" is used in the meaning including both of a case where no substituent is contained and a case where one substituent or two or more same-type or different-type substituents are contained in place of an arbitrary hydrogen atom. When a substituent or substituents is/are contained, the number of the substituent(s) is not particularly limited, and is for example 1 to 3, preferably 1 or 2.

In the present description, the term "substituent" refers to an atom or an atomic group which is replaced for a hydrogen atom. Examples of the substituent include a halogen atom (e.g., a fluorine atom, a chlorine atom, a bromine atom, an iodine atom), an oxo group (=O), a thioxo group (=S), a hydroxyl group, a mercapto group, an amino group, a carboxy group, an alkyl group, an alkenyl group, a cycloalkyl group, a cycloalkenyl group, an aryl group, an alkynyl group, an acyl group, an alkylsulfonyl group, an arylsulfonyl group, a cyano group, a heterocyclic group, and a combination of any two or more of them (e.g., a haloalkyl group, a cyanoalkyl group, an aralkyl group, an alkoxy group, an alkylamino group).

The term "a combination of two or more of them" includes an arbitrary combination of the groups which are exemplified as the substituents.

In the present description, the term "Cx-y" means that the number of carbon atom(s) in a group following this term is x to y inclusive. Each of x and y represents a positive integer, in which x and y satisfy the requirement represented by the formula: $x<y$.

In the present description, the term "haloalkyl group" refers to an alkyl group substituted by one halogen atom or two or more same or different halogen atoms.

A preferred example of the haloalkyl group is a $C_{1-6}$ haloalkyl group, a more preferred example is a $C_{1-4}$ haloalkyl group, and a still more preferred example is a trifluoromethyl group, a trichloromethyl group, or a 2,2,2-trifluoroethyl group.

In the present description, the term "cyanoalkyl group" refers to an alkyl group substituted by one cyano group or two or more cyano groups.

A preferred example of the cyanoalkyl group is a $C_{1-6}$ cyanoalkyl group, a more preferred example is a $C_{1-4}$ cyanoalkyl group, and a still more referred example is a cyanomethyl group or a 2-cyanoethyl group.

In the present description, the term "aralkyl group" refers to an alkyl group substituted by one aryl group or two or more same or different aryl groups.

A preferred example of the aralkyl group is a $C_{6-14}$-aryl-$C_{1-4}$-alkyl group, and a more preferred example is a phenylmethyl group (i.e., a benzyl group), a phenylethyl group (i.e., a phenethyl group), a naphthylmethyl group, a naphthylethyl group, a triphenylmethyl group (i.e., a trityl group), or a fluorenylmethyl group.

In the present description, the term "alkoxy group" refers to a group represented by the formula: —O-alkyl. A preferred example of the alkoxy group is a $C_{1-6}$ alkoxy group, and a more preferred example is a methoxy group, an ethoxy group, a propoxy group (e.g., a n-propoxy group, an i-propoxy group), or a butoxy group (e.g., a t-butoxy group).

The haloalkoxy group and the cyanoalkoxy group refer to a group represented by the formula: —O-haloalkyl and a group represented by the formula: —O-cyanoalkyl, respectively.

In the present description, the term "alkylthio group" refers to a group represented by the formula: —S-alkyl. A preferred example of the alkylthio group is a $C_{1-6}$ alkylthio group, and a more preferred example is a methylthio group, an ethylthio group, a propylthio group (e.g., a n-propylthio group, an i-propylthio group), or a butylthio group.

A haloalkylthio group and a cyanoalkylthio group refer to a group represented by the formula: —S-haloalkyl and a group represented by the formula: —S-cyanoalkyl, respectively.

In the present description, the term "alkylamino group" refers to an amino group which is substituted by one or two same or different alkyl groups.

The alkylamino group includes a monoalkylamino group and a dialkylamino group.

A preferred example of the monoalkylamino group is a mono-$C_{1-6}$ alkylamino group, and a more preferred example is a monomethylamino group, a monoethylamino group, a monopropylamino group (e.g., a mono(n-propyl)amino group, a mono(i-propyl)amino group), or a monobutylamino group.

A preferred example of the dialkylamino group is a di-$C_{1-6}$ alkylamino group, and a more preferred example is a dimethylamino group, a diethylamino group, a dipropylamino group (e.g., a di(n-propyl)amino group, a di(i-propyl)amino group), or a dibutylamino group.

In the present description, the term "phosphino group which has a substituent" refers to a group having such a structure that at least one hydrogen atom in a phosphino group (—$PH_2$) is substituted by another atom or atomic group.

An example of the phosphino group which has a substituent is a group represented by the formula: —$P(R^7)(R^8)$ (wherein $R^7$ and $R^8$ are the same as or different from each other and independently represent a hydroxyl group, a mercapto group, an amino group, an alkoxy group, a haloalkoxy group, a cyanoalkoxy group, an alkylthio group, a haloalkylthio group, a cyanoalkylthio group, or an alkylamino group).

In the present description, the term "dihydroxyphosphinyl group which may have a substituent" refers to a dihydroxyphosphinyl group (i.e., a phosphono group) (—P(═O)$(OH)_2$) or a dihydroxyphosphinyl group in which at least one hydrogen atom is substituted by another atom or an atomic group (e.g., a protecting group for a hydroxyl group).

The latter group includes a group represented by the following formula:

[Formula 14]

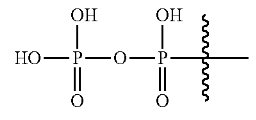

which may have a substituent (hereinafter, also referred to as a "diphosphate group"), and a group represented by the following formula:

[Formula 15]

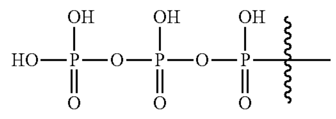

which may have a substituent (hereinafter, also referred to as a "triphosphate group").

In the present description, the term "hydroxymercaptophosphinyl group which may have a substituent" refers to a hydroxymercaptophosphinyl group (—P(═O)(OH)(SH)) or a hydroxymercaptophosphinyl group in which at least one hydrogen atom is substituted by another atom or an atomic group (e.g., a protecting group for a hydroxyl group).

In the present description, the term "protecting group for a hydroxyl group" refers to a monovalent group which can prevent a hydroxyl group from being involved in a reaction for the synthesis of a compound or a salt thereof or a reaction for the synthesis of an oligonucleotide or a salt thereof.

An example of the protecting group for a hydroxyl group is, but is not limited to, a group which is stable under an acidic or neutral condition and can be cleaved by a method such as a hydrogenolysis, a hydrolysis, an electrolysis and a photodissociation.

Specific examples of the protecting group for a hydroxyl group include an acyl group which may have a substituent, a sulfonyl group which has a substituent, and a silyl group which has a substituent.

In the present description, the term "acyl group" refers to a group represented by the formula: —C(═O)—R (wherein R represents a hydrocarbon group). The hydrocarbon group represented by R may be a linear or branched hydrocarbon group (e.g., an alkyl group), or may be a saturated or unsaturated hydrocarbon ring group (e.g., a cycloalkyl group, an aryl group), or may be a combination thereof (e.g., an aralkyl group).

Examples of the acyl group include an alkylcarbonyl group, an arylcarbonyl group, and an aralkylcarbonyl group.

A preferred example of the alkylcarbonyl group is a ($C_{1-10}$-alkyl)carbonyl group, and a more preferred example is an acetyl group, a propionyl group, a butyryl group, an isobutyryl group, a pentanoyl group, a pivaloyl group, a valeryl group, an isovaleryl group, an octanoyl group, a nonanoyl group, or a decanoyl group.

A preferred example of the arylcarbonyl group is a ($C_{6-14}$-aryl)carbonyl group, and a more preferred example is a benzoyl group, or a naphthoyl group (i.e., an α-naphthoyl group, a β-naphthoyl group).

A preferred example of the aralkylcarbonyl group is a ($C_{6-14}$-aryl-$C_{1-4}$-alkyl)carbonyl group, and a more preferred example is a benzylcarbonyl group.

With respect to the acyl group in the "acyloxy group", the "acylthio group" and the "acylamino group", the same groups as mentioned above can be exemplified.

In the present description, the term "sulfonyl group which has (having) a substituent" refers to a group represented by the formula: —S(═O)$_2$R (wherein R is as defined above).

The sulfonyl group which has a substituent includes a sulfonyl group which has an alkyl group which may have a substituent, and a sulfonyl group which has an aryl group which may have a substituent. A preferred example of the sulfonyl group having an alkyl group is a $C_{1-6}$-alkylsulfonyl group, and a more preferred example is a methanesulfonyl group or an ethanesulfonyl group.

A preferred example of the sulfonyl group having an aryl group is a $C_{6-14}$-arylsulfonyl group, and a more preferred example is a benzenesulfonyl group or a p-toluenesulfonyl group.

In the present description, the term "silyl group which has (having) a substituent" refers to a silyl group having such a structure that at least one hydrogen atom in a silyl group (—$SiH_3$) is substituted by another atom or an atomic group.

A typical example of the "silyl group which has (having) a substituent" is a group represented by the formula: —Si$(R^6)_3$ (wherein $R^6$'s are the same as or different from each other and independently represent an alkyl group or an aryl group). Examples of the group include a trialkylsilyl group (e.g., a tri-$C_{1-6}$-alkylsilyl group such as a trimethylsilyl group, a triethylsilyl group, a triisopropylsilyl group and a t-butyldimethylsilyl group), a dialkylarylsilyl group (e.g., a di-$C_{1-6}$-alkyl-$C_{6-14}$-arylsilyl group such as a dimethyl(phenyl)silyl group), an alkyldiarylsilyl group (e.g., a $C_{1-6}$-alkyldi-$C_{6-14}$-arylsilyl group such as a t-butyldiphenylsilyl group), and a triarylsilyl group (e.g., a tri-$C_{6-14}$-arylsilyl group such as a triphenylsilyl group).

In the present description, the term "protecting group for an amino group" refers to a monovalent group which can prevent an amino group from being involved in a reaction in the synthesis of a compound or a salt thereof or the synthesis of an oligonucleotide or a salt thereof.

The protecting group for an amino group is, for example, but is not limited to, a group which is stable under an acidic or neutral condition and can be cleaved by a method such as a hydrogenolysis, a hydrolysis, an electrolysis and a photodissociation.

Examples of the protecting group for an amino group include an acyl group which may have a substituent (e.g., an alkylcarbonyl group which may have a substituent, an arylcarbonyl group which may have a substituent, an aralkylcarbonyl group which may have a substituent), an N,N-dialkylformamidyl group which may have a substituent, an alkoxycarbonyl group which may have a substituent, an alkenyloxycarbonyl group which may have a substituent, an aryloxycarbonyl group which may have a substituent, an aralkyloxycarbonyl group which may have a substituent, and a sulfonyl group which has a substituent.

In the present description, the term "formamidyl group" refers to a group represented by the formula: ═CH—$NH_2$. A preferred example of an N,N-dialkylformamidyl group is an N,N-di($C_{1-6}$-alkyl)formamidyl group, a more preferred example is an N,N-di($C_{1-4}$-alkyl)formamidyl group, and a still more preferred example is an N,N-dimethylformamidyl group or an N,N-diethylformamidyl group.

In the present description, the term "alkoxycarbonyl group" refers to a group represented by the formula: —C(═O)—O-alkyl.

A preferred example of the alkoxycarbonyl group is a ($C_{1-6}$-alkoxy)carbonyl group, and a more preferred example is a methoxycarbonyl group, an ethoxycarbonyl group, a propoxycarbonyl group, or a butoxycarbonyl group (e.g., a t-butoxycarbonyl group).

In the present description, the term "alkenyloxycarbonyl group" refers to a group represented by the formula: —C(═O)—O-alkenyl.

A preferred example of the alkenyloxycarbonyl group is a ($C_{2-9}$-alkenyloxy)carbonyl group, and a more preferred example is an allyloxycarbonyl group.

In the present description, the term "aryloxycarbonyl group" refers to a group represented by the formula: —C(═O)—O-aryl.

A preferred example of the aryloxycarbonyl group is a ($C_{6-14}$-aryloxy)carbonyl group, and a more preferred example is a phenoxycarbonyl group or a naphthoxycarbonyl group.

In the present description, the term "aralkyloxycarbonyl group" refers to a group represented by the formula: —C(═O)—O-aralkyl.

A preferred example of the aralkyloxycarbonyl group is a ($C_{6-14}$-aryl-$C_{1-4}$-alkoxy)carbonyl group, and a more preferred example is a benzyloxycarbonyl group or a fluorenylmethyloxycarbonyl group.

The term "functional molecule unit substituent" as used herein refers to a concept including a labeling functional group (e.g., a fluorescently labeling functional group, a chemoluminescently labeling functional group, a group containing a radiation-emitting nuclear species), a group having intercalating capability, a group having capability of binding to a nucleic acid, a functional group having capability of cleaving a nucleic acid, a group having cellular or nuclear translocation capability, a group having metal chelating capability, and the like.

Examples of the fluorescently labeling functional group include residues of fluorescently labeling reagents such as carboxyfluorescein (FAM), fluorescein isothiocyanate (FITC), carboxytetramethylrhodamine (TAMRA) and thiazole orange (1-methyl-4-[(3-methyl-2(3H)-benzothiazolylidene)methyl]quinolinium p-tosylate). Examples of the chemoluminescently labeling functional group include residues of chemoluminescently labeling reagents such as tris(bipyridine)ruthenium (II) chloride. Examples of the group containing a radiation-emitting nuclear species include groups each containing $^{11}CH_3$—, $^{14}CH_3$—, $^{18}F$— or $^{32}P$—.

Examples of the group having intercalating capability include a group having an anthracene skeleton, a group having a pyrene skeleton, a group having an anthraquinone skeleton, a group having an acridine skeleton and a group having a naphthalimide skeleton. Other example is a residue of an intercalating agent such as tamoxifen.

Examples of the group having group having capability of binding to a nucleic acid include residues of nucleic acid binding agents such as netropsin, distamine and PI (Pyrrole Imidazole)polyamide.

Examples of the functional group having capability of cleaving a nucleic acid include residues of nucleic acid cleaving agents such as endonucleases and a bis(bipyridine) chrysenequinone diimine rhodium (II) complex.

Examples of the group having cellular or nuclear translocation capability include residues of cellular or nuclear translocation signal peptides such as TAT (Twin-Arginine Translocation) signal peptide, polyarginine, GalNac (N-acetylgalactosamine) and a signal peptide derived from SV40T antigen.

Examples of the group having meal chelating capability include residues of metal chelating agents such as EDTA, crown ether and a cryptand.

In the present description, the wording "hybridize" refers to a matter that the full length or a part of a given polynucleotide or oligonucleotide and the full length or a part of another polynucleotide or oligonucleotide together form a double strand through hydrogen bonds under a stringent condition. The "stringent condition" may be one which has been commonly employed by a person skilled in the art in the hybridization of a polynucleotide or an oligonucleotide. For example, when there is at least 50%, preferably at least 75%, more preferably at least 90% sequence identity between two polynucleotide or oligonucleotide molecules, the "stringent condition" may be a condition where one of the polynucleotide or oligonucleotide molecules can hybridize with the other specifically. It is known that the stringency in the hybridization is a function of a temperature, a salt concentration, a nucleotide length and a GC content in a polynucleotide or oligonucleotide, and the concentration of a chaotropic agent in a hybridization buffer solution. For example, as the stringent condition, a condition described in Sambrook, J. et. al., 1998, Molecular Cloning: A Laboratory Manual (second edition), Cold Spring Harbor Laboratory Press, New York can be employed.

In the present description, the term "test" refers to the matter that an analyte, e.g., a nucleic acid, in a specimen is examined for the purpose of diagnosis, research or the like. The term "test specimen" refers to a specimen to be subjected to a test.

In the present description, the upper limit and the lower limit of a numerical range may be combined arbitrarily.

<<Compound or Salt Thereof>

The compound or a salt thereof according to the present invention is a compound represented by formula (1) or a salt thereof:

[Formula 16]

(1)

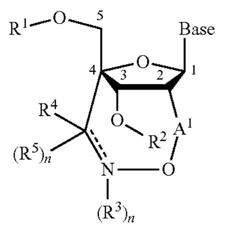

(wherein "Base", $A^1$, $R^1$ to $R^5$, and n are as defined above, position numbers are assigned to carbon atoms in the furanose).

Hereinbelow, a compound represented by formula (N) or a salt thereof refers to a "compound (N)".

A compound (1) is referred to as a "nucleotide" when R' or $R^2$ represents a dihydroxyphosphinyl group which may have a substituent or a hydroxymercaptophosphinyl group which may have a substituent, and is referred to as a "nucleoside" when $R^1$ and $R^2$ each represent another group.

Preferred examples of "Base" include an aromatic heterocyclic group which may have a substituent.

The aromatic heterocyclic group is preferably a nitrogenated aromatic heterocyclic group.

The nitrogenated aromatic heterocyclic group is preferably a 6- to 10-membered nitrogenated aromatic heterocyclic group. The 6- to 10-membered nitrogenated aromatic heterocyclic group is preferably a 2,4-dioxo-1,2,3,4-tetrahydropyrimidin-1-yl group, a 2-oxo-1,2-dihydropyrimidin-1-yl group, a purin-9-yl group, or a 6-oxo-1,6-dihydro-9H-purin-9-yl group.

A preferred example of the substituent which replaces in the aromatic heterocyclic group is at least one residue selected from the group consisting of an alkyl group, an acyl group, and an amino group which may be substituted by a protecting group for an amino group. The number of the substituent(s) is not particularly limited, and is for example 1 to 3.

A more preferred example of "Base" is a thyminyl group which may have a substituent, a cytosinyl group which may have a substituent, an adenyl group which may have a substituent, or a guanyl group which may have a substituent. The substituent is preferably at least one residue selected from the group consisting of an alkyl group, an acyl group, and an N,N-dialkylformamidyl group, more preferably a $C_{1-4}$-alkyl group, a ($C_{1-4}$-alkyl)carbonyl group, a ($C_{6-14}$-aryl)carbonyl group, or an N,N-di($C_{1-4}$-alkyl)formamidyl group. The number of the substituent(s) is preferably 1 to 3.

A still more preferred example of "Base" is a group selected from the group consisting of:

a 2,4-dioxo-5-methyl-1,2,3,4-tetrahydropyrimidin-1-yl group (e.g., a thymin-1-yl group), a 2-oxo-4-amino-1,2-dihydropyrimidin-1-yl group (i.e., a cytosin-1-yl group), a 2-oxo-4-acylamino-1,2-dihydropyrimidin-1-yl group (i.e., an N-acyl-cytosin-1-yl group), a 2-oxo-4-amino-5-methyl-1,2-dihydropyrimidin-1-yl group (i.e., a 5-methylcytosin-1-yl group), a 2-oxo-4-acylamino-5-methyl-1,2-dihydropyrimidin-1-yl group (i.e., an N-acyl-5-methylcytosin-1-yl group), a 6-amino-9H-purin-9-yl group (i.e., an adenin-9-yl group), a 6-acylamino-9H-purin-9-yl group (i.e., an N-acyl-adenin-9-yl group), a 2-amino-6-oxo-1,6-dihydro-9H-purin-9-yl group (e.g., guanin-9-yl group), a 2-acylamino-6-oxo-1,6-dihydro-9H-purin-9-yl group (e.g., an N-acyl-guanin-9-yl group), and a 2-(N,N-dialkylformamidyl)amino-6-oxo-1,6-dihydro-9H-purin-9-yl group (e.g., an N—(N,N-dialkylformamidyl)-guanin-9-yl group).

A most preferred example of "Base" is a group selected from the group consisting of:

a thymin-1-yl group, a 5-methylcytosin-1-yl group, an N-acetyl-5-methylcytosin-1-yl group, an N-isobutyryl-5-methylcytosin-1-yl group, an N-benzoyl-5-methylcytosin-1-yl group, an adenin-9-yl group, an N-acetyl-adenin-9-yl group, an N-isobutyryl-adenin-9-yl group, an N-benzoyl-adenin-9-yl group, a guanin-9-yl group, an N-acetyl-guanin-9-yl group, an N-isobutyrylguanin-9-yl group, an N-benzoyl-guanin-9-yl group, and an N—(N,N-dimethylformamidyl)-guanin-9-yl group.

$A^1$ is preferably a single bond or a $C_1$-2 alkylene group (e.g., a methylene group, a dimethylene group), more preferably a single bond.

A preferred example of 10 is a group selected from the group consisting of:

a hydrogen atom;

an alkyl group which may have a substituent;

an aryl group which may have a substituent;

a protecting group for a hydroxyl group;

a phosphino group which has a substituent;

a dihydroxyphosphinyl group which may have a substituent; and a hydroxymercaptophosphinyl group which may have a substituent.

The "alkyl group which may have a substituent" represented by 10 is preferably an alkyl group which may have at least one substituent selected from the group consisting of a halogen atom, an alkoxy group and an aryl group, more preferably an alkyl group which may be substituted by an alkoxy group or an aralkyl group which may be substituted by an alkoxy group. The number of the substituent(s) is preferably 1 to 3.

The "aryl group which may have a substituent" represented by $R^1$ is preferably an aryl group which may have at least one substituent selected from the group consisting of a halogen atom, an alkyl group and an alkoxy group, more preferably an aryl group which may be substituted by an alkoxy group. The number of the substituent(s) is preferably 1 to 3.

The "protecting group for a hydroxyl group" represented by $R^1$ is preferably an alkylcarbonyl group, an arylcarbonyl group, an alkylsulfonyl group, an arylsulfonyl group, or a group represented by the formula: —$Si(R^6)_3$ (wherein $R^6$'s are the same as or different from each other and independently represent an alkyl group or an aryl group).

The "phosphino group which has a substituent" represented by R' is preferably a group represented by the formula: —$P(R^7)(R^8)$ (wherein $R^7$ and $R^8$ are the same as or different from each other and independently represent a hydroxyl group, a mercapto group, an amino group, an alkoxy group, a haloalkoxy group, a cyanoalkoxy group, an alkylthio group, a haloalkylthio group, a cyanoalkylthio group, or an alkylamino group). A more preferred example of the group is a phosphino group represented by the formula:

[Formula 17]

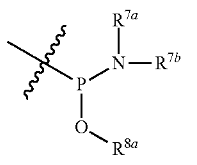

(wherein $R^{7a}$ and $R^{7b}$ are the same as or different from each other and independently represent a hydrogen atom or an alkyl group; and $R^{8a}$ represents a hydrogen atom, an alkyl group, a haloalkyl group, or a cyanoalkyl group).

The "dihydroxyphosphinyl group which may have a substituent" represented by $R^1$ is preferably a dihydroxyphosphinyl group, a diphosphate group, or a triphosphate group, more preferably a dihydroxyphosphinyl group. These groups may have a protecting group for a hydroxyl group as a substituent, in which each of all or some of hydrogen atoms may be substituted by a protecting group for a hydroxyl group.

The "hydroxymercaptophosphinyl group which may have a substituent" represented by $R^1$ is preferably a hydroxymercaptophosphinyl group.

A most preferred example of $R^1$ is a hydrogen atom, a methyl group, an ethyl group, a propyl group, a butyl group, an allyl group, a benzyl group, a trityl group, a methoxymethyl group, a p-methoxybenzyl group, a monomethoxytrityl group, a dimethoxytrityl group, an acetyl group, an isobutyryl group, a benzoyl group, a methanesulfonyl group, a p-toluenesulfonyl group, a trimethylsilyl group, a triethylsilyl group, a triisopropylsilyl group, a t-butyldimethylsilyl group, a t-butyldiphenylsilyl group, a phosphino group represented by either one of the formulae:

[Formula 18]

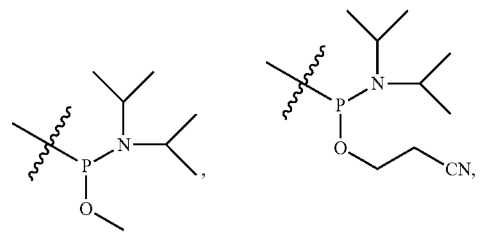

a dihydroxyphosphinyl group, or a hydroxymercaptophosphinyl group.

Preferred examples of $R^2$ are the same as those of $R^1$.

A preferred example of the combination of $R^1$ and $R^2$ is a combination in which $R^1$ is a hydrogen atom or a dimethoxytrityl group (e.g., a 4,4'-dimethoxytrityl group) and $R^2$ is a phosphino group represented by the formula:

[Formula 19]

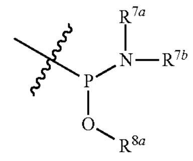

(wherein $R^{7a}$ and $R^{7b}$ are the same as or different from each other and independently represent a hydrogen atom or an alkyl group; and $R^8$ represents a hydrogen atom, an alkyl group, a haloalkyl group, or a cyanoalkyl group).

When $R^1$ and $R^2$, two oxygen atoms respectively adjacent to $R^1$ and $R^2$ and carbon atoms located at position-3 to position-5 in a furanose together form a ring, a preferred example of the ring is a 6- to 10-membered aliphatic heterocyclic ring which may have a substituent, in which a preferred example of the substituent is an alkyl group.

A more preferred example of the ring is an aliphatic heterocyclic ring represented by either one of the following formulae:

[Formula 20]

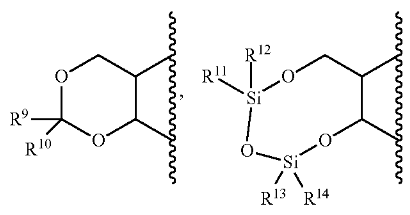

(wherein $R^9$ and $R^{10}$ are the same as or different from each other and independently represent a hydrogen atom or an alkyl group; and $R^{11}$ to $R^{14}$ are the same as or different from each other and independently represent an alkyl group).

A still more preferred example of the ring is a ring represented by any one of the formulae.

[Formula 21]

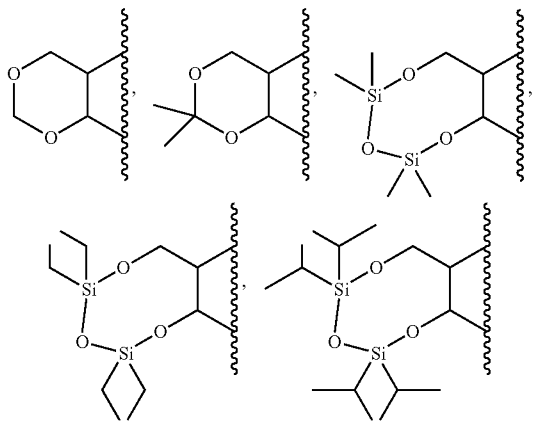

In one embodiment, $R^3$ is preferably a hydrogen atom, an alkyl group, an alkenyl group, a cycloalkyl group, an aryl group, an aralkyl group, an acyl group, an alkylsulfonyl group, an arylsulfonyl group, a group represented by the formula: $—Si(R^6)_3$ (wherein $R^6$'s are the same as or different from each other and independently represent an alkyl group or an aryl group), a labeling functional group, a group having intercalating capability, a group having capability of binding to a nucleic acid, a functional group having capability of cleaving a nucleic acid, a group having cellular or nuclear translocation capability, or a group having metal chelating capability.

In another embodiment, $R^3$ is preferably a group represented by the formula: $R^{31}—X—$.

A preferred example of $R^{31}$ is a group represented by formula (A):

[Formula 22]

(A)

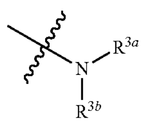

(wherein $R^{3a}$ and $R^{3b}$ are the same as or different from each other and independently represent a hydrogen atom, an alkyl group which may have a substituent, an alkenyl group which may have a substituent, a cycloalkyl group which may have a substituent, a cycloalkenyl group which may have a substituent, an aryl group which may have a substituent, or a protecting group for an amino group, or $R^{3a}$, $R^{3b}$ and the adjacent nitrogen atom together form a ring which may have a substituent).

$R^{3a}$ is preferably a hydrogen atom, an alkyl group, an aryl group, an aralkyl group, or a protecting group for an amino group, more preferably a hydrogen atom, an alkyl group, or a protecting group for an amino group.

The "protecting group for an amino group" represented by Ria is preferably a $(C_{1-4}$-alkyl)carbonyl group or a $(C_{1-4}$-haloalkyl)carbonyl group, more preferably an acetyl group or a trifluoromethylcarbonyl group.

Preferred examples of $R^{3b}$ are the same as those of $R^{3a}$.

A preferred example of the combination of $R^{3a}$ and $R^{3b}$ is a combination in which each of $R^{3a}$ and $R^{3b}$ is a hydrogen atom, a combination in which $R^{3a}$ is a hydrogen atom and $R^{3b}$ is an acetyl group or a trifluoromethylcarbonyl group, a combination in which each of $R^{3a}$ and $R^{3b}$ is a methyl group, or a combination in which each of $R^{3a}$ and $R^{3b}$ is an acetyl group or a trifluoromethylcarbonyl group.

When $R^{3a}$, $R^{3b}$ and nitrogen atoms respectively adjacent to $R^{3a}$, $R^{3b}$ together form a ring, a preferred example of the ring is a 5- to 10-membered nitrogenated aliphatic heterocyclic ring which may have a substituent, in which a preferred example of the substituent is an alkyl group or an acyl group.

A more preferred example of the ring is a nitrogenated aliphatic heterocyclic ring represented by the following formula:

[Formula 23]

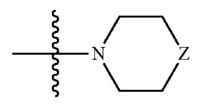

[wherein Z represents a single bond, an oxygen atom, $S(=O)_p$ (wherein p represents 0, 1 or 2), $C(R^{15})(R^{16})$ (wherein $R^{15}$ and $R^{16}$ are the same as or different from each other and independently represent a hydrogen atom or an alkyl group), or $NR^{17}$ (wherein $R^{17}$ represents a hydrogen atom, an alkyl group, or an acyl group)].

A still more preferred example of the ring is a ring represented by any one of the formulae:

[Formula 24]

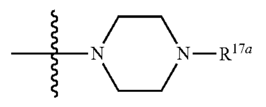

[wherein $R^{17a}$ represents a hydrogen atom, a linear or branched $C_{1-4}$ alkyl group (e.g., a methyl group, an ethyl group, a propyl group, a butyl group), or a (linear or branched $C_{1-4}$-alkyl)carbonyl group (e.g., a methylcarbonyl group, an ethylcarbonyl group, a propylcarbonyl group, a butylcarbonyl group)].

A most preferred example of the ring is a 4-methylpiperazin-1-yl group.

Another preferred example of $R^{31}$ is a group represented by the formula (B):

[Formula 25]

(B)

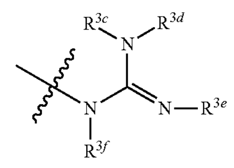

(wherein $R^{3c}$ to $R^{3f}$ are the same as or different from each other and independently represent a hydrogen atom, an alkyl group, or a protecting group for an amino group)

A preferred example of each of $R^{3c}$ to $R^{3f}$ is a hydrogen atom, or a protecting group for an amino group.

$R^{3c}$ is preferably a hydrogen atom.

$R^{3d}$ is preferably a protecting group for an amino group, more preferably an alkoxycarbonyl group, a haloalkoxycarbonyl group, or a cyanoalkoxycarbonyl group, particularly preferably a ($C_{1-4}$-alkoxy)carbonyl group, a ($C_{1-4}$-haloalkoxy)carbonyl group, or a ($C_{1-4}$-cyanoalkoxy)carbonyl group.

$R^{3e}$ is preferably a protecting group for an amino group, more preferably an alkoxycarbonyl group, a haloalkoxycarbonyl group, or a cyanoalkoxycarbonyl group, particularly preferably a ($C_{1-4}$-alkoxy)carbonyl group, a ($C_{1-4}$-haloalkoxy)carbonyl group, or a ($C_{1-4}$-cyanoalkoxy)carbonyl group.

$R^{3f}$ is preferably a hydrogen atom.

A most preferred example of $R^{31}$ is a group selected from the members in the following group:

[Formula 26]

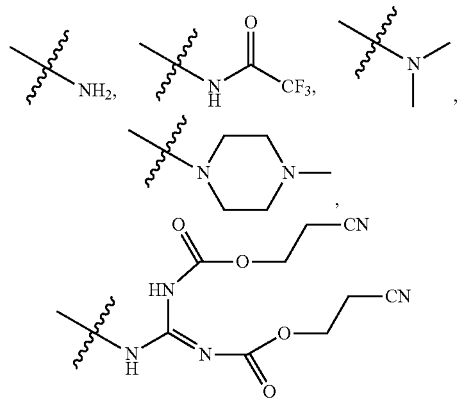

A preferred example of X is an alkylene group, or a group having such a structure that at least one of methylene group moieties other than a methylene group moiety bound to a nitrogen atom and a methylene group moiety bound to $R^{31}$ in the alkylene group is replaced by $—N(R^{32})—$ (wherein $R^{32}$ represents a hydrogen atom or an alkyl group), —O—, or $—S(=O)_k—$ (wherein k represents 0, 1 or 2). Alternatively, a preferred example of X is an alkylene group, or a group having such a structure that $—N(R^{32})—$ (wherein $R^{32}$ is as defined above), —O—, or $—S(=O)_k—$ (wherein k is 0, 1, or 2) is inserted between adjacent two carbon atoms in the alkylene group.

A more preferred example of X is a group selected from the group consisting of:

a group represented by the formula: $—C_mH_{2m}—$ (wherein m represents an integer of 1 to 10);

a group represented by the formula: $—(CH_2)_{m1}—(N(R^{321})—(CH_2)_{m2})_{m3}—$ (wherein $R^{321}$ represents a hydrogen atom or a $C_{1-4}$ alkyl group; m1 represents an integer of 2 to 10; m2 represents an integer of 2 to 4; m3 represents an integer of 1 to 5; and when m3 represents an integer of 2 or more, $R^{321}$'s may be the same as or different from each other and m2's may be the same as or different from each other);

a group represented by the formula: $—(CH_2)_{m4}—(O—(CH_2)_{m5})_{m6}—$ (wherein m4 represents an integer of 2 to 10; m5 represents an integer of 2 to 4; m6 represents an integer of 1 to 5; when m6 represents an integer of 2 or more, m5's may be the same as or different from each other); and a group represented by the formula: $—(CH_2)_{m7}—(S—(CH_2)_{m8})_{m9}—$ (wherein m7 represents an integer of 2 to 10; m8 represents an integer of 2 to 4; m9 represents an integer of 1 to 5; and when m9 represents an integer of 2 or more, m8's may be the same as or different from each other).

A most preferred example of X is a group selected from the group consisting of:

a group represented by the formula: $—(CH_2)_{m10}—$ (wherein m10 represents an integer of 1 to 6);

a group represented by the formula: $—C_2H_4—(N(R^{322})—C_2H_4)_{m11}—$ (wherein $R^{322}$ represents a hydrogen atom or a $C_{1-4}$ alkyl group; m11 represents an integer of 1 to 5; and when m11 represents an integer of 2 or more, $R^{322}$'s may be the same as or different from each other);

a group represented by the formula: $—C_2H_4—(O—C_2H_4)_{m12}—$ (wherein m12 represents an integer of 1 to 5); and a group represented by the formula: $—C_2H_4—(S—C_2H_4)_{m13}—$ (wherein m13 represents an integer of 1 to 5).

The substituent which can substitute arbitrarily on a carbon atom in the alkylene group is preferably a halogen atom, a hydroxyl group, an alkoxy group, a mercapto group, an alkylthio group, an amino group, a monoalkylamino group, a dialkylamino group, an acyloxy group, an acylamino group or an acylthio group. The number of substituent(s) may vary depending on the number of carbon atoms in the alkylene group, and is for example 1 to 3, preferably 2 or 3.

In one embodiment, it is preferred that $R^3$ represents a group represented by the formula: $R^{31}—X—$, $R^{31}$ represents a group represented by formula (A) or (B), and X represents $—C_mH_{2m}—$ (wherein m represents an integer of 1 to 10).

Preferred examples of $R^4$ include a hydrogen atom and an alkyl group which may have a substituent. The substituent is preferably at least one member selected from the group consisting of a halogen atom, an oxo group, a hydroxyl group, an alkoxy group, an alkylthio group, an alkylamino group and a cyano group. The number of the substituent(s) is preferably 1 to 3.

A more preferred example of $R^4$ is an alkyl group.

A still more preferred example of $R^4$ is a $C_{1-6}$ alkyl group.

A most preferred example of $R^4$ is a $C_{1-4}$ alkyl group.

A preferred example of $R^5$ is at least one member selected from the group consisting of a hydrogen atom and an alkyl group which may have a substituent. The substituent is preferably at least one member selected from the group consisting of a halogen atom, an oxo group, a hydroxyl group, an alkoxy group, an alkylthio group, an alkylamino group and a cyano group. The number of the substituent(s) is preferably 1 to 3.

A more preferred example of $R^5$ is a hydrogen atom or an alkyl group.

A still more preferred example of $R^5$ is a hydrogen atom or a $C_{1-6}$ alkyl group.

A most preferred example of $R^5$ is a hydrogen atom or a $C_{1-4}$ alkyl group.

The compound (1) is preferably a compound (1A) or a compound (1B) shown below:

[Formula 27]

(1A)

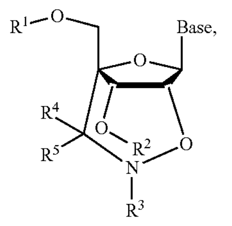

(1B)

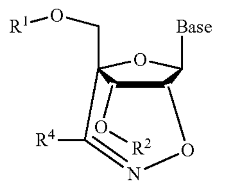

(wherein "Base" and $R^1$ to $R^5$ are as defined above).

The compound (1) is more preferably the compound (1A). In one embodiment, the compound (1A) is preferably a compound (1C) or a compound (1D) shown below:

[Formula 28]

(1C)

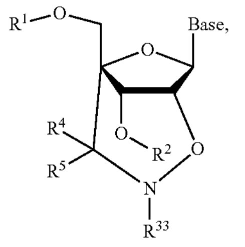

(1D)

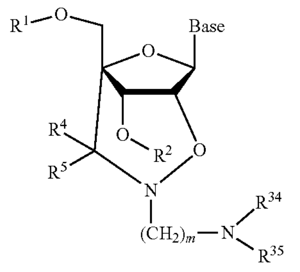

(wherein $R^{33}$ to $R^{35}$ are the same as or different from each other and independently represent a hydrogen atom, an alkyl group, or a protecting group for an amino group; and "Base", $R^1$, $R^2$, $R^4$, $R^5$ and m are as defined above).

In another embodiment, the compound (1A) is preferably a compound (1A) or a compound (1A") shown below:

[Formula 29]

(1A')

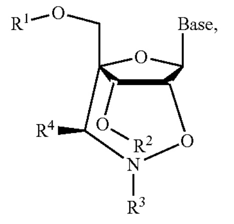

(1A")

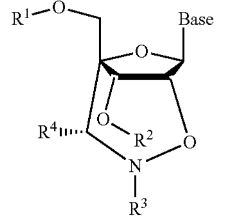

(wherein "Base" and $R^1$ to $R^4$ are as defined above).

The salt may be a pharmaceutically acceptable salt or may not be a pharmaceutically acceptable salt. The salt may be an inorganic salt or an organic salt.

Examples of the salt include an alkali metal salt (e.g., a sodium salt, a potassium salt, a lithium salt), an alkaline earth metal salt (e.g., a calcium salt, a magnesium salt), another metal salt (e.g., an aluminum salt, an iron salt, a zinc salt, a copper salt, a nickel salt, a cobalt salt), an ammonium salt, a tetramethylammonium salt, an amine salt (e.g., a t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzyl-phenethylamine salt, a piperazine salt, a tris(hydroxymethyl)aminomethane salt), an inorganic acid salt (e.g., a hydrofluoric acid salt, a hydrochloric acid salt, a hydrobromic acid salt, a hydroiodic acid salt, a nitric acid salt, a perchloric acid salt, a sulfuric acid salt, a phosphoric acid salt), an organic acid salt (e.g., a methanesulfonic acid salt, a trifluoromethanesulfonic acid salt, an ethanesulfonic acid salt, a benzenesulfonic acid salt, a p-toluenesulfonic acid salt, an acetic acid salt, a malic acid salt, a fumaric acid salt, a succinic acid salt, a citric acid salt, a tartaric acid salt, an oxalic acid salt, a maleic acid salt), and an amino acid salt (e.g., a glycine acid, a lysine acid, an arginine salt, an ornithine salt, a glutamic acid salt, an aspartic acid salt).

<<Method for Producing Compound (1)>>

The compound (1) can be produced by, for example, a reaction scheme 1 shown below. However, the process for the production of the compound (1) is not limited to the reaction scheme 1, and the compound (1) can be synthesized by a combination of known reactions.

Scheme 1

[Formula 30]

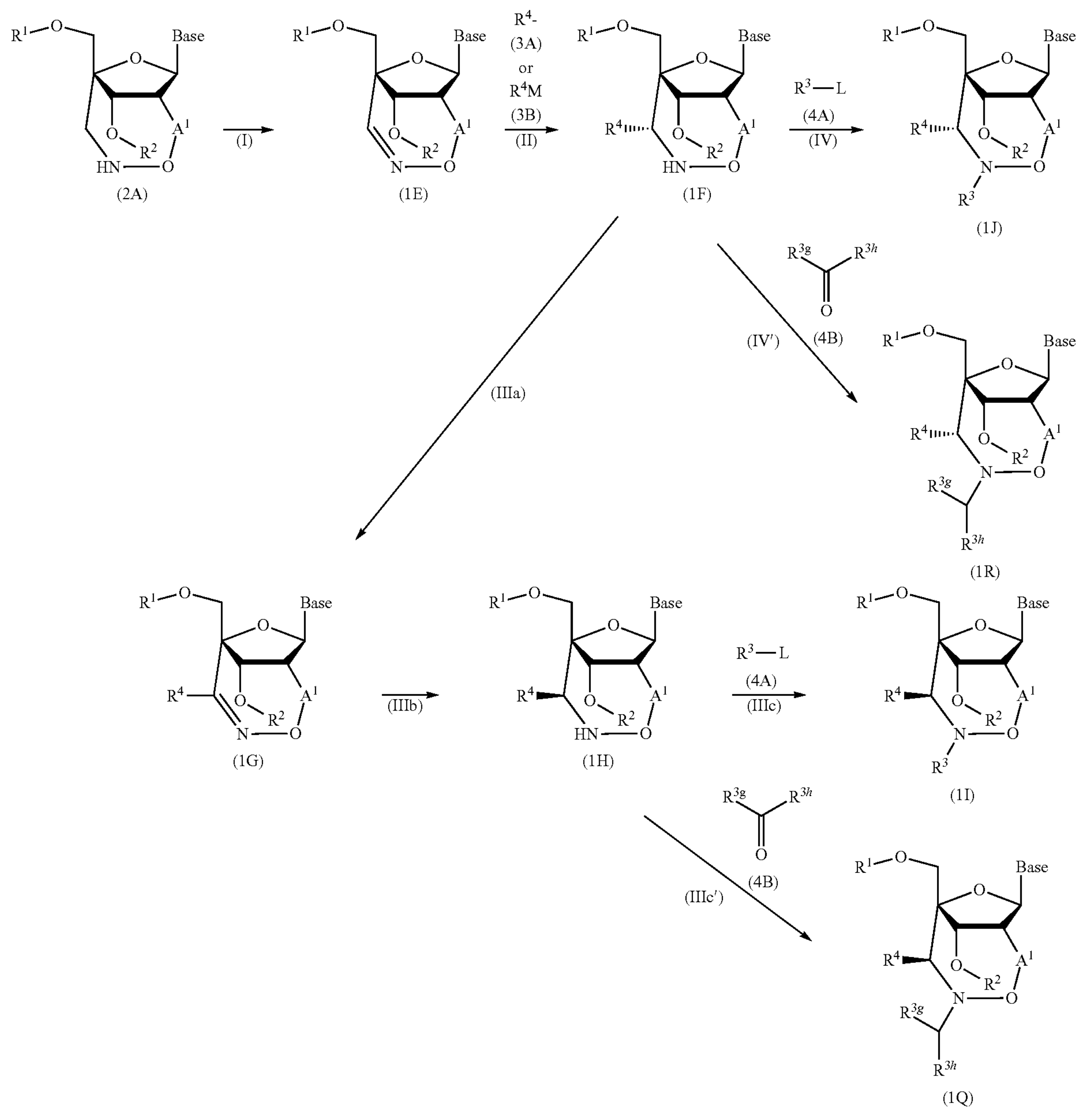

(wherein L represents a leaving group; and "Base", $A^1$, and $R^1$ to $R^4$ are as defined above.)

[Reaction scheme 1]

<Step (I)>

Step (I) is a step of dehydrogenating (oxidizing —$CH_2$—NH— into —CH═N— in) a compound (2A) to produce a compound (1E).

The compound (2A) can be produced by a known method, for example by a method described in US Patent Application Publication No. 2007/167387 (the entire contents of US Patent Application Publication No. 2007/167387 are incorporated herein by reference).

An example of the reagent (oxidizing agent) for the dehydrogenation of the compound (2A) is a hypervalent iodine compound. Examples of the hypervalent iodine compound include (diacetoxyiodo)benzene, (bis(trifluoroacetoxy)iodo)benzene), 2-iodoxybenzenesulfonic acid, 2-iodoxybenzoic acid and Dess-Martin reagent.

The amount of the reagent to be used is generally 0.5 to 6 moles, preferably 1 to 2 moles, relative to 1 mole of the compound (2A).

The dehydrogenation is preferably carried out in the presence of a solvent.

Examples of the solvent include a sulfoxide-type solvent (e.g., dimethyl sulfoxide), a halogen-based solvent (e.g., dichloromethane), and a mixed solvent composed of two or more of these solvents.

The temperature for the dehydrogenation is not particularly limited as long as the reaction can proceed, and is for example 0 to 100° C., preferably 20 to 60° C.

The time for the dehydrogenation is not particularly limited, and is for example 1 to 12 hours, preferably 4 to 6 hours.

<Step (II)>

The step (II) is a step of reacting the compound (1E) with radical represented by formula (3A): $R^4$ (wherein $R^4$ is as defined above) or an organometallic reagent represented by formula (3B): $R^4M$ (wherein M represents a metal atom or an atomic group containing a metal atom; and $R^4$ is as defined above) to produce a compound (1F).

An example of the compound capable of generating the radical (3A) is a compound which can generate ethyl radical in the presence of oxygen (e.g., triethylborane). When $R^4$ is an ethyl group, triethylborane can be used alone. When $R^4$ is a residue other than an ethyl group, triethylborane can be used in combination with a compound represented by the formula: $R^4$-Halo (wherein "Halo" represents a halogen atom).

The amount of the radical (3A) generated in the reaction system is generally 4 to 20 moles, preferably 8 to 12 moles, relative to 1 mole of the compound (1E).

In the compound (3B), examples of M include Li, Na, K, Zn, Cu, Ce, MgCl, MgBr and MgI. In one embodiment, the compound (3B) is preferably Grignard reagent.

The amount of the compound (3B) to be used is generally 1 to 10 moles, preferably 2 to 6 moles, relative to 1 mole of the compound (1E).

The reaction is preferably carried out in the presence of a Lewis acid.

Examples of the Lewis acid include zinc chloride, tin tetrachloride, titanium tetrachloride, boron trifluoride, boron trifluoride diethyl etherate ($BF_3 \cdot OEt_2$), boron trichloride and trimethylsilyl triflate ($(CH_3)_3SiOSO_2CF_3$).

The amount of the Lewis acid to be used is generally 4 to 20 moles, preferably 8 to 12 moles, relative to 1 mole of the compound (1E).

The reaction is preferably carried out in the presence of a solvent.

Examples of the solvent include an aromatic hydrocarbon-type solvent (e.g., toluene, xylene), a halogenated hydrocarbon-type solvent (e.g., dichloromethane), and a mixed solvent composed of two or more of these solvents.

The reaction temperature for the reaction is not particularly limited as long as the reaction can proceed, and is for example −78 to 40° C., preferably 0 to 30° C.

The reaction time for the reaction is not particularly limited, and is for example 0.1 to 2 hours, preferably 0.5 to 1 hour.

<Step (IIIa)>

Step (IIIa) is a step of dehydrogenating (oxidizing —C(H)($R^4$)—NH— into —$CR^4$═N— in) the compound (1F) to produce a compound (1G). The dehydrogenation can be carried out in the same manner as in step (I).

$R^5$ can be introduced by reacting the compound (1G) with radical represented by formula (3C): $R^5\cdot$ (wherein $R^5$ is as defined above) or a compound that is an organometallic reagent represented by formula (3D): RSM (wherein M represents a metal atom or an atomic group containing a metal atom; and $R^4$ is as defined above). This reaction can be carried out by the method described in Organic Letters 1999, 1, 4, 569-572, Tetrahedron Letters 39 (1998) 3237-3240.

<Step (IIIb)>

Step (IIIb) is a step of hydrogenating (reducing —$CR^4$═N— into —C(H)($R^4$)—NH— in) the compound (1G) to produce a compound (1H).

Examples of the reagent (reducing agent) for the hydrogenation of the compound (1G) include diisobutylaluminum hydride, lithium aluminum hydride and sodium borohydride.

The amount of the reagent to be used is generally 1 to 10 moles, preferably 3 to 5 moles, relative to 1 mole of the compound (1G).

The hydrogenation is preferably carried out in the presence of a solvent.

Examples of the solvent include an aromatic hydrocarbon-type solvent (e.g., toluene, xylene), a halogenated hydrocarbon-type solvent (e.g., dichloromethane), and a mixed solvent composed of two or more of these solvents.

The temperature for the hydrogenation is not particularly limited as long as the reaction can proceed, and is for example −20 to −78° C., preferably −60 to −78° C.

The time for the hydrogenation is not particularly limited, and is for example 0.5 to 6 hours, preferably 1 to 3 hours.

<Step (IIIc)>

Step (Mc) is a step of reacting the compound (1H) with a compound represented by formula (4A): $R^3$-L (wherein L represents a leaving group; and $R^3$ is as defined above but does not represent a hydrogen atom) to produce a compound (1I).

In the compound (4A), an example of the leaving group represented by L is a halogen atom (e.g., a chlorine atom, a bromine atom, an iodine atom), an alkylsulfonyloxy group (e.g., a mesyloxy group), a haloalkylsulfonyloxy group (e.g., a trifluoromethylsulfonyloxy group), or an arylsulfonyloxy group (e.g., a tosyloxy group).

The amount of the compound (4A) to be used is generally 1 to 8 moles, preferably 1 to 4 moles, relative to 1 mole of the compound (1H).

The reaction is preferably carried out in the presence of a solvent.

Examples of the solvent include an ether-type solvent (e.g., tetrahydrofuran), a nitrile-type solvent (e.g., acetonitrile), an aromatic hydrocarbon-type solvent (e.g., toluene, xylene), and a mixed solvent composed of two or more of these solvents. Among these solvents, an aromatic hydrocarbon-type solvent is preferred, and at least one solvent selected from the group consisting of toluene and xylene is more preferred.

The reaction is preferably carried out in the presence of a base.

Examples of the base include an inorganic base [e.g., a carbonate salt of an alkali metal (e.g., sodium carbonate, cesium carbonate), a hydrogen carbonate salt of an alkali metal (e.g., sodium hydrogen carbonate), a carbonate salt of an alkaline earth metal (e.g., calcium carbonate), a hydroxide of an alkali metal (e.g., sodium hydroxide, potassium hydroxide), a hydroxide of an alkaline earth metal (e.g., calcium hydroxide), a metal alkoxide (e.g., sodium methoxide, sodium ethoxide)], an organic base [e.g., a tertiary amine (e.g., trialkylamine), a cyclic amine (e.g., 4-(dimethylamino)pyridine, diazabicycloundecene (DBU), diazabicyclononene (DBN))], and a combination of two or more of these bases. Among these bases, a tertiary amine is preferred, and a tri-$C_{1-4}$-alkylamine is more preferred.

The amount of base to be used is generally 2 to 10 moles, preferably 5 to 8 moles, relative to 1 mole of the compound (2A).

The reaction temperature for the reaction is not particularly limited as long as the reaction can proceed, and is for example 30 to 150° C., preferably 50 to 120° C.

The reaction time for the reaction is not particularly limited, and is for example 1 to 24 hours, preferably 1 to 12 hours.

A compound (1Q) wherein $R^3$ is a methyl group which may have one or two substituents can be produced by, for example, a method including the following step (Mc).

<Step (IIIc')>

Step (Mc') is a step of reacting the compound (1H) with a carbonyl compound represented by formula (4B): $R^{3g}$—C(═O)—$R^{3h}$ (wherein each of $R^{3g}$ and $R^{3h}$ is a residue of $R^3$) to produce the compound (1Q).

The amount of the compound (4B) to be used is generally 1 to 6 moles, preferably 1 to 3 moles, relative to 1 mole of the compound (1H).

The reaction is preferably carried out in the presence of a reducing agent.

Examples of the reducing agent include sodium borohydride, sodium cyanoborohydride, lithium cyanoborohydride, lithium triethylborohydride, lithium tri(sec-butyl)borohydride, potassium tri(sec-butyl)borohydride, sodium triacetoxyborohydride, lithium aluminium hydride, sodium bis(2-methoxyethoxy)aluminum dihydride, and combinations thereof.

The amount of the reducing agent to be used is generally 1 to 8 moles, preferably 1 to 4 moles, relative to 1 mole of the compound (1H).

The reaction is preferably carried out in the presence of an acid catalyst. Examples of the acid catalyst include pyridinium p-toluenesulfonate (PPTS), acetic acid and hydrochloric acid.

The reaction is preferably carried out in the presence of a solvent. Examples of the solvent include an alcohol-type solvent (e.g., methanol), an ether-type solvent (e.g., tetrahydrofuran), and a mixed solvent composed of two or more of these solvents.

The reaction temperature for the reaction is not particularly limited as long as the reaction can proceed, and is for example 0 to 100° C., preferably 0 to 40° C.

The reaction time for the reaction is not particularly limited, and is for example 0.5 to 12 hours, preferably 1 to 4 hours.

A compound (1I) wherein $R^3$ is a group represented by the formula: $R^{31}$—X— can be produced by, for example, a method including the following steps (IIId) to (IIIf):

(IIId): a step of reacting the compound (1H) with a compound represented by formula (4C):

[Formula 31]

(4C)

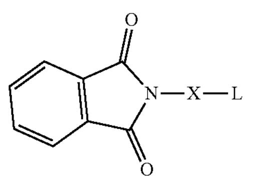

(wherein X and L are as defined above)

to produce a compound represented by formula (1H'):

[Formula 32]

(1H')

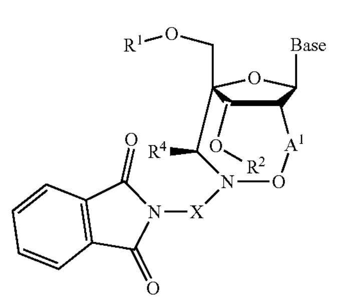

(wherein "Base", $A^1$, $R^1$, $R^2$, $R^4$, and X are as defined above);

(IIIe): a step of reacting the compound (1H') with a hydrazine compound to produce a compound represented by formula (1H"):

[Formula 33]

(1H")

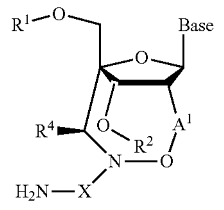

and (IIIf): a step of optionally protecting an amino group in the compound (1H") by a protecting group for an amino group or guanidylating the compound (1H").

<Step (IIId)>

The step (IIId) can be carried out in the same manner as in the step (Mc).

<Step (IIIe)>

The amount of the hydrazine compound to be used is generally 1 to 10 moles, preferably 1.1 to 3.5 moles, relative to 1 mole of the compound (1H').

The reaction is preferably carried out in the presence of a solvent. Examples of the solvent include water, an alcohol-type solvent (e.g., methanol, ethanol), and a mixed solvent composed of two or more of these solvents.

<Step (IIIf)>

As the method for protecting the amino group in the compound (1H") by a protecting group for an amino group, a known or conventional method can be employed. For example, the step of introducing a trifluoromethylcarbonyl group as the protecting group for the amino group in the compound (1H") is a step of reacting the compound (1H") with trifluoroacetic acid or a derivative thereof (e.g., trifluoroacetic anhydride). The reaction is preferably carried out in the presence of a solvent. A preferred example of the solvent is a cyclic amine (e.g., pyridine).

The guanidylation of the compound (1H") is generally carried out by the reaction with a guanidylating agent. Examples of the guanidylating agent include a nitrogen-containing guanidylating agent and a sulfur-containing guanidylating agent.

Examples of the nitrogen-containing guanidylating agent include compounds represented by the following formulae:

[Formula 34]

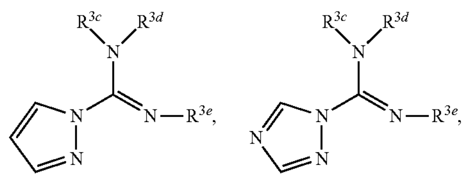

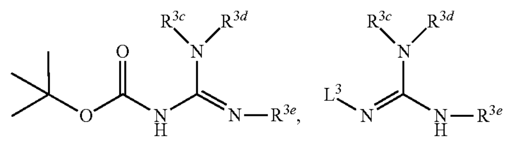

(wherein $L^3$ represents a leaving group; and $R^{3c}$ to $R^{3e}$ are as defined above).

Examples of the leaving group represented by $L^3$ are the same as those of L.

The nitrogen-based guanidinylating agent is preferably 1-amidinopyrazole hydrochloride, 1-carbamimidoyl-1,2,4-triazole hydrochloride, 1-(N-t-butoxy-amidino)pyrazole, 1-(N-benzyloxy-amidino)pyrazole, 1-[N,N'-(di-t-butoxy)amidino]pyrazole, 1-[N,N'-(di-benzyloxy)amidino]pyrazole, 1,2,3-tris(t-butoxycarbonyl)guanidine, or Goodman's reagent.

Examples of the sulfur-containing guanidylating agent include compounds represented by the following formulae:

[Formula 35]

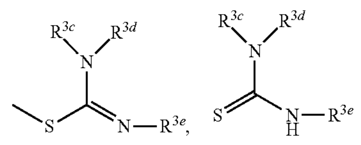

(wherein $R^{3c}$ to $R^{3e}$ are as defined above).

The sulfur-based guanidinylating agent is preferably N,N'-di-t-butoxy-S-methylisothiourea, or 1,3-di-t-butoxythiourea.

The amount of the guanidylating agent to be used is generally 0.5 to 10 moles, preferably 0.8 to 2.0 moles, relative to 1 mole of the compound (1H").

The reaction of the compound (1H") with the guanidylating agent is preferably carried out in the presence of a solvent.

Examples of the solvent include a halogenated hydrocarbon-type solvent (e.g., dichloromethane), an amide-type solvent (e.g., N,N-dimethylformamide, N,N-dimethylacetamide, N-methylpyrrolidone), and a mixed solvent composed of two or more of these solvents. Among these solvents, an amide-type solvent is preferred, and N,N-dimethylformamide is more preferred.

The reaction temperature for the reaction is not particularly limited as long as the reaction can proceed, and is for example 15 to 30° C.

<Step (IV)>

Step (IV) is a step of reacting the compound (1F) with a compound (4A) to produce a compound (1J). This reaction can be carried out in the same manner as in the step (Mc). A compound (1J) wherein $R^3$ is a group represented by the formula: $R^{31}$—X— can be produced by, for example, a method including steps similar to the steps (IIId) to (IIIf).

<Step (IV')>

Step (IV) is a step of reacting the compound (1F) with a compound (4B) to produce a compound (1R). This step can be carried out in the same manner as in the step (IIIc').

The "Base" in each of the compounds (1), (1A) to (1J), (1Q), (1R) and (2A) can be converted by, for example, a reaction scheme 2 shown below.

Scheme 2

[Formula 36]

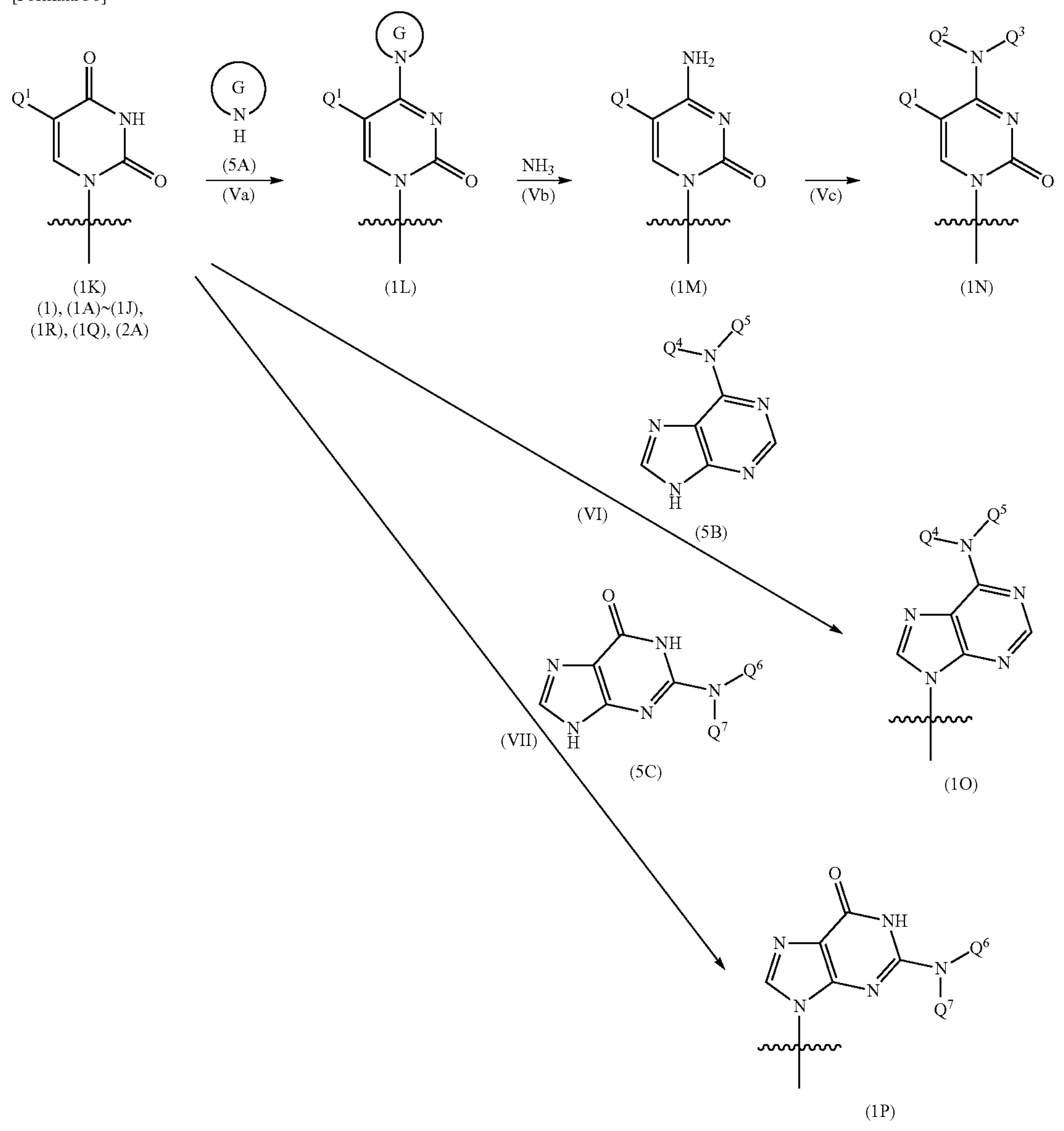

(1K)
(1), (1A)~(1J),
(1R), (1Q), (2A)
(1L)
(1M)
(1N)
(5B)
(5C)
(1O)
(1P)

(wherein $Q^1$ represents a hydrogen atom or a substituent; $Q^2$ and $Q^3$ are the same as or different from each other and independently represent a hydrogen atom or a protecting group for an amino group (provided that $Q^2$ and $Q^3$ do not represent hydrogen atoms coincidentally); $Q^4$ to $Q^7$ are the same as or different from each other and independently represent a hydrogen atom or a protecting group for an amino group; and the ring G represents a 5- or 6-membered nitrogenated heterocyclic ring).

[Reaction Scheme 2]

<Step (V)>

Step (V) is a step of converting the "Base" from "a 2,4-dioxo-1,2,3,4-tetrahydropyrimidin-1-yl group which may have a substituent" to "a 2-oxo-1,2-dihydropyrimidin-1-yl group which may have a substituent" in each of the compounds (1), (1A) to (1J), (1Q), (1R) and (2A), and includes step (Va) to step (Vc).

<Step (Va)>

Step (Va) is a step of reacting a compound (1K) wherein "Base" represents "a 2,4-dioxo-1,2,3,4-tetrahydropyrimidin-1-yl group which may have a substituent" with a compound represented by formula (5A) and a phosphoric acid halide to produce a compound (1L).

In the compound (1K), $Q^1$ is preferably a hydrogen atom or an alkyl group, more preferably a hydrogen atom or a $C_{1-4}$ alkyl group.

The compound (5A) is preferably a 5-membered nitrogenated heterocyclic ring compound, more preferably triazole.

The amount of the compound (5A) to be used is generally 5 to 20 moles, preferably 7 to 9 moles, relative to 1 mole of the compound (1K).

The phosphoric acid halide is preferably phosphoric trichloride.

The amount of the phosphoric acid halide to be used is generally 1 to 5 moles, preferably 1 to 3 moles, relative to 1 mole of the compound (1K).

The reaction is preferably carried out in the presence of a solvent.

Examples of the solvent include a nitrile-type solvent (e.g., acetonitrile), an ether-type solvent (e.g., tetrahydrofuran), a halogen-based solvent (e.g., a haloalkane), and a mixed solvent composed of two or more of these solvents. Among these solvents, a nitrile-type solvent (e.g., acetonitrile) is preferred.

The reaction is preferably carried out in the presence of a base.

Examples of the base include an inorganic base [e.g., a carbonate salt of an alkali metal (e.g., sodium carbonate, cesium carbonate), a hydrogen carbonate salt of an alkali metal (e.g., sodium hydrogen carbonate), a carbonate salt of an alkaline earth metal (e.g., calcium carbonate), a hydroxide of an alkali metal (e.g., sodium hydroxide, potassium hydroxide), a hydroxide of an alkaline earth metal (e.g., calcium hydroxide), a metal alkoxide (e.g., sodium methoxide, sodium ethoxide)], an organic base [e.g., a tertiary amine (e.g., trialkylamine), a cyclic amine (e.g., 4-(dimethylamino)pyridine, diazabicycloundecene (DBU), diazabicyclononene (DBN))], and a combination of two or more of these bases. Among these bases, a tertiary amine is preferred, and a tri-$C_{1-4}$-alkylamine is more preferred.

The amount of base to be used is generally 5 to 20 moles, preferably 10 to 15 moles, relative to 1 mole of the compound (1K).

The reaction temperature for the reaction is not particularly limited as long as the reaction can proceed, and is for example −5 to 10° C.

For example, as the reaction, the method described in the description of U.S. Pat. No. 5,359,067 may be employed.

<Step (Vb)>

Step (Vb) is a step of reacting the compound (1L) with ammonia to produce a compound (1M).

The amount of ammonia to be used is generally 5 to 100 moles, preferably 20 to 50 moles, relative to 1 mole of the compound (1L).

The reaction is preferably carried out in the presence of a solvent.

Examples of the solvent include an amide-type solvent (e.g., N,N-dimethylformamide, N,N-dimethylacetamide, N-methylpyrrolidone), an ether-type solvent (e.g., a cyclic ether such as tetrahydrofuran and dioxane), and a mixed solvent composed of two or more of these solvents. Among these solvents, an ether-type solvent is preferred, and a cyclic ether is more preferred, and at least one solvent selected from tetrahydrofuran and dioxane is still more preferred.

The reaction temperature for the reaction is not particularly limited as long as the reaction can proceed, and is for example 15 to 30° C.

<Step (Vc)>

Step (Vc) is a step of protecting an amino group in the compound (1M) by a protecting group to produce a compound (1N). As the method for protecting the amino group by the protecting group, a known method (for example, the method described in the description of US Patent Application Publication No. 2007/167387) or a conventional method may be employed.

<Step (VI)>

Step (VI) is a step of converting the "Base" from "a 2,4-dioxo-1,2,3,4-tetrahydropyrimidin-1-yl group which may have a substituent" to "a purin-9-yl group which may have a substituent" in each of the compounds (1), (1A) to (1J), (1Q), (1R) and (2A).

More specifically, step (VI) is a step of reacting the compound (1K) wherein "Base" is "a 2,4-dioxo-1,2,3,4-tetrahydropyrimidin-1-yl group which may have a substituent" with a compound represented by formula (5B) to produce a compound (1O).

The amount of the compound (5B) to be used is generally 1 to 5 moles, preferably 1 to 3 moles, relative to 1 mole of the compound (1K).

The reaction is preferably carried out in the presence of a Lewis acid.

An example of the Lewis acid is trimethylsilyl trifluoromethanesulfonate.

The amount of the Lewis acid to be used is generally 0.5 to 5 moles, preferably 1 to 3 moles, relative to 1 mole of the compound (1K).

The reaction is preferably carried out in the presence of a silylating agent.

Examples of the silylating agent include N,O-bis(trimethylsilyl)acetamide (BSA), N,O-bis-silyltrifluoroacetamide (BSTFA), hexamethyldisilazane (HMD), N,O-bis-tert-butyldimethylsilylacetamide, N-(trimethylsilyl)diethylamine, N-(trimethyl silyl)dimethylamine, N-methoxy-N,O-bis(trimethylsilyl)carbamate, N-methyl-N-trimethyl silylacetamide, N-methyl-N-trimethylsilylheptafluorobutyramide, N-methyl-N-trimethylsilyltrifluoroacetamide, N-trimethylsilylacetamide, and a combination of two or more of these compounds. Among these compounds, N,O-bis(trimethylsilyl)acetamide (BSA) is preferred.

The amount of the silylating agent to be used is generally 1 to 20 moles, preferably 3 to 8 moles, relative to 1 mole of the compound (1K).

The reaction temperature for the reaction is not particularly limited as long as the reaction can proceed, and is for example 30 to 150° C., preferably 50 to 120° C.

As the reaction, the method described in, for example, US Patent Application Publication No. 2012/071646 may be employed (the entire contents of US Patent Application Publication No. 2012/071646 are incorporated herein by reference).

<Step (VII)>

Step (VII) is a step of converting "Base" from "a 2,4-dioxo-1,2,3,4-tetrahydropyrimidin-1-yl group which may have a substituent" to "a 6-oxo-1,6-dihydro-9H-purin-9-yl group which may have a substituent" in each of the compounds (1), (1A) to (1J), (1Q), (1R) and (2A).

More specifically, step (VII) is a step of reacting the compound (1K) wherein "Base" is "a 2,4-dioxo-1,2,3,4-tetrahydropyrimidin-1-yl group which may have a substituent" with a compound represented by formula (5C) to produce a compound (1P).

The reaction can be carried out under the same conditions as those employed in step (VI).

If necessary, the method for producing the compound (1) may further include a step of purifying an intermediate product and a final product by a conventional method, such as concentration, recrystallization and silica gel column chromatography.

<<Composition Containing Compound (1)>>

The composition according to the present invention contains the above-mentioned compound (1).

The composition may contain one compound (1) or two or more compounds (1). For example, the composition may contain one, two, three or four compounds selected from the group consisting of:

- a compound (1) wherein "Base" is a thymin-1-yl group;
- a compound (1) wherein "Base" is a 5-methylcytosin-1-yl group, an N-acetyl-5-methylcytosin-1-yl group, an N-isobutyryl-5-methylcytosin-1-yl group, or an N-benzoyl-5-methylcytosin-1-yl group;
- a compound (1) wherein "Base" is an adenin-9-yl group, an N-acetyl-adenin-9-yl group, an N-isobutyryl-adenin-9-yl group, or an N-benzoyl-adenin-9-yl group; and a compound (1) wherein "Base" is a guanin-9-yl group, an N-acetyl-guanin-9-yl group, an N-isobutyrylguanin-9-yl group, an N-benzoyl-guanin-9-yl group, or an N—(N,N-dimethylformamidyl)-guanin-9-yl group.

An example of the form of the composition is a liquid form.

When the composition has a liquid form, the composition generally contains a solvent. As the solvent, a known solvent can be used, and preferred examples of the solvent include a halogenated hydrocarbon-type solvent (e.g., dichloromethane), a nitrile-type solvent (e.g., acetonitrile), an aromatic hydrocarbon-type solvent (e.g., toluene, xylene), water, and a TE buffer. Among these solvents, dichloromethane, toluene, and acetonitrile are more preferably used.

The composition is generally provided to a user in a form packed in a container.

The composition can be used for the below-mentioned synthesis of an oligonucleotide or a salt thereof. The composition can also be used as a pharmaceutical composition.

<<Oligonucleotide or Salt Thereof>

The oligonucleotide or the salt thereof according to the present invention has a unit represented by formula (6):

[Formula 37]

(6)

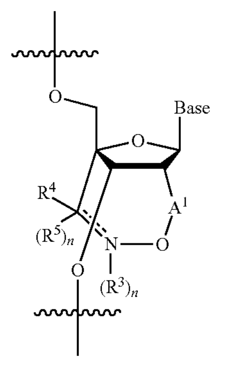

(wherein "Base", $A^1$, $R^3$ to $R^5$ and n are as defined above).

The unit is preferably a unit represented by formula (6a):

[Formula 38]

(6a)

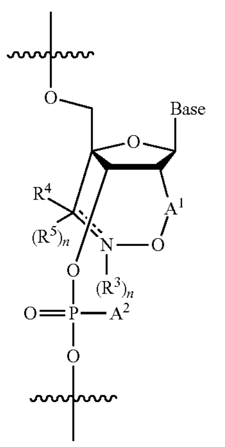

(wherein $A^2$ represents OH, $O^-$, SH or $S^-$; and "Base", $A^1$, $R^3$ to $R^5$ and n are as defined above).

The unit represented by formula (6a) is preferably a unit represented by formula (6a-1) below, more preferably a unit represented by formula (6a-2) or (6a-3) below:

[Formula 39]

(6a-1)

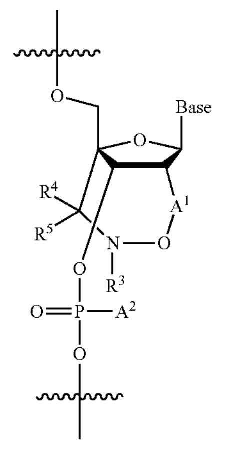

(6a-2)

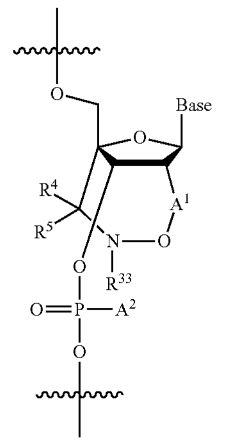

(6a-3)

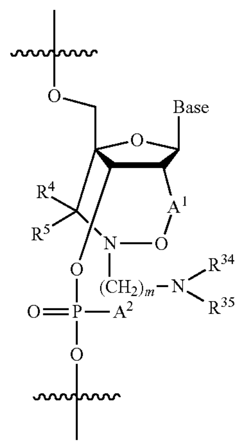

(wherein "Base", $A^1$, $A^2$, $R^3$ to $R^5$, $R^{33}$ to $R^{35}$ and m are as defined above).

Hereinbelow, an oligonucleotide having a unit represented by formula (6) or (6a) or a salt thereof is referred to as an "oligonucleotide (6)".

When the oligonucleotide (6) has at least two units each represented by formula (6) or (6a), the structures of the units may be the same as or different from each other.

The oligonucleotide (6) may further contain another unit, in addition to the unit represented by formula (6) or (6a). An example of the other unit is at least one unit selected from units respectively represented by formulae (7) to (10):

[Formula 40]

(7)

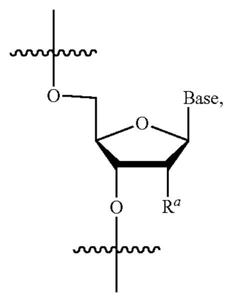

(8)

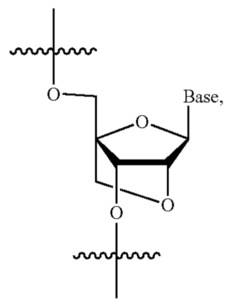

(9)

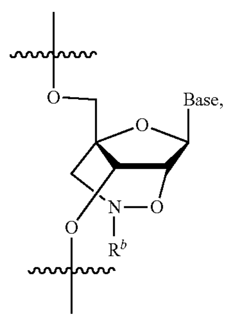

(10)

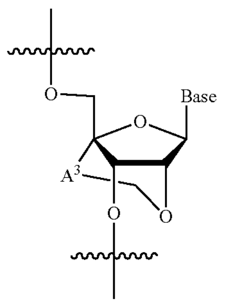

(wherein $A^3$'s are the same as or different from each other and independently represent a single bond or an alkylene group which may have a substituent; $R^a$ represents a hydrogen atom or a hydroxyl group; $R^b$ is the same as $R^3$; and "Base" is as defined above).

The other unit is preferably at least one unit selected from units respectively represented by formulae (7a) to (10a):

[Formula 41]

(7a)

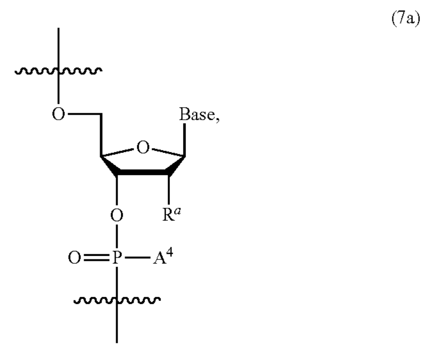

(8a)

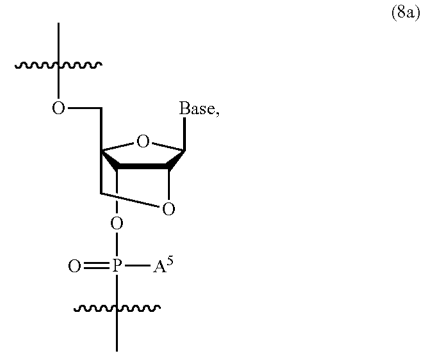

(9a)

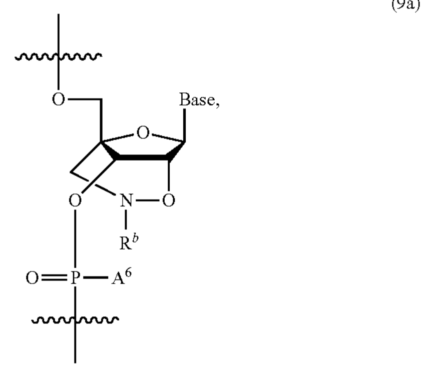

(10a)

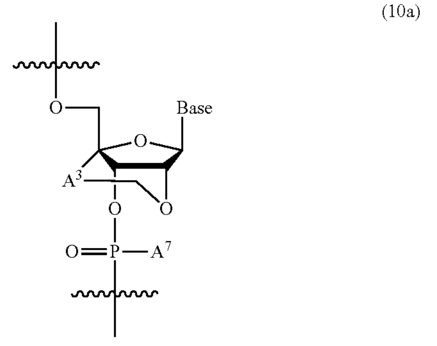

(wherein $A^4$ to $A^7$ are the same as or different from each other and independently represent OH, $O^-$, SH or $S^-$; and "Base", $A^3$, $R^a$ and $R^b$ are as defined above).

For example, the other unit may be a unit derived from any one of the nucleotides described in the descriptions of US Patent Application Publication No. 2003/105309, US Patent Application Publication No. 2017/044528, US Patent Application Publication No. 2006/166908, US Patent Application Publication No. 2012/208991, US Patent Application Publication No. 2015/266917, and US Patent Application Publication No. 2003/207841 (the entire contents of US Patent Application Publication No. 2003/105309, US Patent Application Publication No. 2017/044528, US Patent Application Publication No. 2006/166908, US Patent Application Publication No. 2012/208991, US Patent Application Publication No. 2015/266917, and US Patent Application Publication No. 2003/207841 are incorporated herein by reference).

The nucleotide sequence for the oligonucleotide (6) is not particularly limited, as long as the nucleotide sequence is complementary to (the full length or a part of) the nucleotide sequence for target DNA or target RNA.

The length of the oligonucleotide (6) is not particularly limited, and can be selected depending on the length of the nucleotide sequence for a target. The lower limit of the length of the oligonucleotide (6) is, for example 5-mer, preferably 10-mer, more preferably 15-mer, and the upper limit of the length of the oligonucleotide (6) is, for example 200-mer, preferably 100-mer, more preferably 50-mer, still more preferably 30-mer. The length of the oligonucleotide (6) is, for example 5- to 200-mer, preferably 5- to 50-mer, more preferably 10- to 40-mer, more preferably 15- to 30-mer. The binding force of the oligonucleotide (6) to the nucleotide sequence for a target becomes stronger with the increase in the length of the oligonucleotide (6).

In the oligonucleotide (6), the ratio of the number of the units represented by formula (6) to the total number of the nucleotide units is not particularly limited, and can be designed appropriately depending on the intended use (e.g., as a primer, a probe, clamp nucleic acid, a medicine).

The oligonucleotide (6) may be in the form of a salt. In other words, at least one nucleotide unit among the nucleotide units constituting the oligonucleotide (6) may be in the form of a salt. The salt may be a pharmaceutically acceptable salt or may not be a pharmaceutically acceptable salt. The salt may be an inorganic salt or an organic salt. As in the case of the salt exemplified for the compound (1), examples of the salt include an alkali metal salt, an alkaline earth metal salt, another metal salt, an ammonium salt, a tetramethylammonium salt, an amine salt, an inorganic acid salt, an organic acid salt, and an amino acid salt.

The oligonucleotide (6) may be modified with a labeling substance. The labeling substance is not particularly limited, and may be a substance known in the art as a label to be attached to a nucleic acid, such as a fluorescent substance, a hapten (e.g., biotin, digoxigenin, DNP), and a radioisotope.

The oligonucleotide (6) has high sequence-specificity.

The oligonucleotide (6) has both of a high Tm value for single-stranded DNA and a high Tm value for single-stranded RNA. In other words, the oligonucleotide (6) binds strongly to single-stranded DNA and single-stranded RNA, and has high capability of forming a double strand. In particular, the Tm value of the oligonucleotide (6) for single-stranded RNA is extremely high compared with that for the DNA or RNA represented by formula (7).

The oligonucleotide (6) can be utilized suitably as a probe for examining the nucleotide sequence for single-stranded RNA or single-stranded DNA or for detecting single-stranded RNA or single-stranded DNA in a highly sequence-selective manner.

The oligonucleotide (6) is less likely to be decomposed with a nuclease, and therefore can be present in a living body for a long period after the administration to the living body. For example, the oligonucleotide (6) can form a double strand with sense RNA to inhibit the transcription of mRNA for a biological component (a protein) that may cause a disease. The oligonucleotide (6) can also inhibit the proliferation of a virus that has infected.

The oligonucleotide (6) is useful as a medicine which can inhibit the activity of a gene to treat a disease, e.g., an anti-tumor agent and anti-viral agent.

The oligonucleotide (6) also has a stable and excellent activity for use as an antisense or anti-gene or an aptamer, or has an excellent activity for use as a detecting drug for a specific gene or a primer for the initiation of the amplification of a specific gene.

The oligonucleotide (6) is useful as a physiological/bioactive substance, a material for a medicine, a functional material for a double-stranded oligonucleotide for use in an RNA interference method, a decoy method or the like, a functional material such as a DNA chip that targets a single-stranded nucleic acid (e.g., cDNA), a molecular beacon or the like, a functional material for use in various antisense methods (including a ribozyme or a DNA-zyme), anti-gene methods or genetic homologous recombination methods, a material which can be used in combination with a fluorescence or a light-emitting substance in a highly sensitive analysis of a biological trace component, or a material for use in the development of a reagent for research use (e.g., the elucidation of the function of a gene).

<<Method for Producing Oligonucleotide (6)>>

The oligonucleotide (6) can be synthesized in accordance with a conventional method such as a phosphoramidite protocol.

For example, the method for producing the oligonucleotide (6) includes:

(I) a step of reacting a compound represented by formula (6B):

[Formula 42]

(6B)

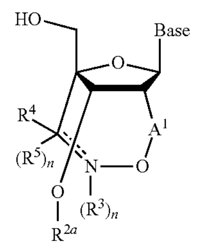

(wherein $R^{2a}$ represents an alkyl group which may have a substituent, an alkenyl group which may have a substituent, a cycloalkyl group which may have a substituent, a cycloalkenyl group which may have a substituent, an aryl group which may have a substituent, a protecting group for a hydroxyl group, a phosphino group which has a substituent, a dihydroxyphosphinyl group which may have a substituent, or a hydroxymercaptophosphinyl group which may have a substituent; and "Base", $A^1$, $R^3$ to $R^5$ and n are as defined above)

or a salt thereof with at least one compound or salt selected from compounds respectively represented by formulae (6C) to (10C):

[Formula 43]

(6C)

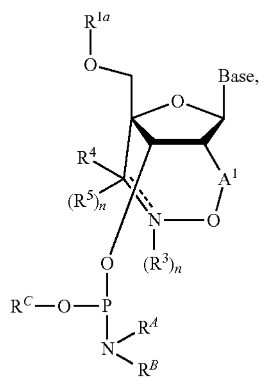

(7C)

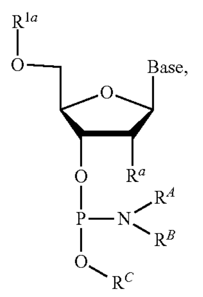

(8C)

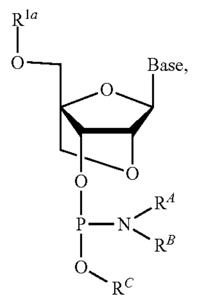

(9C)

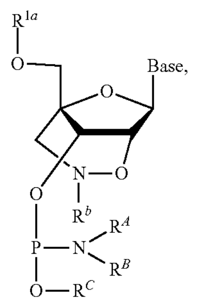

(10C)

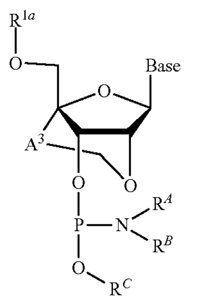

(wherein $R^{1a}$ represents a hydrogen atom, an alkyl group which may have a substituent, an alkenyl group which may have a substituent, a cycloalkyl group which may have a substituent, a cycloalkenyl group which may have a substituent, an aryl group which may have a substituent, a protecting group for a hydroxyl group, a phosphino group which has a substituent, a dihydroxyphosphinyl group which may have a substituent, or a hydroxymercaptophosphinyl group which may have a substituent;

$R^A$ and $R^B$ are the same as or different from each other and independently represent a hydrogen atom or an alkyl group;

$R^C$ represents a hydrogen atom, an alkyl group, a haloalkyl group, or a cyanoalkyl group; and "Base", $A^1$, $A^3$, $R^3$ to $R^5$, n, $R^a$ and $R^b$ are as defined above)

or salts thereof; and/or (II) a step of reacting a compound represented by formula (6C):

[Formula 44]

(6C)

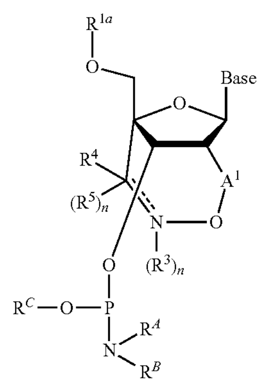

"Base", $A^1$-1a, $R^3$ to $R^5$, n and $R^A$ to $R^C$ are as defined above)

or a salt thereof with at least one compound or salt selected from compounds respectively represented by formulae (6B) to (10B):

[Formula 45]

(6B)

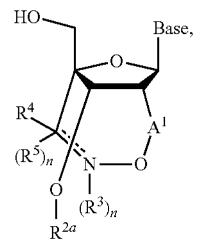

(7B)

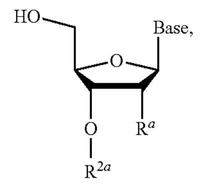

-continued (8B)

(9B)

(10B)

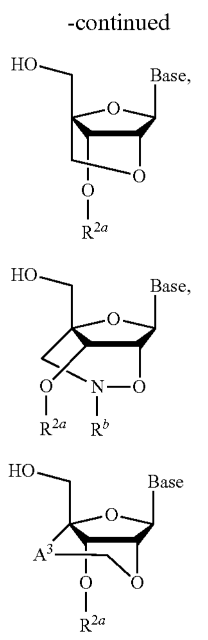

(wherein "Base", $A^1$, $A^3$, $R^{2a}$, $R^3$ to $R^5$, n, $R^a$ and $R^b$ are as defined above)

or salts thereof; and (III) a step of oxidizing (particularly oxidizing a phosphorus atom in) the compound produced in step (I) and/or step (II).

If necessary, the method for producing the oligonucleotide (6) optionally includes a step of purifying the intermediate product and the final product by a conventional method, e.g., concentration, recrystallization, silica gel column chromatography, gel filtration, ethanol precipitation, preparative HPLC.

<<Composition Containing Oligonucleotide (6)>>

The composition according to the present invention contains the above-mentioned oligonucleotide (6).

The composition may contain only one oligonucleotide (6) or may contain two or more oligonucleotides (6).

Examples of the form of the composition include a liquid form and a solid form.

When the composition has a liquid form, the composition generally contains a solvent. As the solvent, a known solvent can be used, and preferably a halogenated hydrocarbon-type solvent (e.g., dichloromethane), a nitrile-type solvent (e.g., acetonitrile), an aromatic hydrocarbon-type solvent (e.g., toluene, xylene) or water is used. Among these solvents, water is more preferred, water containing a buffer (a buffer solution) is more preferred. Examples of the buffer include tris(hydroxymethyl)aminomethane (Tris buffer solution), tris(hydroxymethyl)aminomethane-hydrochloric acid (Tris-HCl buffer solution), tris(hydroxymethyl)aminomethane-EDTA (TE buffer solution), sodium phosphate, 2-morpholinoethanesulfonic acid (IVIES), N-(2-acetamido) iminodiacetic acid (ADA), piperazine-1,4-bis(2-ethanesulfonic acid), N-(2-acetamido)-2-aminoethanesulfonic acid (ACES), cholamine chloride, N,N-bis(2-hydroxyethyl)-2-aminoethanesulfonic acid (BES), N-tris(hydroxymethyl)methyl-2-aminoethanesulfonic acid (TES), 2-[4-(2-hydroxyethyl)-1-piperazinyl]ethanesulfonic acid (HEPES), acetaminoglycine, tricine, glycinamide, and bicine.

The composition may further contain a salt. The salt includes a metal chloride, and examples of the metal chloride include NaCl, $MgCl_2$, and KCl.

The composition may further contain an additive and a co-solvent. For example, dimethyl sulfoxide (DMSO), glycerol, formamide, bovine serum albumin, ammonium sulfate, polyethylene glycol (PEG), gelatin, and a nonionic surfactant may be contained. Examples of the nonionic surfactant include Tween20 (registered tradename) and Triton X-100 (registered tradename).

When the composition has a solid form, the composition may have, for example, such a form that the oligonucleotide (6) is supported on a solid support. Examples of the solid support include an inorganic material and an organic material which can support a biopolymer. Preferred examples include a glass (e.g., a porous glass (a CPG)), silica gel, and a resin (e.g., a crosslinked non-swellable polystyrene resin (a HPS)). Among these materials, a HPS and a CPG is more preferred.

The composition is generally provided to a user in a form packed in a container.

The composition can be used for the amplification or detection of a target nucleic acid, strand invasion, RNAi and the like as mentioned below. The composition can also be used as a pharmaceutical composition.

<<Method for Detecting Target Nucleic Acid>>

The present invention includes a method for detecting a target nucleic acid. The method includes:

(I) a step of amplifying the target nucleic acid selectively by a nucleic acid amplification method; and (II) a step of detecting the target nucleic acid that has been amplified in the step (I), It is preferred that the oligonucleotide to be used for the amplification or the detection comprises the oligonucleotide (6).

In the nucleic acid amplification in step (I), a plurality of primer molecules are generally used. At least a portion of the plurality of primer molecules is the oligonucleotide (6). For example, a forward primer that contains the oligonucleotide (6) and a reverse primer that does not contain the oligonucleotide (6) are used.

In the nucleic acid amplification in step (I), a plurality of primer molecules and probe molecules may be used. In this case, at least a portion of the primer molecules and the probe molecules may be the oligonucleotide (6). For example, a forward primer that does not contain the oligonucleotide (6), a reverse primer that does not contain the oligonucleotide (6), and a probe that contains the oligonucleotide (6) are used.

The type of the nucleic acid amplification method is not particularly limited, as long as the target nucleic acid can be amplified selectively. Examples of the nucleic acid amplification method include a PCR method (including, e.g., a hot-start PCR method, a multiplex PCR method, a nested PCR method, a RT-PCR method, a real-time PCR method, a digital PCR method, TaqMan (registered tradename) PCR method, a clamp PCR method), a NASBA method (see the description of U.S. Pat. No. 5,130,238), a TMA method (see the description of U.S. Pat. No. 5,399,491), a TRC method (see the description of US Patent Application Publication No. 2001/0053518), a LAMP method (see the description of U.S. Pat. No. 6,410,278), an ICAN method (see the description of US Patent Application Publication No. 2003/073081), a LCR method (see the description of EP Patent Application No. 320328), and a SDA method (see the description of U.S. Pat. No. 5,455,166).

In one embodiment, the nucleic acid amplification method to be employed in step (I) is preferably a clamp PCR method. In the clamp PCR method, at least a primer and a clamp nucleic acid are used. Either one or both of the primer and the clamp nucleic acid may contain the oligonucleotide (6).

In general, a clamp nucleic acid can clamp a non-target nucleic acid (e.g., a wild-type gene) in a test specimen stronger compared with a target nucleic acid (e.g., a mutant gene) in a test specimen. A target nucleic acid can be amplified selectively by binding a clamp nucleic acid to a non-target nucleic acid stronger to inhibit the amplification of the non-target nucleic acid. For example, for the detection of a mutation in a specific gene, the amplification of a nucleic acid is carried out in the presence of a clamp nucleic acid having a nucleotide sequence absolutely complementary to that of a wild-type gene. As a result, the amplification of the wild-type nucleic acid is inhibited, while the mutant nucleic acid is amplified selectively.

More specifically, for example, when a target site in a target nucleic acid is defined as a mutating site in a mutant gene and a nucleotide sequence containing the mutating site (the target site in the target nucleic acid) is defined as "sequence A", a clamp nucleic acid is absolutely complementary to a nucleotide sequence corresponding to the sequence A in a wild-type gene that is a non-target nucleic acid.

The oligonucleotide (6) has high sequence-selectivity. Therefore, with respect to the oligonucleotide (6), the capability of binding to a nucleotide sequence that is different from the oligonucleotide (6) by at least one nucleotide is extremely weak. The oligonucleotide (6) can bind specifically to an absolutely complementary nucleotide sequence. Furthermore, the oligonucleotide (6) has a high Tm value, and can form a stable double strand. In other words, a clamp nucleic acid containing the oligonucleotide (6) can strongly bind to a non-target nucleic acid specifically to exhibit high clamping capability. The length of the clamp nucleic acid is not particularly limited, and is for example 5- to 30-mer.

The nucleic acid amplification to be employed in step (I) may be a reverse transcription reaction. In the reverse transcription reaction, cDNA is synthesized with a RNA-dependent DNA polymerase by using RNA as a template. The oligonucleotide (6) binds strongly to RNA. Therefore, the reverse transcription reaction from specific RNA in a test specimen can be inhibited by binding the oligonucleotide (6) to the RNA. In this manner, cDNA can be synthesized more specifically from the target RNA. The synthesized cDNA may be further amplified by a PCR method or the like.

The target nucleic acid may be one contained in a test specimen. The test specimen is typically a specimen collected from a living body (wherein the test specimen is also referred to as a "biological specimen", hereinafter). In general, a specimen produced by a pre-treatment such as the removal of contaminants from a specimen collected from a living body, the extraction/purification of nucleic acid and pre-amplification is used. More specifically, blood, plasma, serum, pleural effusion, a broncho-alveolar lavage fluid, bone marrow fluid, lymphatic fluid, a bowel lavage fluid, an excised tissue, a nasopharyngeal swab fluid, saliva, a nasal discharge snot, a sputum and the like can be used. A specimen prepared by subjecting the above-mentioned specimen to a pretreatment as mentioned above is also included in the "biological specimen". The method of the present invention can detect a nucleic acid with very high sensitivity. Therefore, for example, a gene mutation associated with an abnormal cell can be detected using an excised tissue in which both of normal cells and abnormal cells are present in a mixed state. The method of the present invention can be used suitably in a case where the amount of the test specimen is very small or a case where the amount of a nucleic acid in the test specimen is very small. The test specimen is preferably a solution containing a target nucleic acid. When it is intended to detect a target nucleic acid in a cell contained in blood or an excised tissue, the cell may be lysed by a known method. In addition to the biological specimen, a test specimen such as an excrement, sewage water, river water, sea water, soil, and a specimen that is produced by subjecting each of the aforementioned specimens to a pretreatment as mentioned above can be used. Examples of the excrement include urine and feces.

The target nucleic acid may be DNA or RNA, and is preferably DNA. DNA may be cDNA synthesized from RNA by a reverse transcription reaction. The target nucleic acid may be a gene or a specific region on genomic DNA (e.g., a promoter region in a gene). The detection method according to the present invention can be used for the detection of a mutation, a polymorphism or the like in a target site in a target nucleic acid. The detection method according to the present invention can also be used for the determination of an allele. It also becomes possible to detect as to what type of an allele is contained in a test specimen. The detection method according to the present invention can also be used for the detection of methylation. When the detection method according to the present invention is applied after a bisulphite treatment of a target nucleic acid, the presence or absence of methylated cytosine in the target nucleic acid can be detected.

A gene containing a mutation (hereinafter, also referred to as a "mutant gene") has a difference in nucleotide sequence from a wild-type gene, i.e., a mutation. The difference is caused by at least one mutation selected from the group consisting of substitution, insertion, deletion, inversion, duplication and translocation or a combination thereof.

In general, the difference is often associated with the onset (development) and/or therapeutic sensitivity of a specific disease. The term "onset (development)" includes the actual onset (development) of a disease as well as the risk of onset (development) and the like. The term "therapeutic sensitivity" includes the efficacy of a treatment with a drug or the like as well as the level of an adverse side effect. Examples of the disease include, but are not limited to, cancer, a myelodysplastic syndrome and an infectious disease. A preferred example of the disease is cancer.

A preferred example of the gene is ABL/BCR fusion gene, HER2 gene, EGFR gene, c-KIT gene, KRAS gene, BRAF gene, PIK3CA gene, FLT3 gene, MYC gene, MYCN gene, MET gene, BCL2 gene, or EML4/ALK fusion gene.

In step (II), a nucleic acid amplified by a known method can be detected in accordance with the above-mentioned nucleic acid amplification method. For example, the amplification can be detected qualitatively or quantitatively by detecting a fluorescent generated from a reaction solution or the turbidity of a reaction solution.

An example of the method for detecting an amplified target nucleic acid is a nucleotide sequence analysis method. The target nucleic acid can be detected by analyzing the nucleotide sequence of the amplified target nucleic acid using a known sequence analysis device (sequencer).

For example, as the method for detecting the target nucleic acid in a test specimen, the method described in the description of US Patent Application Publication No. 2015/240299 may be employed.

The present invention includes a method for detecting a target nucleic acid in a test specimen, the method comprising a step of reacting a probe containing the oligonucleotide (6) and a label with the test specimen containing the target nucleic acid. Examples of the detection method include in situ hybridization and a microarray.

When in situ hybridization is employed as the detection method, the target nucleic acid in a test specimen (e.g., a cell) can be detected by hybridizing the oligonucleotide (6) that is labeled with a fluorescent dye or the like with the target nucleic acid in the test specimen and then measuring the label.

When a microarray is employed as the detection method, the target nucleic acid can be detected by reacting a microarray onto which a probe containing the oligonucleotide (6) has been immobilized with the test specimen containing the target nucleic acid and then detecting the hybridization between the target nucleic acid and the probe.

As mentioned above, a target nucleic acid in a test specimen can be detected with high sequence selectivity by using the oligonucleotide (6).

<<Kit for Detecting or Selectively Amplifying Target Nucleic Acid>>

A kit for detecting or selectively amplifying a target nucleic acid includes the oligonucleotide (6). The target nucleic acid may be one contained in a test specimen.

In the kit, the oligonucleotide (6) can be used as a primer, a probe and/or a clamp nucleic acid for the amplification and/or detection of a target nucleic acid, as mentioned above. The primer, the probe and/or the clamp nucleic acid can be designed appropriately depending on the types of the nucleotide sequence of a target nucleic acid or a non-target nucleic acid.

A kit according to one embodiment includes a primer and/or a probe. In this case, at least a portion of the primer and the probe may be the oligonucleotide (6).

Figure 2A:
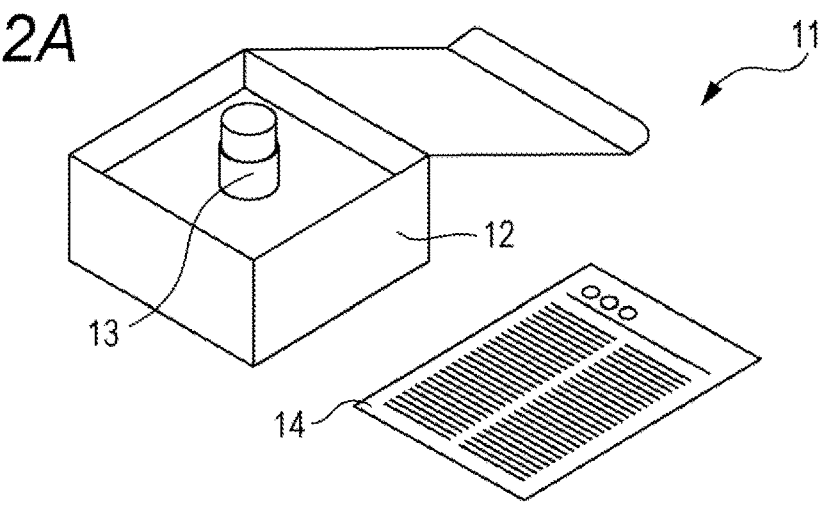
FIG. 2A shows a schematic diagram of one example of a kit that includes a container in which a composition containing a primer and a probe is included.

FIG. 2A shows a schematic diagram of one example of a kit that includes a container in which a composition containing a primer and a probe is included. The kit 11 includes an outer packaging box 12, a container support which is arranged in the outer packaging box 12 and has a depressed part formed on the surface thereof, a container 13 which is installed in the depressed part and in which a composition containing a primer and a probe is included, and a package insert 14. On the package insert 14, a method for handling the kit 11, the conditions for storage of the kit 11, the validity date of the kit 11 and the like can be written.

Figure 2B:
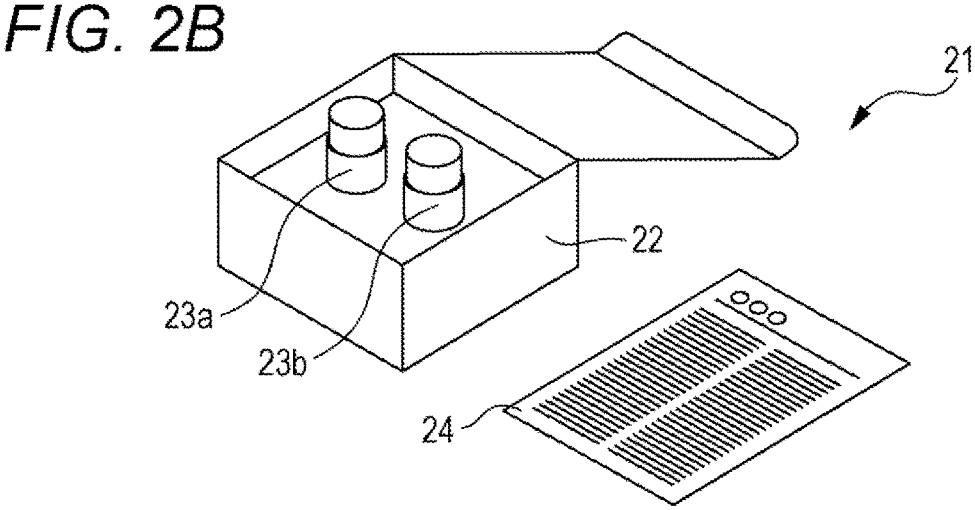
FIG. 2B shows a schematic diagram of one example of a kit that includes both of a container in which a composition containing a primer is included and a container in which a composition containing a probe is included.

FIG. 2B shows a schematic diagram of one example of a kit that includes both of a container in which a composition containing a primer is included a container in which a composition containing a probe is included. The kit 21 includes an outer packaging box 22, a container support which is arranged in the outer packaging box 22 and has a first depressed part and a second depressed part formed apart from each other on the surface thereof along the length direction, a container 23*a* which is installed in the first depressed part and in which a composition containing a primer is included, a container 23*b* which is installed in the second depressed part and in which a composition containing a probe is included, and a package insert 24.

A kit according to another embodiment includes a forward primer, a reverse primer and a probe. At least a portion of them may be the oligonucleotide (6). All of the three components, i.e., the forward primer, the reverse primer and the probe, may be contained in a single container (e.g., a kit shown in FIG. 2A), or any two of them may be contained in a single container (e.g., a kit shown in FIG. 2B), or the three components are contained in different containers separately.

Figure 2C:
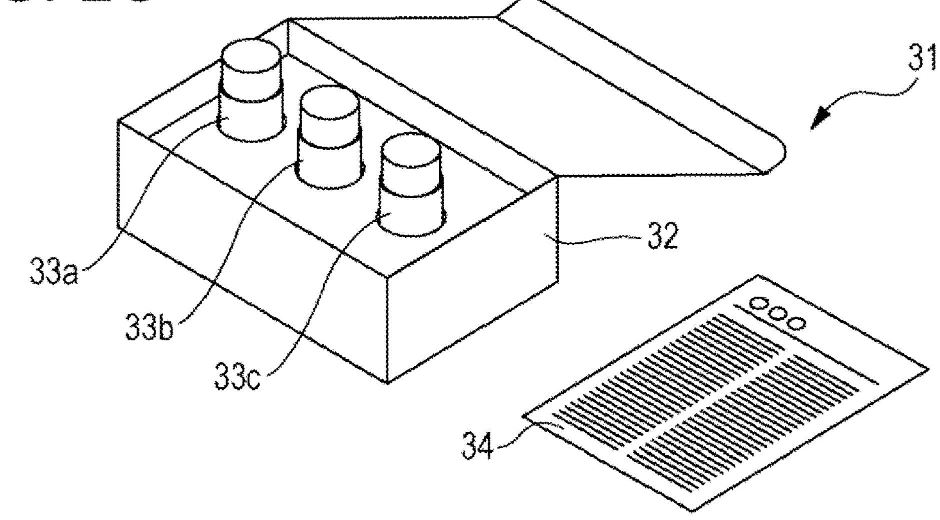
FIG. 2C shows a schematic diagram of one example of a kit that includes a container in which a composition containing a forward primer is included, a container in which a composition containing a reverse primer is included, and a container in which a composition containing a probe is included.

FIG. 2C shows a schematic diagram of one example of a kit that includes a container in which a composition containing a forward primer is included, a container in which a composition containing a reverse primer is included, and a container in which a composition containing a probe is included. The kit 31 includes an outer packaging box 32, a container support which is arranged in the outer packaging box 32 and has first to third depressed parts formed apart from each other on the surface thereof along the length direction, a container 33*a* which is installed in the first depressed part and in which a composition containing the forward primer is included, a container 33*b* which is installed in the second depressed part and in which a composition containing the reverse primer is included, a container 33*c* which is installed in the third depressed part and in which a composition containing the probe is included, and a package insert 34.

A kit according to another embodiment includes a clamp nucleic acid and a primer. At least a portion of them may be the oligonucleotide (6). The kit may be a kit for selectively amplifying a target nucleic acid. A composition containing the clamp nucleic acid and a composition containing the primer may be included in a single container (e.g., a kit shown in FIG. 2A), or may be included in different containers separately (e.g., a kit shown in FIG. 2B).

A kit according to still another embodiment includes a clamp nucleic acid, a primer and a probe. At least a portion of them may be the oligonucleotide (6). All of the three components, i.e., a composition containing the clamp nucleic acid, a composition containing the primer and a composition containing the probe, may be included in a single container (e.g., a kit shown in FIG. 2A), or any two of them may be included in a single container (e.g., a kit shown in FIG. 2B), or the three components are included in different containers separately (e.g., a kit shown in FIG. 2C).

In the kit, a DNA polymerase, deoxynucleoside triphosphates (dNTPs), a reaction buffer, a salt, a restriction enzyme and the like may also be contained.

The present invention includes a use of the oligonucleotide (6) for the detection of a target nucleic acid or the selective amplification of a target nucleic acid. The oligonucleotide (6) to be used in the use has the same characteristic properties as, for example, those of the oligonucleotide (6) included in the kit.

<Pharmaceutical Composition (or Preparation)>

The pharmaceutical composition (or preparation) according to the present invention contains the compound (1) or the oligonucleotide (6). An example of the pharmaceutical composition (or preparation) containing the compound (1) is a low-molecular-weight medicine such as azidothymidine (AZT) that is a nucleoside analogue reversetranscriptase inhibitor: NRTI). An example of the pharmaceutical composition (or preparation) containing the oligonucleotide (6) is a nucleic acid medicine comprising a middle-molecular-weight molecule such as an antisense, siRNA (small interfering RNA), an aptamer, a decoy nucleic acid and a CpG oligonucleotide or a high-molecular-weight molecule.

The pharmaceutical composition may have any dosage form selected from a liquid preparation (e.g., an injection, eye drops, nasal drops, a suspension), a solid preparation (e.g., tables, granules, a powder), a semi-solid preparation (e.g., an ointment, a suppository), and other dosage form known to persons skilled in the art.

Preferred examples of the pharmaceutical composition include preparations for parenteral administration (e.g., a preparation for subcutaneous administration, a preparation for intravenous administration, a preparation of transnasal administration, a preparation for intrathecal administration, a preparation for intraventricular administration, a preparation for intravitreous administration).

Another preferred example of the pharmaceutical composition is a topical preparation.

In general, the pharmaceutical composition further contains a pharmaceutically acceptable carrier or an additive.

The carrier includes a solid carrier and a liquid carrier. Examples of the solid carrier include starch, lactose, calcium sulfate dihydrate, sucrose, talc, gelatin, agar, pectin, gum arabic, magnesium stearate, stearic acid, and atelo collagen. An example of the liquid carrier is water (including physiological saline).

The additive includes a stabilizing agent, and examples of the stabilizing agent include: a para-hydroxybenzoic acid ester such as methylparaben and propylparaben; an alcohol such as benzyl alcohol; and a phenol compound such as phenol and cresol.

The oligonucleotide (6) has high sequence selectivity and a high Tm value, and is therefore less likely to be decomposed with a nuclease. Accordingly, the pharmaceutical composition (or preparation) containing the compound (1) or the oligonucleotide (6) can recognize a target (e.g., a target gene) in vivo with high sequence selectivity and can act on the target.

EXAMPLES

Hereinbelow, the present invention will be described in more detail with reference to examples. However, the present invention is not limited by these examples.

Compound (1) Synthesis Examples

Symbols and abbreviated words used in Synthesis Examples are as follows.

$A^{Bz}$: $N^6$-benzoyladenin
Bz: benzoyl
DMTr: dimethoxytrityl
i-Pr: isopropyl
$BF_3OEt_2$: (boron trifluoride)-(ethyl ether) complex
BSA: N,O-bis(trimethylsilyl)acetamide
CIPS: 1,3-dichloro-1,1,3,3-tetraisopropyldisiloxane
DIBAL-H: diisobutylaluminium hydride
DIPEA: N,N-diisopropylethylamine
DMAP: 4-dimethylaminopyridine
DMF:N,N-dimethylformamide
DMSO: dimethylsulfoxide
DMTrCl: 4,4'-dimethoxytrityl chloride
DBU: 1,8-diazabicyclo[5.4.0]-7-undecene
$Et_3B$: triethylborane
$Et_3N$: triethylamine
MeMgBr: methylmagnesium bromide
MeOH: methanol
$NaBH_3CN$: sodium cyanoborohydride
PPTS: pyridinium p-toluenesulfonate
TBAF: tetra-n-butylammonium fluoride
$Tf_2O$: trifluoromethanesulfonic anhydride
THF: tetrahydrofuran
TMSOTf: trimethylsilyl trifluoromethanesulfonate
TsCl: p-toluenesulfonyl chloride
rt: room temperature
h: hour
min: minute

Synthesis Example 1

A compound (1) wherein "Base" was a thymin-1-yl group, $A^1$ was a single bond, $R^1$ was DMTr, $R^2$ was —P(N(i-Pr)$_2$)($OC_2H_4CN$), $R^3$ was a methyl group, $R^4$ was a methyl group in the R-configuration, $R^5$ was a hydrogen atom and n was 1 (hereinafter, also referred to as "compound (R)M-T-4") was synthesized in accordance with the reaction scheme shown below.

[Formula 46]

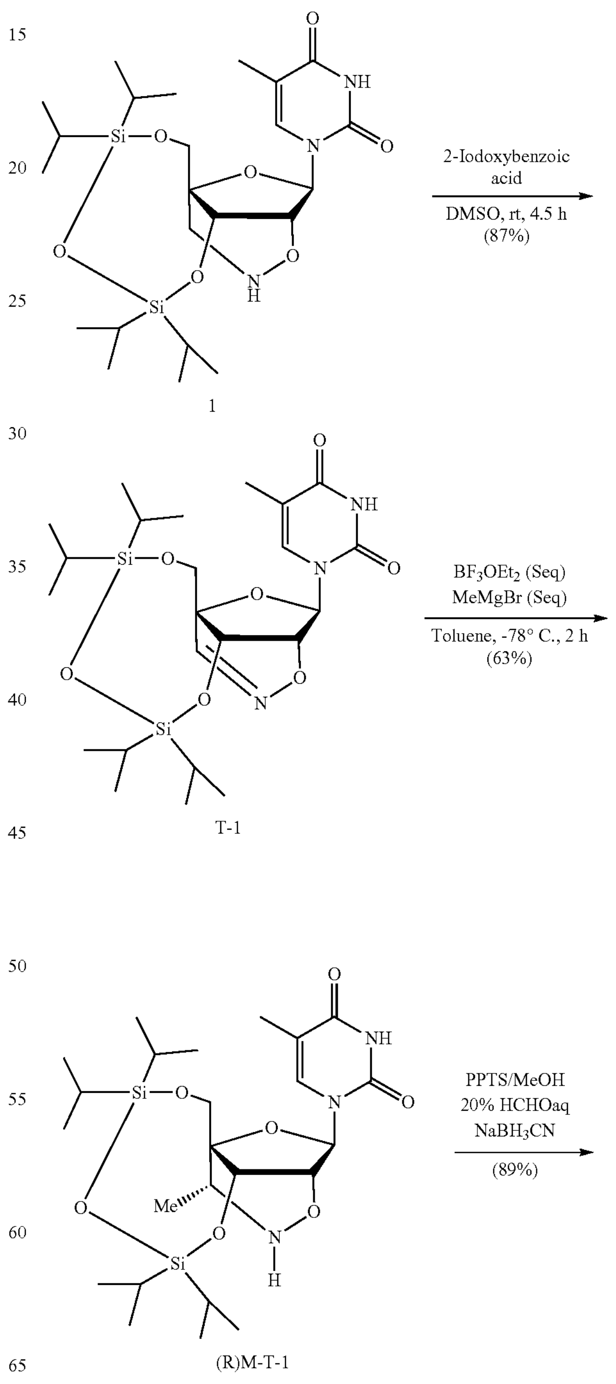

1

T-1

(R)M-T-1

-continued

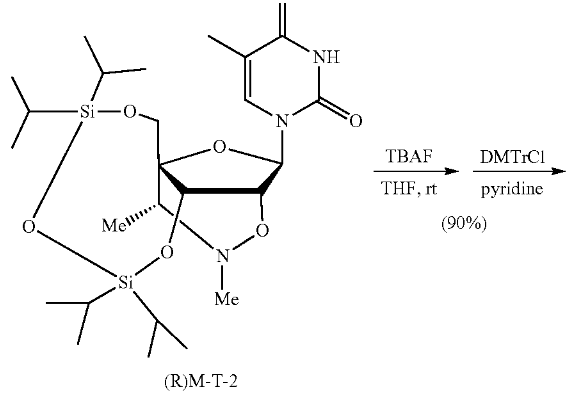

(R)M-T-2

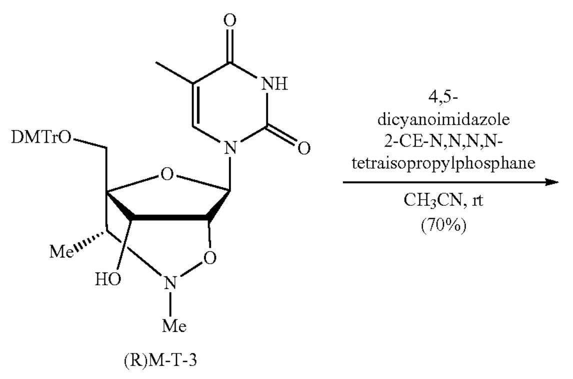

(R)M-T-3

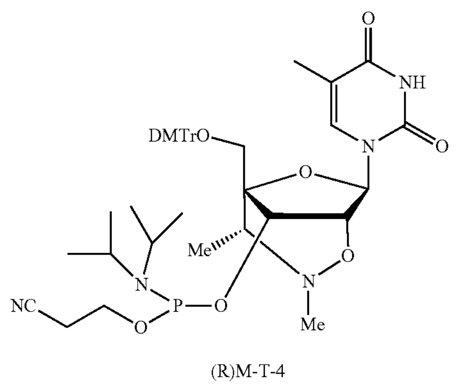

(R)M-T-4

(Synthesis of Compound T-1)

Under a nitrogen stream, the compound 1 (20.0 g, 37.89 mmol) was dissolved in DMSO (500 mL), then 2-iodoxybenzoic acid (27.89 g, 41.68 mmol) was added to the solution at room temperature, and the resultant solution was stirred at room temperature for 4.5 hours. The reaction solution was cooled with water, then the reaction was terminated with a saturated aqueous sodium bicarbonate solution, then the reaction solution was diluted with ethyl acetate and water, and the diluted solution was fractionated into an organic layer and an aqueous layer. The aqueous layer was subjected to back-extraction with ethyl acetate. An organic layer obtained in the first fractionation was combined with an organic layer obtained in the back extraction, then the resultant solution was washed with a saturated aqueous sodium bicarbonate solution and saturated saline in this order, and the washed solution was dried over anhydrous sodium sulfate and was then subjected to distillation under reduced pressure. A crude product thus produced was purified by silica gel column chromatography (hexane:ethyl acetate=3:1 to 2:3) to produce compound T-1 (17.48 g, yield: 87%) as a white foam-like solid substance.

$^1$H NMR ($CDCl_3$) δ 1.01-1.12 (28H, m), 1.91 (3H, d, J=1 Hz), 3.82, 4.15 (2H, ABq, J=14 Hz), 4.44 (1H, m), 4.69 (1H, d, J=4 Hz), 5.86 (1H, s), 7.09 (1H, m), 7.41 (1H, d, J=1 Hz), 8.48 (1H, s).

(Synthesis of Compound (R)M-T-1)

Compound T-1 (3.86 g, 7.33 mmol) was dissolved in toluene (55 mL), then a (boron trifluoride)-(ethyl ether) complex (4.60 mL, 37.0 mmol) was added to the resultant solution under cooling with dry ice/acetone, then methylmagnesium bromide (a 12% solution in tetrahydrofuran) was added dropwise to the reaction solution over 30 minutes, and the resultant solution was stirred for 2 hours while cooling. The reaction was terminated with water, then the reaction solution was diluted with ethyl acetate and saturated saline, and the diluted solution was fractionated to obtain an organic layer. The organic layer thus obtained was washed with saturated saline, and the washed solution was dried over anhydrous sodium sulfate and was then subjected to distillation under reduced pressure. A crude product thus produced was purified by silica gel column chromatography (hexane:ethyl acetate=2:1) to produce compound (R)M-T-1 (2.50 g, 63%) as a white foam-like solid substance.

$^1$H NMR ($CDCl_3$) δ 0.88 (3H, d, J=7), 0.95-1.14 (28H, m), 1.92 (3H, s), 3.67, 4.13 (2H, ABq, J=13), 3.76 (1H, m), 4.15 (1H, d, J=2 Hz), 4.32 (1H, d, J=3), 6.12 (1H, s), 7.74 (1H, s), 8.55 (1H, s).

Alternatively, compound (R)M-T-1 was synthesized in accordance with the reaction scheme shown below.

[Formula 47]

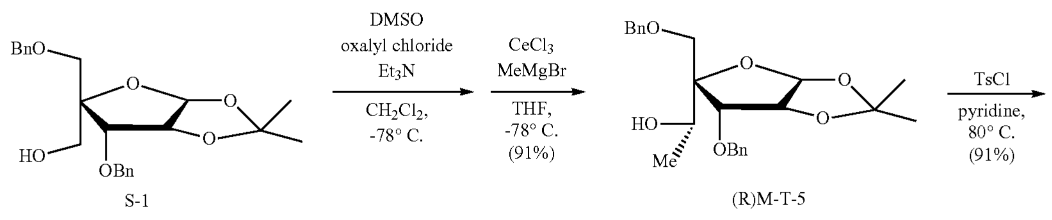

S-1

(R)M-T-5

-continued
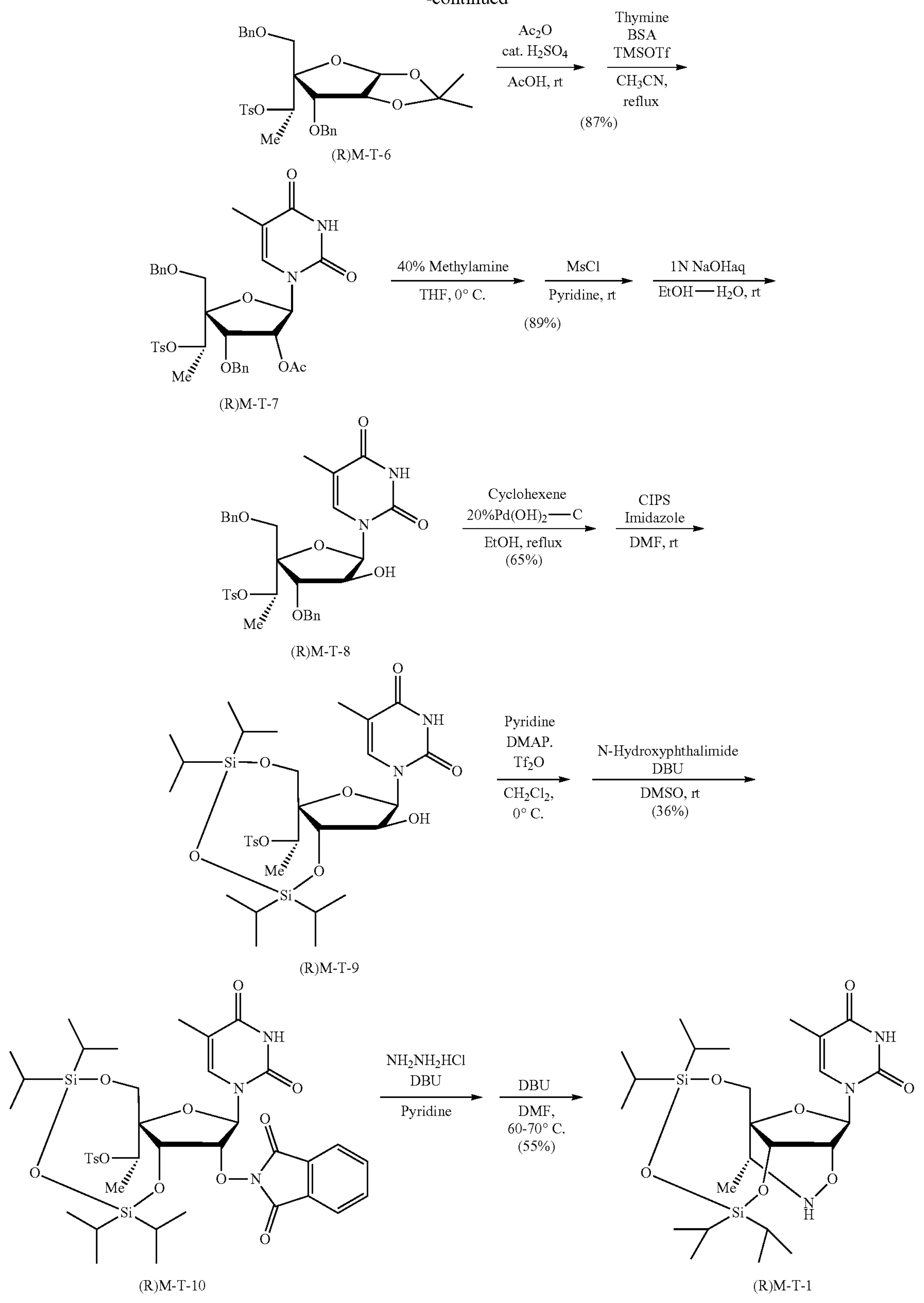
(Synthesis of Compound (R)M-T-5)
Under a nitrogen stream, oxalyl chloride (5.6 mL, 64.92 mmol) was dissolved in methylene chloride (240 mL), and then dimethyl sulfoxide (9.2 mL, 129.84 mmol) was added to the resultant solution under a dry ice-acetone bath. The solution was stirred at the same temperature for 30 minutes, and then a solution of compound S-1 (20.0 g, 49.94 mmol) in methylene chloride (40 mL) was added to the reaction solution. The resultant solution was further reacted while stirring at the same temperature for 45 minutes, and then triethylamine (27.8 mL, 199.76 mmol) was added to the reaction solution. The reaction solution was further stirred at the same temperature for 15 minutes, then the temperature was returned to room temperature, and then the reaction solution was stirred for 1 hour. The reaction solution was diluted with methylene chloride and 1N hydrochloric acid, then the diluted solution was fractionated to obtain an organic layer, then the organic layer was washed with a saturated aqueous sodium bicarbonate solution and saturated saline, then the washed solution was dried over anhydrous sodium sulfate, and the resultant solution was subjected to distillation under reduced pressure to obtain an intermediate. Subsequently, under a nitrogen stream, cerium chloride (12.3 g, 49.9 mmol) was dissolved in tetrahydrofuran (240 mL). The resultant solution was stirred under room temperature for 30 minutes, and then methylmagnesium bromide (1M in tetrahydrofuran, 100 mL, 100.0 mmol) was added to the solution under an ice bath. The solution was further stirred at the same temperature for 1.5 hours, and then a solution of the intermediate produced above in tetrahydrofuran (120 mL) was added to the solution under a dry ice-acetone bath. The resultant solution was stirred at the same temperature for 3 hours and was then further stirred under room temperature for 1 hour. The reaction of the reaction solution was terminated with a saturated aqueous ammonium chloride solution, then the reaction solution was diluted with ethyl acetate and water, and then the diluted solution was fractionated into an organic layer and an aqueous layer. The organic layer thus obtained was washed with 1N hydrochloric acid, a saturated aqueous sodium bicarbonate solution and saturated saline in this order, and then the washed solution was dried over anhydrous magnesium sulfate and was then subjected to distillation under reduced pressure. A crude product thus produced was purified by silica gel column chromatography (hexane:ethyl acetate=4:1 to 3:1) to produce compound (R)M-T-5 (19.0 g, 91%) as a colorless transparent oily substance.

1H NMR ($CDCl_3$) δ 1.20 (3H, d, J=6), 1.35 (3H, s), 1.59 (3H, s), 3.29 (1H, d, J=2), 3.63, 3.79 (2H, ABq, J=10), 4.41, 4.54 (2H, ABq, J=12), 4.44 (1H, d, J=5), 4.48, 4.86 (2H, ABq, J=11), 4.57-4.62 (1H, m), 4.67 (1H, dd, J=4, 5), 5.79 (1H, d, J=4), 7.23-7.38 (10H, m).

(Synthesis of Compound (R)M-T-6)

Under a nitrogen stream, compound (R)M-T-5 (9.06 g, 21.85 mmol) was dissolved in pyridine (143 mL), then p-toluenesulfonyl chloride (12.28 g, 64.43 mmol) was added to the resultant solution, and then the mixed solution was stirred at 80° C. for 13 hours. Subsequently, the temperature was decreased to 65° C., then p-toluenesulfonyl chloride (3.07 g, 16.11 mmol) was added to the solution, then the resultant solution was stirred at 80° C. for 7.5 hours, then the temperature was decreased to 65° C. again, then p-toluenesulfonyl chloride (3.07 g, 16.11 mmol) was added to the solution, and then the resultant solution was stirred at 80° C. for 2 hours. The reaction solution was cooled, then the reaction was terminated with water, then the reaction solution was diluted with ethyl acetate and saturated saline, and then the diluted solution was fractionated to obtain an organic layer. The organic layer thus obtained was washed with 1N hydrochloric acid, a saturated aqueous sodium bicarbonate solution and saturated saline in this order, the washed solution was dried over anhydrous sodium sulfate, and then the resultant solution was subjected to distillation under reduced pressure. A crude product thus produced was purified by silica gel column chromatography (hexane:ethyl acetate=3:1 to 3:1) to produce compound (R)M-T-6 (11.3 g, 91%) as a colorless transparent oily substance.

$^1$H NMR ($CDCl_3$) δ 1.32 (3H, s), 1.44 (3H, d, J=6), 1.53 (3H, s), 2.40 (3H, s), 3.48, 3.56 (2H, ABq, J=10), 4.22 (1H, d, J=5), 4.37-4.44 (3H, m), 4.59-4.62 (2H, m), 5.39 (2H, q, J=6), 5.75 (1H, d, J=4), 7.23-7.32 (12H, m), 7.72-7.75 (2H, m).

(Synthesis of Compound (R)M-T-7)

Under a nitrogen stream, (R)M-T-6 (11.20 g, 19.69 mmol) was dissolved in acetic acid (111 mL), then acetic anhydride (18.4 mL, 194.76 mmol) and concentrated sulfuric acid (0.072 g, 0.73 mmol) were added to the solution in this order, and then the resultant solution was stirred under room temperature for 2.5 hours. The reaction solution was neutralized with a saturated aqueous sodium bicarbonate solution, then the neutralized solution was diluted with ethyl acetate and water, and then the diluted solution was fractionated to obtain an organic layer. The organic layer thus obtained was washed with a saturated aqueous sodium bicarbonate solution and saturated saline in this order, and the washed solution was dried over anhydrous magnesium sulfate and was then subjected to distillation under reduced pressure. An intermediate thus produced was azeotropically dried with acetonitrile, and the resultant product was dissolved in acetonitrile (180 mL) under a nitrogen stream. Thymine (4.09 g, 32.46 mmol) and N,O-bis(trimethylsilyl) acetamide (21.4 mL, 86.56 mmol) were added in this order to the solution, and the resultant solution was stirred at 80° C. for 10 minutes. The temperature of the reaction solution was decreased to 45° C., then trimethylsilyl trifluoromethanesulfonate (4.6 mL, 25.97 mmol) was added to the reaction solution, and then the resultant solution was stirred at 88° C. for 1 hour. The reaction solution was cooled on ice, then the reaction was terminated with a saturated aqueous sodium bicarbonate solution, then the reaction solution was diluted with ethyl acetate and water, and then the diluted solution was fractionated to obtain an organic layer. The organic layer thus obtained was washed with saturated saline, and then the washed solution was dried over anhydrous magnesium and was then subjected to distillation under reduced pressure. A crude product thus produced was purified by silica gel column chromatography (hexane:ethyl acetate=3:2) to produce compound (R)M-T-7 (11.74 g, 87%) as a white foam-like solid substance.

$^1$H NMR ($CDCl_3$) δ 1.29 (3H, d, J=7), 1.49 (3H, d, J=1), 2.02 (3H, s), 2.43 (3H, s), 3.56, 3.76 (2H, ABq, J=10), 4.46-4.63 (5H, m), 5.10 (1H, q, J=7), 5.43 (1H, dd, J=6, 7), 6.23 (1H, d, J=8), 7.26-7.42 (13H, m), 7.69-7.72 (2H, m), 8.05 (1H, s).

(Synthesis of Compound (R)M-T-8)

Under a nitrogen atmosphere, (R)M-T-7 (11.72 g, 17.27 mmol) was dissolved in tetrahydrofuran (195 mL), then a 40% aqueous methylamine solution (26 mL, 307.0 mmol) was added to the solution under ice cooling, and then the resultant solution was stirred for 5 hours while ice-cooling. The reaction solution was subjected to distillation under reduced pressure, then the reaction solution was diluted with ethyl acetate and water, and then the diluted solution was fractionated to obtain an organic layer. The organic layer thus obtained was washed with saturated saline, and the washed solution was dried over anhydrous sodium sulfate and was then subjected to distillation under reduced pressure. An intermediate thus produced was dissolved pyridine (110 mL) under a nitrogen stream, then methanesulfonyl chloride (1.9 mL, 24.95 mmol) was added to the solution under ice cooling, and then the resultant solution was stirred at room temperature for 2 hours. The reaction solution was diluted with ethyl acetate, water and saturated saline, and the diluted solution was fractionated to obtain an organic layer. The organic layer thus obtained was washed with saturated saline, and the washed solution was dried over anhydrous sodium sulfate and was then subjected to distillation under reduced pressure. An intermediate thus produced was dissolved in ethanol (340 mL) and water (170 mL), then a 1M aqueous sodium hydroxide solution (115 mL, 115.0 mmol) was added to the solution, and then the resultant solution was stirred at room temperature for 14 hours. The reaction solution was neutralized with 1N hydrochloric acid, and then the reaction solution was subjected to distillation under reduced pressure. A residue thus obtained was diluted with ethyl acetate and water, and then the diluted solution was fractionated to obtain an organic layer. The organic layer thus obtained was washed with saturated saline, and the washed solution was dried over anhydrous sodium sulfate and was then subjected to distillation under reduced pressure. A crude product thus produced was purified by silica gel column chromatography (hexane:ethyl acetate=1:1 to 1:2) to produce compound (R)M-T-8 (9.86 g, 89%) as a white foam-like solid substance.

$^1$H NMR ($CDCl_3$) δ 1.33 (3H, d, J=7), 1.62 (3H, s), 2.43 (3H, s), 3.58, 3.85 (2H, ABq, J=10), 4.11-4.15 (1H, m), 4.29 (1H, d, J=3), 4.44-4.45 (1H, m), 4.51 (2H, s), 4.57, 4.73 (2H, ABq, J=12), 5.06 (1H, q, J=6), 6.09 (1H, d, J=4), 7.23-7.41 (13H, m), 7.72-7.74 (2H, m), 8.77 (1H, s).

(Synthesis of Compound (R)M-T-9)

Under a nitrogen stream, compound (R)M-T-8 (4.00 g, 6.03 mmol) was dissolved in ethanol (80 mL), then cyclohexene (8.9 mL, 87.76 mmol) and a 20% (palladium hydroxide)-carbon powder (2.0 g) were added to the solution in this order, and then the resultant solution was heated under reflux for 40 minutes. Cyclohexene (8.9 mL, 87.76 mmol) was further added to the solution, then the resultant solution was heated under reflux for 55 minutes, then cyclohexene (4.0 mL, 39.44 mmol) was added to the solution, and the resultant solution was heated under reflux for 25 minutes. The reaction solution was filtrated, and a filtrate was subjected to distillation under reduced pressure. An intermediate thus produced was dissolved in N,N-dimethylformamide (56 mL) under a nitrogen stream, then 1,3-dichloro-1,1,3,3-tetraisopropyldisiloxane (2.4 mL, 7.54 mmol) and a 2.9M imidazole N,N-dimethylformamide solution (7.7 mL) were added to the resultant solution in this order under ice cooling, and then the resultant solution was stirred under room temperature for 16 hours. The reaction of the reaction solution was terminated with methanol, then the reaction solution was diluted with diethyl ether and water, and then the diluted solution was fractionated into an organic layer and an aqueous layer. The aqueous layer was subjected to back-extraction with diethyl ether. An organic layer obtained in the first fractionation was combined with an organic layer obtained by the back-extraction, then the resultant solution was washed with saturated saline, and the washed solution was dried over anhydrous sodium sulfate and was then subjected to distillation under reduced pressure. A crude product thus produced was purified by silica gel column chromatography (hexane:ethyl acetate=7:3 to 1:1) to produce compound (R)M-T-9 (2.76 g, yield: 65%) as a white foam-like solid substance.

$^1$H NMR ($CDCl_3$) δ 0.91-1.16 (28H, m), 1.47 (3H, d, J=6), 1.86 (3H, d, J=2), 2.45 (3H, s), 3.81-3.84 (2H, m), 3.94 (1H, ABq, J=12), 4.53 (1H, d, J=8), 4.66-4.72 (1H, m), 5.09 (1H, q, J=6), 6.05 (1H, d, J=7), 7.30-7.34 (3H, m), 7.80-7.82 (2H, m), 9.14 (1H, s).

(Synthesis of Compound (R)M-T-10)

Under a nitrogen stream, (R)M-T-9 (0.74 g, 1.06 mmol) was dissolved in dichloromethane (7.5 mL), then pyridine (0.41 mL, 5.07 mmol), 4-dimethylaminopyridine (0.39 g, 3.23 mmol) and trifluoromethanesulfonic anhydride (0.45 mL, 2.70 mmol) were added to the solution in this order under ice cooling, and then the resultant solution was stirred for 3.5 hours while ice cooling. 4-Dimethylaminopyridine (0.13 g, 1.07 mmol) was further added to the solution, and the resultant solution was stirred for 3 hours while ice cooling. The reaction of the reaction solution was terminated with saturated saline, then the reaction solution was diluted with dichloromethane and water, and then the diluted solution was fractionated into an organic layer and an aqueous layer. The aqueous layer was subjected to back-extraction with dichloromethane. An organic layer obtained in the first fractionation was combined with an organic layer obtained by the back-extraction, then the resultant solution was washed with 1N hydrochloric acid, a saturated aqueous sodium bicarbonate solution and saturated saline in this order, and the washed solution was dried over anhydrous sodium sulfate and was then subjected to distillation under reduced pressure. An intermediate thus produced was dissolved in dimethyl sulfoxide (9.4 mL) under a nitrogen atmosphere, then N-hydroxyphthalimide (0.48 g, 2.91 mmol) and 1,8-diazabicyclo[5.4.0]-7-undecene (0.42 mL, 2.80 mmol) were added to the solution, and then the resultant solution was stirred at room temperature for 86 hours. The reaction solution was diluted with diethyl ether and water, and the diluted solution was fractionated into an organic layer and an aqueous layer. The aqueous layer was subjected to back-extraction with diethyl ether. An organic layer obtained in the first fractionation was combined with an organic layer obtained by the back-extraction, then the resultant solution was washed with water and saturated saline in this order, and the washed solution was dried over anhydrous sodium sulfate. A crude product thus produced was purified by silica gel column chromatography (hexane: ethyl acetate=2:1 to 1:1) to produce compound (R)M-T-10 (0.33 g, yield: 36%) as a white foam-like solid substance.

$^1$H NMR ($CDCl_3$) δ 1.01-1.21 (28H, m), 1.67 (3H, d, J=7), 1.85 (3H, d, J=1), 2.33 (3H, s), 3.92, 3.97 (2H, ABq, J=11), 4.90 (1H, dd, J=1, 8), 5.18 (1H, d, J=8), 5.43 (1H, q, J=7), 6.09 (1H, d, J=1), 7.20-7.23 (2H, m), 7.76-7.86 (7H, m).

<Synthesis of Compound (R)M-T-1>

Under a nitrogen stream, (R)M-T-10 (0.26 g, 0.30 mmol) was dissolved in pyridine (3 mL), then hydrazine monohydrochloride (0.037 g, 0.54 mmol) and 1,8-diazabicyclo [5.4.0]-7-undecene (0.080 mL, 0.54 mmol) were added to the solution, and then the resultant solution was stirred at room temperature for 15 hours. The reaction solution was diluted with ethyl acetate and water, and the diluted solution was fractionated into an organic layer and an aqueous layer. The aqueous layer was subjected to back-extraction with ethyl acetate. An organic layer obtained in the first fractionation was combined with an organic layer obtained by the back-extraction, then the resultant solution was washed with saturated saline, and the washed solution was dried over anhydrous sodium sulfate and was then subjected to distillation under reduced pressure. An intermediate thus produced was azeotropically dried with toluene, then the resultant product was dissolved in N,N-dimethylformamide (8.0 mL) under a nitrogen stream, then 1,8-diazabicyclo[5.4.0]-

7-undecene (0.32 mL, 2.14 mmol) was added to the solution, and then the resultant solution was stirred at 60° C. for 1 hour and then at 70° C. for 23 hours. The reaction solution was diluted with ethyl acetate and water, and the diluted solution was fractionated into an organic layer and an aqueous layer. The aqueous layer was subjected to back-extraction with ethyl acetate. An organic layer obtained in the first fractionation was combined with an organic layer obtained by the back-extraction, then the resultant solution was washed with saturated saline, and the washed solution was dried over anhydrous sodium sulfate and was then subjected to distillation under reduced pressure. A crude product thus produced was purified by silica gel column chromatography (hexane:ethyl acetate=1:1 to 1:2) to produce compound (R)M-T-1 (0.092 g, yield: 55%) as a white foam-like solid substance.

(Synthesis of Compound (R)M-T-2)

A 20% aqueous formaldehyde solution (0.31 mL, 2.0 mmol) was added to a solution of compound (R)M-T-1 (0.53 g, 0.98 mmol) in a 0.5M solution of pyridinium p-toluenesulfonate in methanol (7.2 mL) under ice cooling. Subsequently, sodium cyanoborohydride (0.11 g, 1.80 mmol) was added to the solution while ice cooling, and then the resultant solution was stirred for 1 hour while ice cooling. The reaction solution was diluted with ethyl acetate, water and saturated saline, and the diluted solution was fractionated to obtain an organic layer. The organic layer thus obtained was washed with saturated saline, and the washed solution was dried over anhydrous sodium sulfate and was then subjected to distillation under reduced pressure. A crude product thus produced was purified by silica gel column chromatography (hexane:ethyl acetate=3:1 to 1:1) to produce compound (R)M-T-2 (0.48 g, 89%) as a white foam-like solid substance.

1H NMR ($CDCl_3$) δ 0.93 (3H, d, J=6), 1.03-1.12 (28H, m), 1.90 (3H, d, J=1), 2.72 (3H, s), 2.94 (1H, q, J=6 Hz), 3.62, 4.10 (2H, AB, J=13), 4.02 (1H, d, J=3 Hz), 4.28 (1H, d, J=3 Hz), 6.23 (1H, s), 7.70 (1H, d, J=1), 8.35 (1H, s).

(Synthesis of Compound (R)M-T-3)

Compound (R)M-T-2 (0.60 g, 1.02 mmol) was dissolved in tetrahydrofuran (6 mL), then tetra-n-butylammonium fluoride (a 1M solution in tetrahydrofuran, 2.3 mL, 2.30 mmol) was added to the solution, and then the resultant solution was stirred at room temperature for 15 minutes. The resultant reaction solution was subjected to distillation under reduced pressure, and then a reaction residue was removed from the reaction solution by silica gel column chromatography (ethyl acetate:methanol=30:1 to 15:1) to produce an intermediate. The intermediate thus produced was azeotropically dried with pyridine, and then the resultant product was dissolved in pyridine (4.5 mL) under a nitrogen stream. 4,4'-Dimethoxytrityl chloride (0.52 g, 1.52 mmol) was added to the solution, and then the resultant solution was stirred at room temperature for 15 hours. Methanol was added to the reaction solution to terminate the reaction, then the reaction solution was diluted with ethyl acetate and water, and the diluted solution was fractionated to obtain an organic layer. The organic layer thus obtained was washed with saturated saline, and the washed solution was dried over anhydrous sodium sulfate and was then subjected to distillation under reduced pressure. A crude product thus produced was purified by silica gel column chromatography (hexane:ethyl acetate=1:1) to produce compound (R)M-T-3 (0.58 g, 90%) as a white foam-like solid substance.

$^1$H NMR ($CDCl_3$) δ 0.77 (3H, d, J=6 Hz), 1.35 (3H, d, J=1), 2.69 (1H, d, J=12), 2.71 (3H, s), 2.80 (1H, q, J=6), 3.22, 3.41 (2H, ABq, J=10), 3.80 (6H, d, J=1), 4.35 (1H, d, J=3 Hz), 4.57 (1H, dd, J=3, 10 Hz), 6.33 (1H, s), 6.83-6.87 (4H, m), 7.22-7.46 (9H, m), 7.86 (1H, d, J=1), 8.39 (1H, s).

(Synthesis of Compound (R)M-T-4)

Under a nitrogen stream, compound (R)M-T-3 (0.54 g, 1.57 mmol) was azeotropically dried with acetonitrile, and then the resultant product was dissolved in acetonitrile (7 mL). 4,5-Dicyanoimidazole (0.22 g, 1.01 mmol) and 2-cyanoethylN,N,N',N'-tetraisopropylphosphordiamidite (0.36 mL, 1.10 mmol) were added to the solution in this order under ice cooling, and then the resultant solution was stirred at room temperature for 5 hours. The reaction solution was diluted with ethyl acetate and water, and the diluted solution was fractionated to obtain an organic layer. The organic layer thus obtained was washed with saturated saline, and the washed solution was dried over anhydrous sodium sulfate and was then subjected to distillation under reduced pressure. A crude product thus produced was purified by silica gel column chromatography (hexane:ethyl acetate=2:1 to 1:1) to produce compound (R)M-T-4 (0.50 g, 70%) as a white foam-like solid substance.

$^{31}$P NMR ($CDCl_3$) δ 148.7, 149.0.

HRMS (MALDI): calcd for $C_{43}H_{55}N5O9P$ [M+H$^+$] 816.3732, found 816.3746.

Synthesis Example 2

A compound (1) wherein "Base" was a thymin-1-yl group, $A^1$ was a single bond, $R^1$ was DMTr, $R^2$ was —P(N(i-Pr)$_2$)($OC_2H_4CN$), $R^3$ was a methyl group, $R^4$ was an ethyl group in the R-configuration, $R^5$ was a hydrogen atom and n was 1 (hereinafter, also referred to as "compound (R)E-T-4") was synthesized in accordance with the reaction scheme shown below.

[Formula 48]

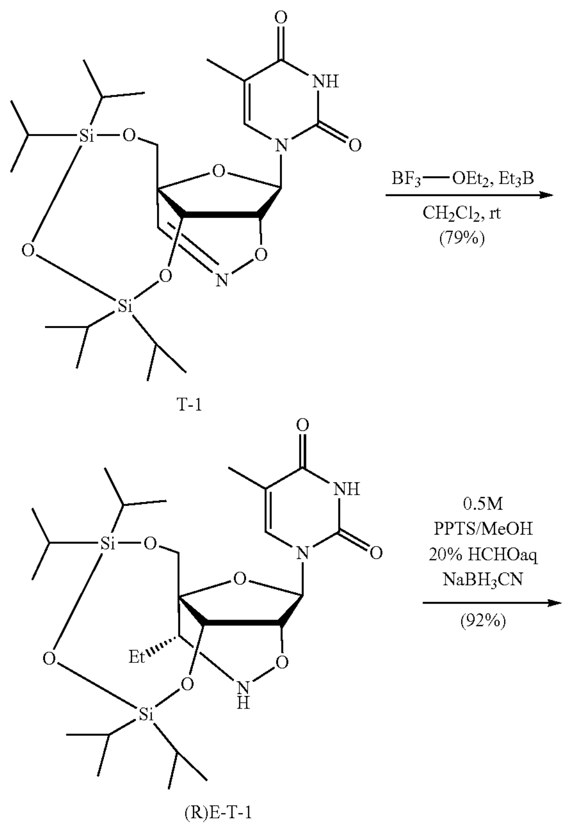

-continued

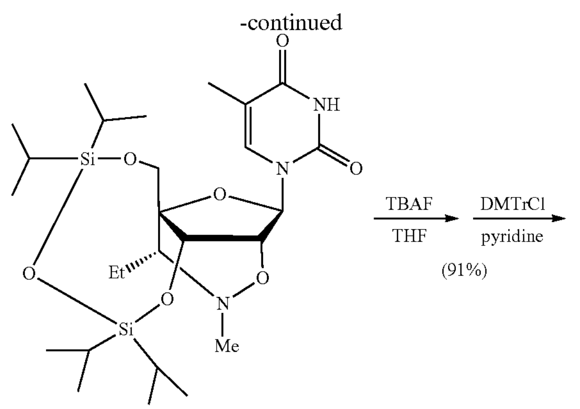

(R)E-T-2

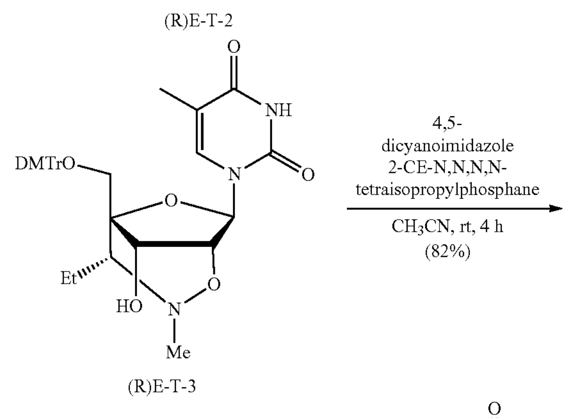

(R)E-T-3

(R)E-T-4

(Synthesis of Compound (R)E-T-1)

Under a nitrogen stream, compound T-1 (2.4 g, 4.63 mmol) was dissolved in methylene chloride (77 mL), and then a boron trifluoride-ethyl ether complex (1.5 mL, 24.39 mmol) and triethylborane (1M in hexane, 12.2 mL, 24.39 mmol) were added to the solution at room temperature. The resultant solution was stirred at room temperature for 5 minutes while bubbling with air, and then a boron trifluoride-ethyl ether complex (1.5 mL, 24.39 mmol) and triethylborane (1M in hexane, 12.2 mL, 24.39 mmol) were added to the solution. The resultant solution was stirred at room temperature for 10 minutes while bubbling with air, then a boron trifluoride-ethyl ether complex (0.2 mL, 1.59 mmol) and triethylborane (1M in hexane, 2.0 mL, 2.00 mmol) were added to the solution, and the resultant solution was stirred at room temperature for 5 minutes while bubbling with air. The reaction of the reaction solution was terminated with a saturated aqueous sodium bicarbonate solution, then the resultant solution was diluted with dichloromethane and water, and the diluted solution was fractionated into an organic layer and an aqueous layer. The aqueous layer was subjected to back-extraction with dichloromethane. The organic layer obtained in the first fractionation was combined with the organic layer obtained in the back-extraction, the resultant solution was washed with saturated saline, and then the washed solution was dried over anhydrous sodium sulfate and was then distilled under reduced pressure. A crude product thus produced was purified by silica gel column chromatography (hexane:ethyl acetate=3:2 to 1:1) to produce compound (R)E-T-1 (2.05 g, yield: 79%) as a white foam-like solid substance.

$^1$H NMR ($CDCl_3$) δ 0.92-1.13 (28H, m), 1.21-1.46, (2H, m), 1.92 (3H, d, J=1 Hz), 3.58 (1H, br), 3.70, 4.17 (2H, ABq, J=13 Hz), 4.13 (1H, d, J=4 Hz), 4.33 (1H, d, J=3 Hz), 5.51 (1H, br), 6.14 (1H, s), 7.73 (1H, d, J=1 Hz), 8.58 (1H, s).

(Synthesis of Compound (R)E-T-2)

Under a nitrogen stream, compound (R)E-T-1 (0.97 g, 1.75 mmol) was dissolved in a 0.5M solution of pyridium p-toluenesulfonate in methanol (11.5 mL, 5.76 mmol), then a 20% aqueous formaldehyde solution (0.49 mL, 3.24 mmol) and sodium cyanoborohydride (0.18 mg, 2.88 mmol) were added to the solution in this order under ice cooling, and the resultant solution was stirred for 30 minutes while ice cooling. The reaction solution was diluted with ethyl acetate, water and saturated saline, and the diluted solution was fractionated to obtain an organic layer. The organic layer thus obtained was washed with saturated saline, and the washed solution was dried over anhydrous sodium sulfate and was then subjected to distillation under reduced pressure. A crude product thus produced was purified by silica gel column chromatography (hexane:ethyl acetate=2:1 to 3:2) to produce compound (R)E-T-2 (0.92 g, 92%) as a white foam-like solid substance.

$^1$H NMR ($CDCl_3$) δ 0.91-1.13 (28H, m), 1.29-1.36, (1H, m), 1.57-1.68, (1H, m), 1.91 (3H, d, J=1 Hz), 2.74 (3H, s), 2.81 (1H, m), 3.73, 4.20 (2H, ABq, J=13 Hz), 3.98 (1H, d, J=3 Hz), 4.26 (1H, d, J=3 Hz), 6.26 (1H, s), 7.72 (1H, d, J=1 Hz), 8.34 (1H, s).

(Synthesis of Compound (R)E-T-3)

Compound (R)E-T-2 (0.98 g, 0.20 mmol) was dissolved in tetrahydrofuran (20 mL), then tetra-n-butylammonium fluoride (a 1M solution in tetrahydrofuran, 4.0 mL, 3.99 mmol) was added to the solution, and then the resultant solution was stirred at room temperature for 20 minutes. The reaction solution thus produced was subjected to distillation under reduced pressure, and then a reaction residue was removed by silica gel column chromatography (ethyl acetate:methanol=40:1 to 20:1) to produce an intermediate. An intermediate thus produced was azeotropically dried with pyridine, and then the resultant product was dissolved in pyridine (7 mL) under a nitrogen stream. 4,4'-Dimethoxytrityl chloride (0.77 g, 2.28 mmol) was added to the reaction solution, and the resultant solution was stirred at room temperature for 15 hours. Methanol was added to the reaction solution to terminate the reaction, then the reaction solution was diluted with ethyl acetate and water, and the diluted solution was fractionated into an organic layer and an aqueous layer. The aqueous layer was subjected to back-extraction with ethyl acetate. An organic layer obtained in the first fractionation was combined with an organic layer obtained by the back-extraction, then the resultant solution was washed with saturated saline, and the washed solution was dried over anhydrous sodium sulfate and was then subjected to distillation under reduced pressure. A crude product thus produced was purified by silica gel column chromatography (hexane:ethyl acetate=2:1 to 1:4) to produce compound (R)E-T-3 (1.06 g, 91%) as a white foam-like solid substance.

$^1H$ NMR ($CDCl_3$) δ 0.75 (3H, t, J=8 Hz), 1.07-1.15, 1.42-1.51 (2H, m), 1.30 (3H, s), 2.59 (1H, m), 2.63 (1H, m), 2.71 (3H, s), 3.26, 3.54 (2H, ABq, J=11), 3.79 (6H, d, J=1), 4.32 (1H, d, J=3 Hz), 4.51 (1H, dd, J=3, 9 Hz), 6.35 (1H, s), 6.84-6.87 (4H, m), 7.23-7.46 (9H, m), 7.89 (1H, s), 8.33 (1H, s).

(Synthesis of Compound (R)E-T-4)

Under a nitrogen stream, compound (R)E-T-3 (1.03 g, 1.64 mmol) was azeotropically dried with acetonitrile, and the resultant product was dissolved in acetonitrile (11 mL). 4,5-Dicyanoimidazole (0.22 g, 1.90 mmol) and 2-cyanoethyl-N,N,N',N'-tetraisopropylphosphordiamidite (0.68 mL, 2.08 mmol) were added to the solution in this order under ice cooling, and the resultant solution was stirred at room temperature for 4 hours. The reaction solution was diluted with ethyl acetate and water, and the diluted solution was fractionated to obtain an organic layer. The organic layer thus obtained was washed with saturated saline, and the washed solution was dried over anhydrous sodium sulfate and was then subjected to distillation under reduced pressure. A crude product thus produced was purified by silica gel column chromatography (hexane:ethyl acetate=1:1 to 2:3) to produce compound (R)E-T-4 (1.13 g, 82%) as a white foam-like solid substance.

$^{31}P$ NMR ($CDCl_3$) δ 149.1, 150.5.

HRMS (MALDI): calcd for $C_{46}H_{56}F_3N_6NaO_{10}P$ [M+H$^+$] 830.3888, found 830.3883.

Synthesis Example 3

A compound (1) wherein "Base" was an N-benzoyl-adenin-9-yl group, $A^1$ was a single bond, $R^1$ was DMTr, $R^2$ was —P(N(i-Pr)$_2$)($OC_2H_4CN$), $R^3$ was a methyl group, $R^4$ was an ethyl group in the R-configuration, $R^5$ was a hydrogen atom, and n was 1 (hereinafter, also referred to as "compound (R)E-A-3") was synthesized in accordance with the reaction scheme shown below.

[Formula 49]

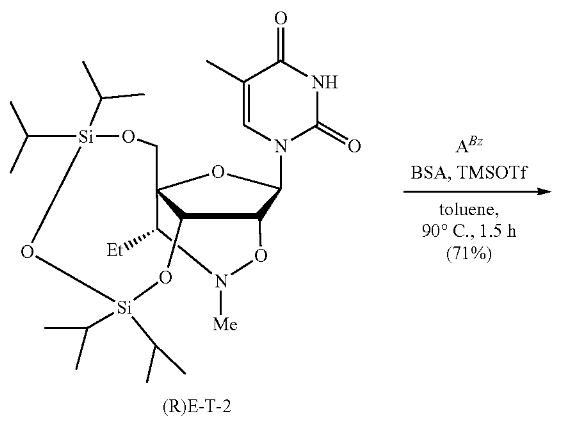

(R)E-T-2

-continued

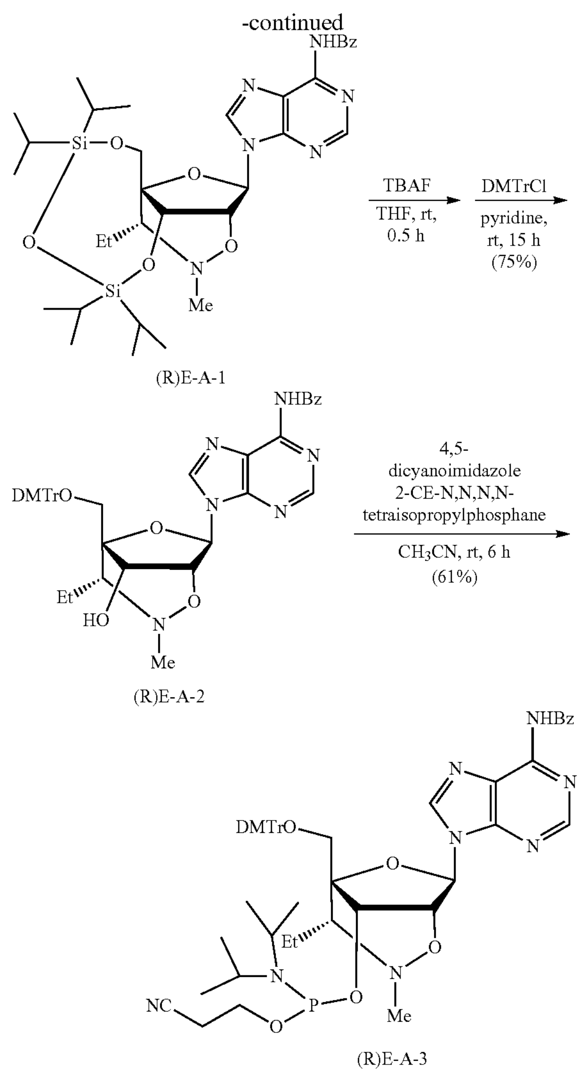

(R)E-A-1

(R)E-A-2

(R)E-A-3

(Synthesis of Compound (R)E-A-1)

Under a nitrogen stream, compound (R)E-T-2 (0.33 g, 0.57 mmol) was dissolved in toluene (6.7 mL), then $N^6$-benzoyladenine (0.21 g, 0.88 mmol) and N,O-bis(trimethylsilyl) acetamide (0.87 mL, 3.50 mmol) were added to the solution in this order, and then the resultant solution was stirred at 90° C. for 0.5 hour. Subsequently, trimethylsilyl trifluoromethanesulfonate (0.15 mL, 0.82 mmol) was added to the solution, and the resultant solution was stirred at 90° C. for 1 hour. The reaction solution was cooled on ice, then the reaction was terminated with a saturated aqueous sodium bicarbonate solution, then the reaction solution was diluted with ethyl acetate and water, then the diluted solution was subjected to filtration through celite to collect a filtrate, and the filtrate was fractionated to obtain an organic layer. The organic layer thus obtained was washed with saturated saline, and the washed solution was dried over anhydrous sodium sulfate and was then subjected to distillation under reduced pressure. A crude product thus produced was purified by silica gel column chromatography (hexane:ethyl acetate=2:1 to 1:1) to produce compound (R)E-A-1 (0.27 g, 71%) as a white foam-like solid substance.

$^1H$ NMR ($CDCl_3$) δ 0.98-1.15 (31H, m), 1.33-1.44 (1H, m), 1.65-1.74 (1H, m), 2.80 (3H, s), 2.91 (1H, m), 3.81, 4.20 (2H, ABq, J=13 Hz), 4.52 (1H, d, J=3 Hz), 4.64 (1H, d, J=3

Hz), 6.78 (1H, s), 7.51-7.56 (2H, m), 7.59-7.64 (1H, m), 8.01-8.04 (2H, m), 8.36 (1H, s), 8.83 (1H, s), 9.01 (1H, s).

(Synthesis of Compound (R)E-A-2)

Compound (R)E-A-1 (0.30 g, 0.44 mmol) was dissolved in tetrahydrofuran (3 mL), then tetra-n-butylammonium fluoride (a 1M solution in tetrahydrofuran, 0.92 mL, 0.92 mmol) was added to the solution, and the resultant solution was stirred at room temperature for 30 minutes. The reaction solution thus produced was subjected to distillation under reduced pressure, and then a reaction residue was removed by silica gel column chromatography (ethyl acetate:methanol=30:1 to 10:1) to produce an intermediate. The intermediate thus produced was azeotropically dried with pyridine, and the resultant product was dissolved in pyridine (2 mL) under a nitrogen stream. 4,4'-Dimethoxytrityl chloride (0.18 g, 0.53 mmol) was added to the solution, and the resultant solution was stirred at room temperature for 16 hours. The reaction solution was cooled on ice, then the reaction was terminated with methanol, then the reaction solution was diluted with water and ethyl acetate, and the diluted solution was fractionated to obtain an organic layer. The organic layer thus obtained was washed with saturated saline, and the washed solution was dried over anhydrous sodium sulfate and was then subjected to distillation under reduced pressure. A crude product thus produced was purified by silica gel column chromatography (hexane:ethyl acetate=1:2 to 0:1) to produce compound (R)E-A-2 (0.25 g, 75%) as a white solid substance.

$^1$H NMR (DMSO-d6) δ 0.69 (3H, t, J=7 Hz), 1.05-1.13 (1H, m), 1.38-1.45 (1H, m), 2.69 (3H, s), 2.74 (1H, d, J=3 Hz), 3.05, 3.36 (2H, ABq, J=10 Hz), 3.72 (6H, d, J=2 Hz), 4.69 (1H, d, J=3 Hz), 4.82 (1H, dd, J=3, 6 Hz), 5.60 (1H, d, J=6 Hz), 6.66 (1H, s), 6.86 (4H, d, J=8 Hz), 7.19-7.30 (7H, m), 7.37-7.40 (2H, m), 7.52-7.57 (2H, m), 7.62-7.67 (1H, m), 8.03-8.05 (2H, d, J=7 Hz), 8.57 (1H, s), 8.80 (1H, s), 11.26 (1H, s).

(Synthesis of Compound (R)E-A-3)

Under a nitrogen stream, compound (R)E-A-2 (0.20 g, 0.27 mmol) was azeotropically dried with acetonitrile, and then the resultant product was dissolved by adding acetonitrile (3 mL) and tetrahydrofuran (2 mL). 4,5-Dicyanoimidazole (0.035 g, 0.30 mmol) and 2-cyanoethyl-N,N,N',N'-tetraisopropylphosphordiamidite (0.11 mL, 0.32 mmol) were added to the solution in this order, and the resultant solution was stirred at room temperature for 6 hours. Subsequently, 4,5-dicyanoimidazole (0.018 g, 0.15 mmol) and 2-cyanoethyl-N,N,N',N'-tetraisopropylphosphordiamidite (0.053 mL, 0.16 mmol) were added to the solution in this order, and the resultant solution was further stirred for 16 hours. The reaction was terminated with water, then the reaction solution was diluted with ethyl acetate, and the diluted solution as fractionated to obtain an organic layer. The organic layer thus obtained was washed with water and saturated saline in this order, and the washed solution was dried over anhydrous sodium sulfate and was then subjected to distillation under reduced pressure. A crude product thus produced was purified by silica gel column chromatography (hexane:ethyl acetate=3:2 to 1:2) to produce compound (R)E-A-3 (0.15 g, 61%) as a white foam-like solid substance.

$^{31}$P NMR ($CDCl_3$) δ 148.9, 149.1.

HRMS (MALDI): calcd for C51H59N8NaO8P [M+Na$^+$] 965.4086, found 965.4096.

Synthesis Example 4

A compound (1) wherein "Base" was a thymin-1-yl group, $A^1$ was a single bond, $R^1$ was DMTr, $R^2$ was —P(N(i-Pr)$_2$)($OC_2H_4CN$), $R^4$ was a methyl group, and n was 0 (hereinafter, also referred to as "compound OM-T-3") was synthesized in accordance with the reaction scheme shown below.

[Formula 50]

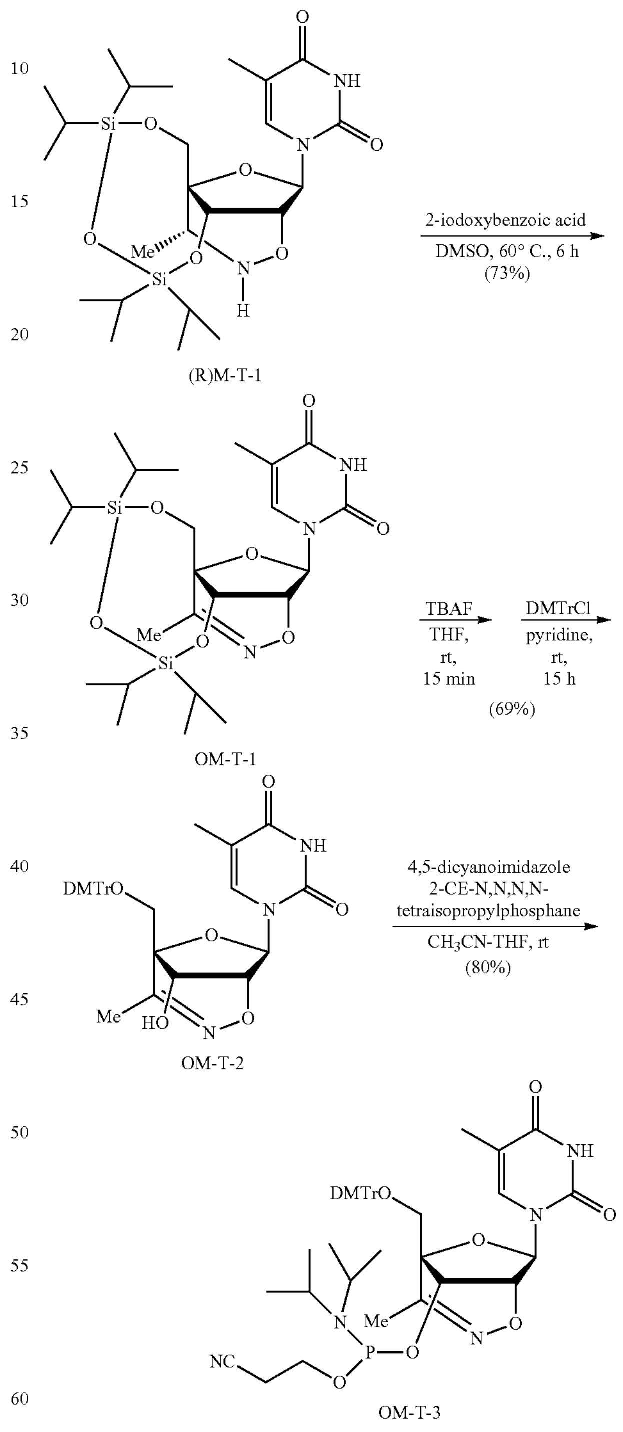

(Synthesis of Compound OM-T-1)

Under a nitrogen stream, compound (R)M-T-1 (2.88 g, 5.31 mmol) was dissolved in dimethyl sulfoxide (58 mL), then 2-iodoxybenzoic acid (3.89 g, 5.84 mmol) was added to the solution at room temperature, and the resultant solution was stirred at 60° C. for 6 hours and was then further stirred for 9 hours while cooling in air to room temperature. The reaction solution was cooled with water, then the reaction was terminated with a saturated aqueous sodium bicarbonate solution, then the reaction solution was diluted with ethyl acetate and water, and the diluted solution was fractionated to obtain an organic layer. The organic layer was washed with saturated saline, and was then dried over anhydrous sodium sulfate, and the dried product was subjected to distillation under reduced pressure. A crude product thus produced was purified by silica gel column chromatography (hexane:ethyl acetate=2:1) to produce compound OM-T-1 (2.12 g, 73%) as a white foam-like solid substance.

$^1$H NMR ($CDCl_3$) δ 1.00-1.14 (28H, m), 1.91 (3H, s), 1.94 (3H, s), 3.89, 4.22 (2H, ABq, J=13), 4.45 (1H, d, J=4 Hz), 4.61 (1H, dd, J=4, 1), 5.86 (1H, s), 7.44 (1H, s), 8.40 (1H, s).

(Synthesis of Compound OM-T-2)

Compound OM-T-1 (1.36 g, 2.51 mmol) was dissolved in tetrahydrofuran (14 mL), then tetra-n-butylammonium fluoride (a 1M solution in tetrahydrofuran, 5.4 mL, 5.40 mmol) was added to the solution, and the resultant solution was stirred at room temperature for 15 minutes. The reaction solution thus produced was subjected to distillation under reduced pressure, and then a reaction residue was removed by silica gel column chromatography (ethyl acetate:methanol=30:1 to 10:1) to produce an intermediate. The intermediate was azeotropically dried with pyridine, and the resultant product was dissolved in pyridine (25 mL) under a nitrogen stream. 4,4'-Dimethoxytrityl chloride (1.62 g, 4.78 mmol) was added to the solution, and the resultant solution was stirred at room temperature for 15 hours. Methanol was added to the solution to terminate the reaction, then the solution was diluted with water and ethyl acetate, and the diluted solution was fractionated to obtain an organic layer. The organic layer thus obtained was washed with saturated saline, and the washed solution was dried over anhydrous sodium sulfate and was then subjected to distillation under reduced pressure. Dichloromethane was added to a crude product thus produced, and a precipitated solid substance was collected by filtration to obtain compound OM-T-2 (1.01 g, 69%) as a white solid substance.

$^1$H NMR ($CDCl_3$) δ 1.37 (3H, d, J=1), 1.66 (3H, s), 3.37 (2H, brs), 3.75 (6H, s), 4.62-4.64 (2H, m), 5.81 (1H, s), 6.13 (1H, d, J=4), 6.90-6.93 (4H, m), 7.23-7.36 (7H, m), 7.42-7.45 (2H, m), 7.55 (1H, d, J=1), 11.48 (1H, brs).

(Synthesis of Compound OM-T-3)

Under a nitrogen stream, compound OM-T-2 (0.40 g, 0.65 mmol) was azeotropically dried with acetonitrile, and the resultant product was dissolved in acetonitrile (4 mL). 4,5-Dicyanoimidazole (0.087 g, 0.73 mmol) and 2-cyanoethyl-N,N,N',N'-tetraisopropylphosphordiamidite (0.26 mL, 0.80 mmol) were added to the solution in this order under ice cooling, and the resultant solution was stirred at room temperature for 5 hours. The reaction solution was cooled on ice, then the reaction was terminated with water, then the reaction solution was diluted with ethyl acetate and saturated saline, and the diluted solution was fractionated to obtain an organic layer. The organic layer thus obtained was washed with water and saturated saline in this order, and the washed solution was dried over anhydrous sodium sulfate and was then subjected to distillation under reduced pressure. A crude product thus produced was purified by silica gel column chromatography (hexane:ethyl acetate=2:1 to 1:1) to produce compound OM-T-3 (0.42 g, 80%) as a white foam-like solid substance.

$^{31}$P NMR ($CDCl_3$) δ 149.4, 149.7.

HRMS (MALDI): calcd for C42H50N5NaO9P [M+Na$^+$] 822.3238, found 822.3232.

Synthesis Example 5

A compound (1) wherein "Base" was a thymin-1-yl group, $A^1$ was a single bond, $R^1$ was DMTr, $R^2$ was —P(N(i-Pr)$_2$)($OC_2H_4CN$), $R^3$ was a methyl group, $R^4$ was a methyl group in the S-configuration, $R^5$ was a hydrogen atom, and n was 1 (hereinafter, also referred to as "compound (S)M-T-4") was synthesized in accordance with the reaction scheme shown below.

[Formula 51]

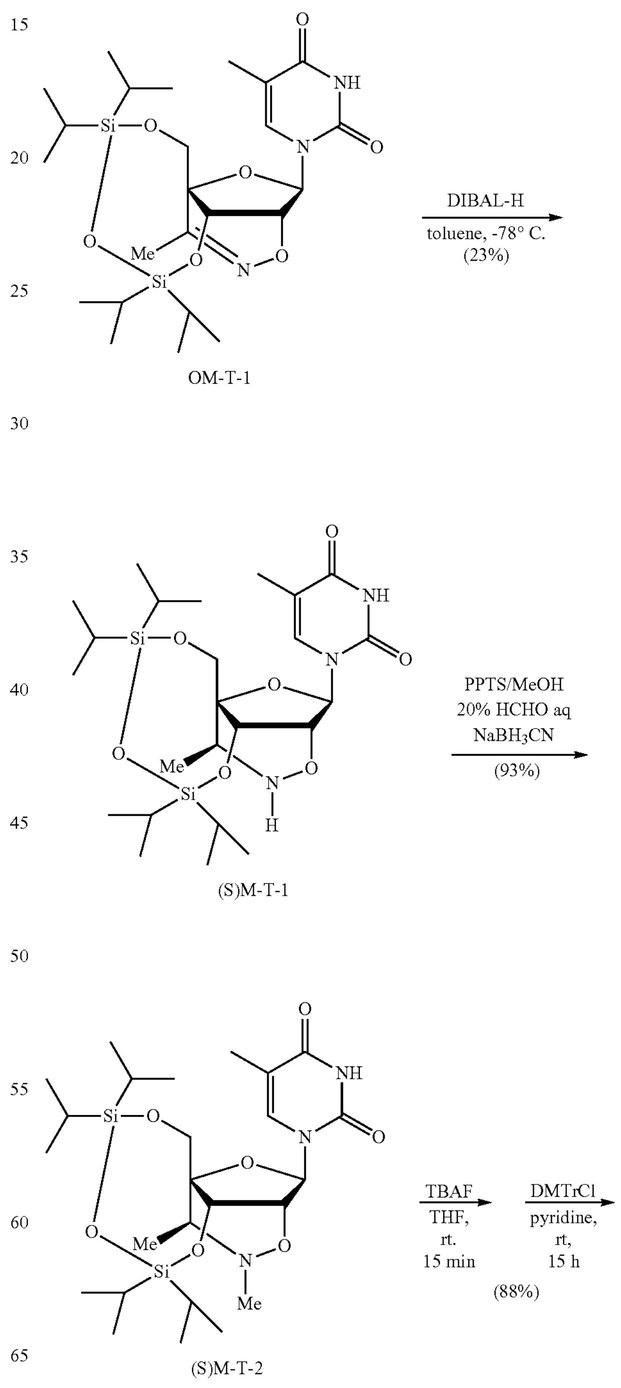

-continued

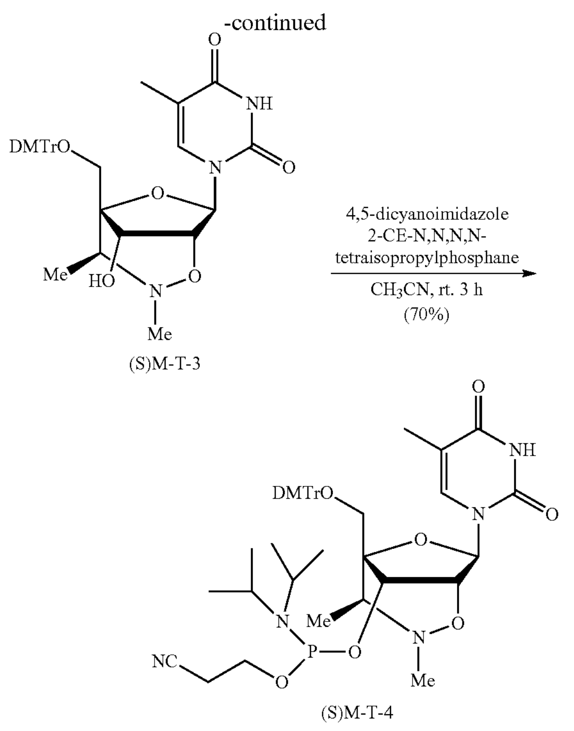

(S)M-T-3

(S)M-T-4

(Synthesis of Compound (S)M-T-1)

Under a nitrogen stream, compound OM-T-1 (0.20 g, 0.37 mmol) was dissolved in toluene (4 mL), then a 1.0 mol/L solution of diisobutylaluminium hydride in hexane (1.5 mL, 1.5 mmol) was added to the solution under cooling with dry ice/acetone, and the resultant solution was stirred for 2 hours while cooling. The reaction was terminated with a saturated aqueous Rochelle salt solution, then the reaction solution was diluted with ethyl acetate and water, and the diluted solution was fractionated to obtain an organic layer. The organic layer thus obtained was washed with saturated saline, and the washed solution was dried over anhydrous sodium sulfate and was then subjected to distillation under reduced pressure. A crude product thus produced was purified by silica gel column chromatography (hexane:ethyl acetate=3:2 to 1:1) to produce compound (S)M-T-1 (0.046 g, 23%) as a white foam-like solid substance.

$^1H$ NMR ($CDCl_3$) δ 0.97-1.15 (28H, m), 1.46 (3H, d, J=7), 1.92 (3H, d, J=1), 3.08 (1H, q, J=7), 4.03 (2H, s), 4.18 (1H, d, J=2), 4.41 (1H, d, J=2), 6.06 (1H, s), 7.75 (1H, d, J=1), 8.46 (1H, s).

(Synthesis of Compound (S)M-T-2)

A 20% aqueous formaldehyde solution (0.16 mL, 1.0 mmol) was added dropwise to a solution of compound (S)M-T-1 (0.31 g, 0.57 mmol) in a 0.5M solution of pyridinium p-toluenesulfonate in methanol (3.6 mL) under ice cooling. Subsequently, sodium cyanoborohydride (0.058 g, 0.92 mmol) was added to the solution while ice cooling, and the resultant solution was stirred for 1 hour while ice cooling. The reaction solution was diluted with ethyl acetate, water and saturated saline, and the diluted solution was fractionated to obtain an organic layer. The organic layer thus obtained was washed with saturated saline, and the washed solution was dried over anhydrous sodium sulfate and was then subjected to distillation under reduced pressure. A crude product thus produced was purified by silica gel column chromatography (hexane:ethyl acetate=3:1 to 2:1) to produce compound (S)M-T-2 (0.29 g, 93%) as a white foam-like solid substance.

$^1H$ NMR ($CDCl_3$) δ 0.94-1.15 (28H, m), 1.32 (3H, d, J=7), 1.91 (3H, d, J=1), 2.68 (3H, s), 2.87 (1H, q, J=7 Hz), 3.97 (1H, d, J=3), 4.00, 4.08 (2H, ABq, J=13), 4.34 (1H, d, J=3 Hz), 6.24 (1H, s), 7.79 (1H, d, J=1), 8.40 (1H, s).

(Synthesis of Compound (S)M-T-3)

Compound (S)M-T-2 (0.31 g, 0.56 mmol) was dissolved in tetrahydrofuran (4 mL), then tetra-n-butylammonium fluoride (a 1M solution in tetrahydrofuran, 1.2 mL, 1.20 mmol) was added to the solution, and then the resultant solution was stirred at room temperature for 15 minutes. The reaction solution thus produced was subjected to distillation under reduced pressure, and then a reaction residue was removed by silica gel column chromatography (ethyl acetate:methanol=40:1 to 10:1) to produce an intermediate. The intermediate thus produced was azeotropically dried with pyridine, and the resultant product was dissolved in pyridine (5.4 mL) under a nitrogen stream. 4,4'-Dimethoxytrityl chloride (0.32 g, 0.95 mmol) was added to the solution, and the resultant solution was stirred at room temperature for 15 hours. Methanol was added to the solution to terminate the reaction, then the solution was diluted with water and ethyl acetate, and the diluted solution was fractionated to obtain an organic layer. A crude product thus produced was purified by silica gel column chromatography (hexane:ethyl acetate=1:2) to produce compound (S)M-T-3 (0.30 g, 88%) as a white foam-like solid substance.

$^1H$ NMR ($CDCl_3$) δ 1.04 (3H, d, J=7), 1.43 (3H, s), 2.67 (3H, s), 3.26 (1H, q, J=7), 3.40, 3.58 (2H, ABq, J=11), 3.80 (7H, s), 4.13 (1H, dd, J=3, 10), 4.42 (1H, d, J=3), 6.12 (1H, s), 6.82-6.87 (4H, m), 7.22-7.40 (7H, m), 7.46-7.49 (2H, m), 7.65 (1H, d, J=1), 8.35 (1H, s).

(Synthesis of Compound (S)M-T-4)

Under a nitrogen stream, compound (S)M-T-3 (0.28 g, 0.46 mmol) was azeotropically dried with acetonitrile, and the resultant product was dissolved in acetonitrile (4 mL). 4,5-Dicyanoimidazole (0.064 g, 0.54 mmol) and 2-cyanoethyl-N,N,N',N'-tetraisopropylphosphordiamidite (0.19 mL, 0.58 mmol) were added to the solution in this order under ice cooling, and the resultant solution was stirred at room temperature for 5 hours. The reaction solution was diluted with ethyl acetate and water, and the diluted solution was fractionated to obtain an organic layer. The organic layer thus obtained was washed with saturated saline, and the washed solution was dried over anhydrous sodium sulfate and was then subjected to distillation under reduced pressure. A crude product thus produced was purified by silica gel column chromatography (hexane:ethyl acetate=1:1) to produce compound (S)M-T-4 (0.26 g, 70%) as a white foam-like solid substance.

$^{31}P$ NMR ($CDCl_3$) δ 149.1, 149.2.

HRMS (MALDI): calcd for C43H54N5NaO9P [M+Na$^+$] 838.3551, found 838.3564.

Synthesis Example 6

A compound (1) wherein "Base" was a thymin-1-yl group, $A^1$ was a single bond, $R^1$ was DMTr, $R^2$ was —P(N(i-Pr)$_2$)($OC_2H_4CN$), $R^4$ was an ethyl group, and n was 0 (hereinafter, also referred to as "compound OE-T-3") was synthesized in accordance with the reaction scheme shown below.

[Formula 52]

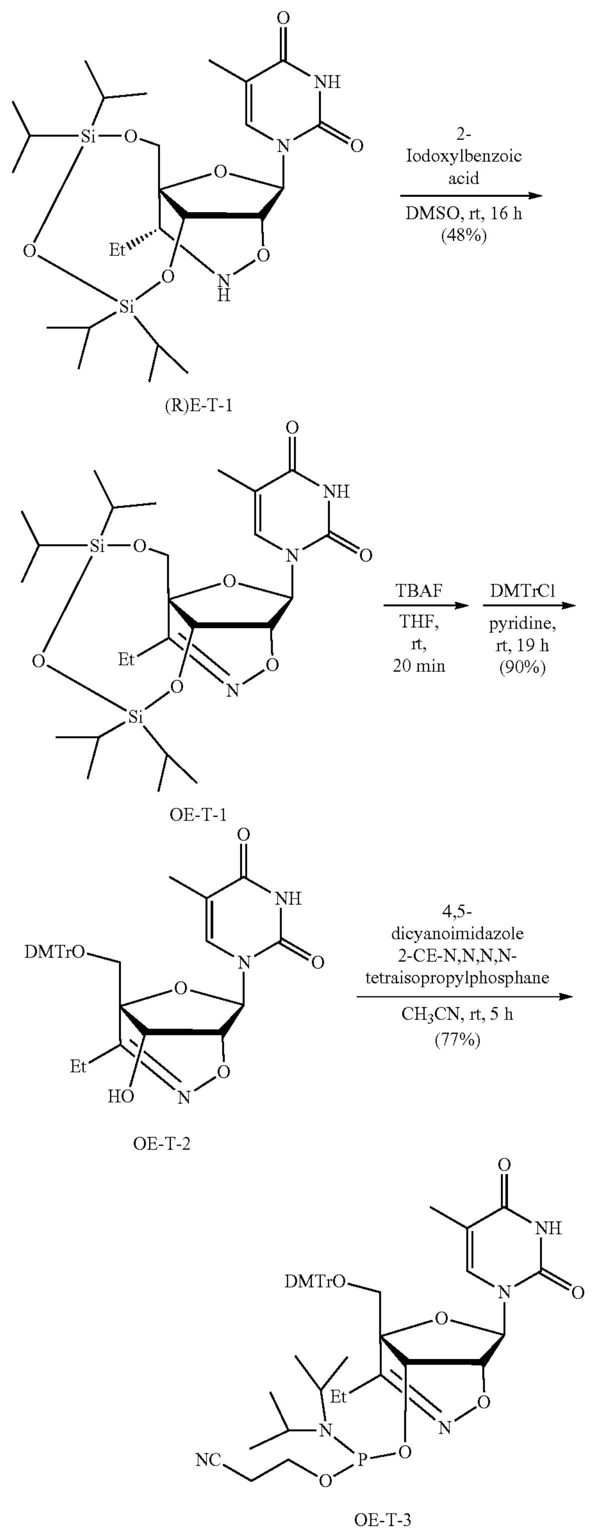

(R)E-T-1

OE-T-1

OE-T-2

OE-T-3

(Synthesis of Compound OE-T-1)

Under a nitrogen stream, compound (R)E-T-1 (6.48 g, 11.66 mmol) was dissolved in dimethyl sulfoxide (102 mL), then 2-iodoxybenzoic acid (9.00 g, 13.50 mmol) was added to the solution at room temperature, and the resultant solution was stirred at room temperature for 15 hours. The reaction solution was cooled with water, then the reaction was terminated with a saturated aqueous sodium hydrosulfite solution, then the reaction solution was diluted with ethyl acetate and water, and the diluted solution was fractionated into an organic layer and an aqueous layer. The aqueous layer was subjected to back-extraction with ethyl acetate. An organic layer obtained in the first fractionation was combined with an organic layer obtained in the back extraction, then the resultant solution was washed with a saturated aqueous sodium bicarbonate solution and saturated saline in this order, and the washed solution was dried over anhydrous sodium sulfate and was then subjected to distillation under reduced pressure. A crude product thus produced was purified by silica gel column chromatography (hexane:ethyl acetate=3:1 to 3:2) to produce compound OE-T-1 (3.10 g, 48%) as a white foam-like solid substance.

$^1$H NMR ($CDCl_3$) δ 0.92-1.14 (28H, m), 1.19 (3H, t, J=7), 1.91 (3H, s), 2.24 (2H, q, J=7), 3.94, 4.27 (2H, ABq, J=13 Hz), 4.44 (1H, d, J=4 Hz), 4.59 (1H, d, J=4 Hz), 5.88 (1H, s), 7.45 (1H, s), 8.41 (1H, s).

(Synthesis of Compound OE-T-2)

Compound OE-T-1 (0.11 g, 0.20 mmol) was dissolved in tetrahydrofuran (2 mL), then tetra-n-butylammonium fluoride (a 1M solution in tetrahydrofuran, 0.61 mL, 0.61 mmol) was added to the solution, and the resultant solution was stirred at room temperature for 20 minutes. The reaction solution thus produced was subjected to distillation under reduced pressure, and a reaction residue was removed by silica gel column chromatography (ethyl acetate:methanol=40:1 to 5:1) to produce an intermediate. The intermediate thus produced was azeotropically dried with pyridine, and the resultant product was dissolved in pyridine (2 mL) under a nitrogen stream. 4,4'-Dimethoxytrityl chloride (0.18 g, 0.52 mmol) was added to the solution, and the resultant solution was stirred at room temperature for 19 hours. Methanol was added to the reaction solution to terminate the reaction, then the resultant solution was diluted with ethyl acetate and water, and the diluted solution was fractionated to obtain an organic layer. The organic layer thus obtained was washed with saturated saline, and the washed solution was dried over anhydrous sodium sulfate and was then subjected to distillation under reduced pressure. A crude product thus produced was purified by silica gel column chromatography (hexane:ethyl acetate=1:2 to 1:3) to produce compound OE-T-2 (0.11 g, 90%) as a white foam-like solid substance.

$^1$H NMR ($CDCl_3$) δ 1.01 (3H, t, J=7 Hz), 1.47 (3H, d, J=1), 2.02-2.15 (2H, m), 2.65 (1H, br), 3.46, 3.66 (2H, ABq, J=11), 3.80 (6H, d, J=1), 4.65 (1H, d, J=4 Hz), 4.78 (1H, br), 6.00 (1H, s), 6.83-6.88 (4H, m), 7.24-7.45 (9H, m), 7.61 (1H, d, J=1), 8.62 (1H, s).

(Synthesis of Compound OE-T-3)

Under a nitrogen stream, compound OE-T-2 (0.26 g, 0.42 mmol) was azeotropically dried with acetonitrile, and the resultant product was dissolved in acetonitrile (3 mL). 4,5-Dicyanoimidazole (0.062 g, 0.52 mmol) and 2-cyanoethyl-N,N,N',N'-tetraisopropylphosphordiamidite (0.20 mL, 0.61 mmol) were added to the solution in this order under ice cooling, and the resultant solution was stirred at room temperature for 5 hours. The reaction solution was cooled on ice, then the reaction was terminated with water, then the reaction solution was diluted with ethyl acetate, and the diluted solution was fractionated to obtain an organic layer. The organic layer thus obtained was washed with water and saturated saline in this order, and the washed solution was dried over anhydrous sodium sulfate and was then subjected to distillation under reduced pressure. A crude product thus produced was purified by silica gel column chromatography (hexane:ethyl acetate=1:1 to 1:2) to produce compound OE-T-3 (0.30 g, 77%) as a white foam-like solid substance.

$^{31}$P NMR ($CDCl_3$) δ 149.1, 150.5.

HRMS (MALDI): calcd for C43H52N5NaO9P [M+Na$^+$] 836.3395, found 836.3398.

Synthesis Example 7

A compound (1) wherein "Base" was a thymin-1-yl group, $A^1$ was a single bond, $R^1$ was DMTr, $R^2$ was —P(N(i-Pr)$_2$)($OC_2H_4CN$), $R^3$ was a 3-(N,N-dimethylamino)propyl group, $R^4$ was an ethyl group in the R-configuration, and $R^5$ was a hydrogen atom (hereinafter, also referred to as "compound (R)EDM-T-2") was synthesized in accordance with the reaction scheme shown below.

[Formula 53]

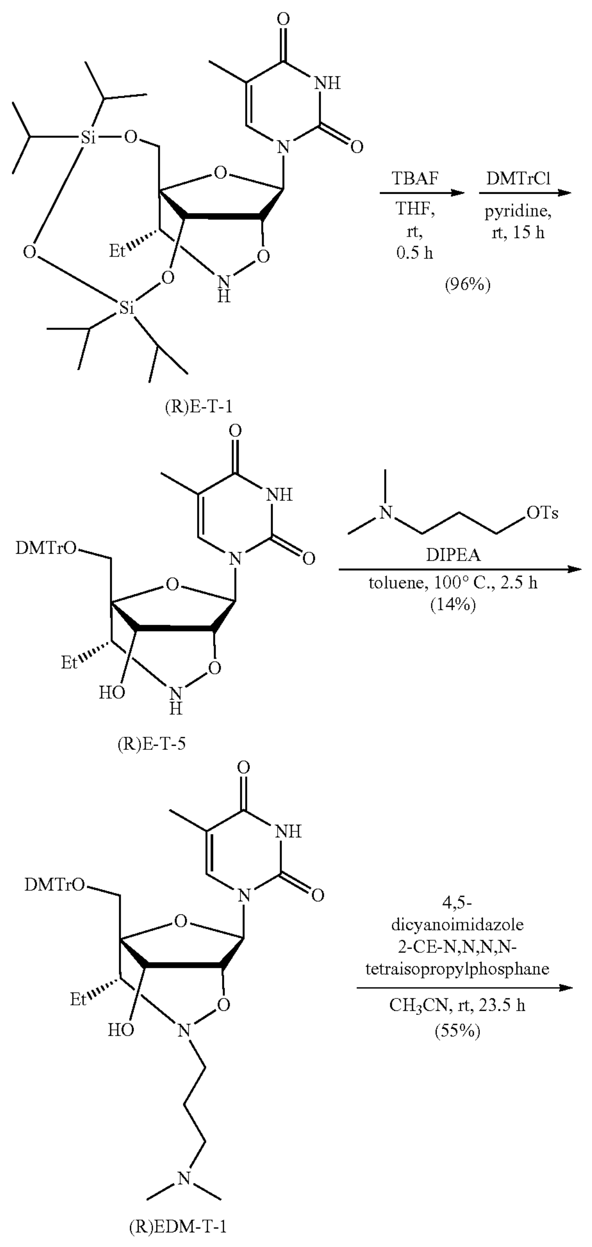

(R)E-T-1

(R)E-T-5

(R)EDM-T-1

-continued

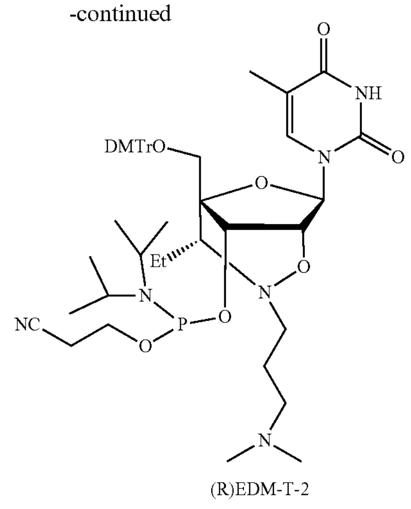

(R)EDM-T-2

(Synthesis of Compound (R)E-T-5)

Under a nitrogen stream, compound (R)M-T-1 (2.46 g, 4.42 mmol) was dissolved in tetrahydrofuran (30 mL), then tetra-n-butylammonium fluoride (a 1M solution in tetrahydrofuran, 11.0 mL, 11.0 mmol) was added to the solution, and the resultant solution was stirred at room temperature for 30 minutes. The reaction solution thus produced was subjected to distillation under reduced pressure, and a reaction residue was removed by silica gel column chromatography (ethyl acetate:methanol=10:1 to 8:1) to produce an intermediate. The intermediate was azeotropically dried with pyridine. Subsequently, under a nitrogen stream, the resultant produce was dissolved in pyridine (30 mL). 4,4'-Dimethoxytrityl chloride (2.59 g, 7.64 mmol) was added to the solution, and the resultant solution was stirred at room temperature for 15 hours. The reaction was terminated with methanol, and the reaction solution was diluted with water and ethyl acetate, and the diluted solution was fractionated into an organic layer and an aqueous layer. The aqueous layer was subjected to back-extraction with ethyl acetate. The organic layer obtained in the first fractionation was combined with the organic layer obtained in the back-extraction, the resultant solution was washed with saturated saline, and then the washed solution was dried over anhydrous sodium sulfate and was then distilled under reduced pressure. A crude product thus produced was purified by silica gel column chromatography (hexane:ethyl acetate=1:4 to 0:1) to produce compound (R)E-T-5 (2.63 g, 96%) as a white foam-like solid substance.

$^1$H NMR ($CDCl_3$) δ 0.79 (3H, t, J=7), 1.09-1.19 (2H, m), 1.27 (3H, d, J=1), 3.05-3.07 (1H, m), 3.28, 3.43 (2H, ABq, J=11), 3.41-3.44 (1H, m), 3.79 (6H, d, J=1), 4.40 (1H, d, J=3), 4.68 (1H, m), 5.60 (1H, brs), 6.25 (1H, s), 6.84-6.87 (4H, m), 7.21-7.35 (7H, m), 7.42-7.45 (2H, m), 8.33 (1H, d, J=1), 8.82 (1H, s).

(Synthesis of Compound (R)EDM-T-1)

Under a nitrogen stream, 3-(dimethylamino)-1-propanol (0.68 mL, 5.80 mmol) was added dropwise slowly to a suspension of sodium hydride (60% in oil, 0.17 g, 4.14 mmol) in toluene (6.8 mL) under ice cooling, and the resultant solution was stirred for 20 minutes under ice cooling. Subsequently, p-toluenesulfonyl chloride (0.79 g, 4.14 mmol) was added to the solution in two divided portions, and the resultant solution was stirred at room temperature for 2 hours. The reaction was terminated with water, then the reaction solution was diluted with saturated saline and toluene, and the diluted solution was fractionated into an organic layer and an aqueous layer. The aqueous layer was subjected to back-extraction with toluene. An organic layer obtained in the first fractionation was combined with an organic layer obtained in the back extraction, the resultant solution was washed with saturated saline, and the washed solution was dried over anhydrous sodium sulfate and was then subjected to distillation under reduced pressure until the residue became cloudy slightly. The solution of 3-(dimethylamino)-1-propylin p-toluenesulfonate in toluene thus produced was used without any modification in the subsequent reaction.

Under a nitrogen stream, (R)E-T-5 (1.63 g, 2.65 mmol) was dissolved in toluene (14 mL), and then N,N-diisopropylethylamine (1.1 mL, 6.35 mmol) was added to the resultant solution under room temperature. The reaction solution was warmed to 100° C., then the above-prepared solution of 3-(dimethylamino)-1-propyl p-toluenesulfonate in toluene was added dropwise to the reaction solution over 20 minutes, and the resultant solution was further stirred for 2 hours while keeping the temperature at 100° C. The temperature of the reaction solution was returned to room temperature, and then the reaction solvent was distilled away under reduced pressure. A crude product thus produced was purified by silica gel column chromatography (ethyl acetate:triethylamine:methanol=20:1:0 to 20:1:1.5) to produce compound (R)EDM-T-1 (0.27 g, 14%) as a white foam-like solid substance.

$^1$H NMR ($CDCl_3$) δ 0.73 (3H, t, J=8), 1.01-1.13, 1.43-1.52 (2H, m), 1.28 (3H, s), 1.65-1.74, 1.83-1.92 (2H, m), 2.21 (6H, s), 2.27-2.36, 2.41-2.49 (2H, m), 2.73-2.80 (2H, m), 3.04-3.13 (1H, m), 3.27, 3.53 (2H, ABq, J=11), 3.80 (6H, s), 4.31 (1H, d, J=3), 4.50 (1H, d, J=3), 6.31 (1H, s), 6.83-6.87 (4H, m), 7.21-7.37 (7H, m), 7.44-7.47 (2H, m), 7.87 (1H, s).

(Synthesis of Compound (R)EDM-T-2)

Under a nitrogen stream, compound (R)EDM-T-1 (0.41 g, 0.59 mmol) was azeotropically dried with acetonitrile, and the resultant product was dissolved in acetonitrile (5 mL). 4,5-Dicyanoimidazole (0.078 g, 0.66 mmol) and 2-cyanoethyl-N,N,N',N'-tetraisopropylphosphordiamidite (0.24 mL, 0.72 mmol) were added to the solution in this order under ice cooling, and the resultant solution was stirred at room temperature for 6 hours. Subsequently, 4,5-dicyanoimidazole (0.039 g, 0.33 mmol) and 2-cyanoethyl-N,N,N',N'-tetraisopropylphosphordiamidite (0.12 mL, 0.36 mmol) were added to the solution under room temperature, then the solution was further stirred for 16 hours in the same conditions, then 4,5-dicyanoimidazole (0.039 g, 0.33 mmol) and 2-cyanoethyl-N,N,N',N'-tetraisopropylphosphordiamidite (0.12 mL, 0.36 mmol) were added to the solution under room temperature, and the resultant solution was stirred for 1.5 hours under the same conditions. The reaction was terminated with water, then the reaction solution was diluted with ethyl acetate and saturated saline, and the diluted solution was fractionated to obtain an organic layer. The organic layer thus obtained was washed with water and saturated saline in this order, and the washed solution was dried over anhydrous sodium sulfate and was then subjected to distillation under reduced pressure. A crude product thus produced was purified by silica gel column chromatography (ethyl acetate:triethylamine:methanol=20:1:0 to 20:1:1) to produce compound (R)EDM-T-2 (0.30 g, 55%) as a white foam-like solid substance.

$^{31}$P NMR ($CDCl_3$) δ 148.9, 149.1.

HRMS (MALDI): calcd for C48H65N6NaO9P [M+Na$^+$] 923.4443, found 923.4420.

Oligonucleotide Synthesis Examples

Oligonucleotides were synthesized in accordance with a standard phosphoramidite protocol using the compounds ((R)M-T-4, (R)E-T-4, (S)M-T-4, OM-T-3, OE-T-3 and (R)EDM-T-2) produced in the Synthesis Examples by using a nucleic acid automatic synthesizer (Expedite (registered tradename), manufactured by 8909/ABI). In this manner, the following oligonucleotides were produced.

An oligonucleotide having a unit represented by formula (6) wherein "Base" was a thymin-1-yl group, $A^1$ was a single bond, n was 1, $R^3$ was a methyl group, R was an ethyl group in the (R)-configuration, and $R^5$ was a hydrogen atom (hereinafter, also referred to as "(R)E-T").

An oligonucleotide having a unit represented by formula (6) wherein "Base" was a thymin-1-yl group, $A^1$ was a single bond, n was 1, $R^3$ was a methyl group, $R^4$ was a methyl group in the (R)-configuration, and $R^5$ was a hydrogen atom (hereinafter, also referred to as "(R)M-T").

An oligonucleotide having a unit represented by formula (6) wherein "Base" was a thymin-1-yl group, $A^1$ was a single bond, n was 0, and $R^4$ was an ethyl group (hereinafter, also referred to as "OE-T").

An oligonucleotide having a unit represented by formula (6) wherein "Base" was a thymin-1-yl group, $A^1$ was a single bond, n was 1, $R^3$ was a methyl group, $R^4$ was a methyl group in the (S)-configuration, and $R^5$ was a hydrogen atom (hereinafter, also referred to as "(S)M-T").

An oligonucleotide having a unit represented by formula (6) wherein "Base" was a thymin-1-yl group, $A^1$ was a single bond, n was 0, and $R^4$ was a methyl group (hereinafter, also referred to as "OM-T").

An oligonucleotide having a unit represented by formula (6) wherein "Base" was a thymin-1-yl group, $A^1$ was a single bond, n was 1, $R^3$ was a 3-(N,N-dimethylamino)propyl group, $R^4$ was an ethyl group in the (R)-configuration, and $R^5$ was a hydrogen atom (hereinafter, also referred to as "(R)EDM-T").

Each of the oligonucleotides of which the 5'-terminal was protected by a dimethoxytrityl group and which was supported on a solid phase was subjected to the cleavage from a column with a 28% aqueous ammonia solution (for 1.5 hours), and then a cleaved oligonucleotide was reacted in a 28% aqueous ammonia solution for 16 hours at 60° C. to deprotect all of the protecting groups.

The oligonucleotide was subjected to a simple purification using an NAP-10 column, and was then purified by reversed-phase HPLC [WakoPak (registered tradename) WS-DNA column, 10.0 mm×250 mm)][conditions: a gradient of8 to 16% of acetonitrile in a 0.1M triethylammonium acetate buffer (pH 7.0) at 3 ml/min. for 30 minutes, column temperature of 50° C.].

The purities of the synthesized oligonucleotides were confirmed by reversed-phase HPLC [WakoPak (registered tradename) WS-DNA column, 4.6 mm×250 mm)][conditions: a gradient of 8 to 16% of acetonitrile in a 0.1M triethylammonium acetate buffer (pH7.0) at 1 ml/min. for 30 minutes, column temperature of 50° C., detection wavelength of 254 nm]. Each of the synthesized oligonucleotides had purity of 90% or more.

The molecular weights of the synthesized oligonucleotides were determined by a MALDI-TOF-MASS measurement. The calculated values and the found values (measurement results) of the molecular weights are shown in the table below. The unit represented by formula (6) was incorporated at a position indicated by n in each of the antisense strands (SEQ ID NOs:1 to 5) shown in the table below, in which "Base" was a thymin-1-yl group. Each of the nucleotide sequences excluding n was composed of DNA (formula (7) wherein $R^a$=H). As references, the calculated values and the found values of the molecular weights of oligonucleotides in each of which a unit represented by formula (9) wherein "Base" was a thymin-1-yl group and $R^b$ was Me or H was incorporated at a position indicated by n (in which the oligonucleotides are referred to as "NMe-T" and "NH-T", respectively, in the table) are also shown in the table. [Table 1)

TABLE 1

| MALDI-TOF-MASS | Calculated value $[M-H]^-$/found value $[M-H]^-$ n | | | |
|---|---|---|---|---|
| Antisense strand | NMe-T | NH-T | (R)E-T | (R)M-T |
| 5'-d(gcgtt**n**tttgct)-3' (SEQ ID NO: 1) | 3689.47/3687.54 | — | 3717.52/3719.68 | 3703.49/3703.27 |
| 5'-d(gcg**n**t**n**t**n**tgct)-3' (SEQ ID NO: 2) | 3803.57/3804.88 | 3761.48/3760.11 | 3887.72/3888.76 | 3845.63/3846.36 |
| 5'-d(gcgtt**nnn**tgct)-3' (SEQ ID NO: 3) | 3803.57/3804.80 | — | 3887.72/3887.40 | 3845.63/3845.07 |
| 5'-d(gcg**nnnnnn**gct)-3' (SEQ ID NO: 4) | 3974.72/3973.40 | 3890.54/3889.73 | 4143.02/4144.80 | 4058.84/4057.90 |
| 5'-d(tttttttt**n**t)-3' (SEQ ID NO: 5) | 3036.08/3037.95 | 3022.05/3023.73 | 3064.13/3062.88 | 3050.10/3050.91 |
| Antisense strand | OE-T | (S)M-T | OM-T | (R)EDM-T |
| 5'-d(gcgtt**n**tttgct)-3' (SEQ ID NO: 1) | 3701.48/3702.45 | 3703.49/3701.38 | 3687.45/3687.87 | 3788.64/3790.38 |
| 5'-d(gcg**n**t**n**t**n**tgct)-3' (SEQ ID NO: 2) | 3839.60/3840.68 | 3845.63/3845.28 | 3797.51/3797.22 | 4101.08/4102.38 |
| 5'-d(gcgtt**nnn**tgct)-3' (SEQ ID NO: 3) | 3839.60/3840.47 | 3845.63/3845.41 | 3797.51/3799.50 | 4101.08/4101.90 |
| 5'-d(gcg**nnnnnn**gct)-3' (SEQ ID NO: 4) | 4046.78/4047.76 | 4058.84/4056.62 | 3962.60/3962.77 | 4569.74/4570.75 |
| 5'-d(tttttttt**n**t)-3' (SEQ ID NO: 5) | 3048.09/3049.61 | 3050.10/3049.97 | 3034.06/3032.36 | 3135.25/3135.30 |

Test Examples

[Test Example 1] Measurement of Melting Temperatures (Tm) of Oligonucleotides (Evaluation of Double Strand Forming Capability)

The double strand forming capability of antisense strands was examined by measuring a melting temperature (Tm) between: each of six oligonucleotides (6) (i.e., (R)E-T, OE-T, (R)M-T, (S)M-T, OM-T, (R)EDM-T) (antisense strands) according to the present invention which were respectively synthesized by incorporating the compounds ((R)E-T-4, OE-T-3, (R)M-T-4, (S)M-T-4, OM-T-3, (R)EDM-T-2) produced in the above-mentioned Synthesis Examples at a position indicated by n in the sequence represented by SEQ ID NO: 4; and single-stranded DNA (5'-d(agcaaaaaacgc)-3'; SEQ ID NO: 6) (a sense strand) or single-stranded RNA (5'-r(agcaaaaaacgc)-3'; SEQ ID NO: 7) (a sense strand). As references, an oligonucleotide (DNA-T) which was synthesized in such a manner that a unit (T) represented by formula (7) wherein "Base" was a thymin-1-yl group and $R^a$ was H was positioned at a position indicated by n in SEQ ID NO: 4 and an oligonucleotide (NMe-T) which was synthesized by incorporating a unit represented by formula (9) wherein "Base" was a thymin-1-yl group and $R^b$ was Me at a position indicated by n in SEQ ID NO: 4 were prepared as antisense strands.

A sample solution (120 μl) in which the final concentrations of sodium chloride, a sodium phosphate buffer solution (pH 7.2), each of the antisense strands and each of the sense strands were adjusted to 100 mM, 10 mM, 4 μM and 4 μM, respectively, was prepared, then the sample solution was warmed from 15° C. to 110° C. at a rate of 0.5° C./min., and an absorbance at 260 nm was measured at 0.5-° C. intervals using a spectrophotometer (UV-1800, manufactured by Shimadzu Corporation). A Tm value was calculated from the obtained measurement value by a differentiation method. The results are shown in the table below.

Capability of Forming Double Strand with Single-Stranded DNA (Tm Value)

TABLE 2

| Tm value (target: ssDNA) | Oligonucleotide (antisense strand) 5'-d(gcgnnnnnngct)-3' (SEQ ID NO: 4) | | | | | | | |
|---|---|---|---|---|---|---|---|---|
| n = | DNA-T | NMe-T | (R)E-T | OE-T | (R)M-T | (S)M-T | OM-T | (R)EDM-T |
| Target sequence (sense strand) 5'-d(agcaaaaaacgc)-3' (SEQ ID NO: 6) | 52° C. | 63° C. | 65° C. | 64° C. | 66° C. | 62° C. | 65° C. | 77° C. |

Capability of Forming Double Strand with Single-Stranded RNA (Tm Value)

TABLE 3

| Tm value (target: ssRNA) | Oligonucleotide (antisense strand) 5'-d(gcgnnnnnngct)-3' (SEQ ID NO: 4) | | | | | | | |
|---|---|---|---|---|---|---|---|---|
| n = | DNA-T | NMe-T | (R)E-T | OE-T | (R)M-T | (S)M-T | OM-T | (R)EDM-T |
| Target sequence (sense strand) 5'-r(agcaaaaaacgc)-3' (SEQ ID NO: 7) | 48° C. | 80° C. | 86° C. | 79° C. | 87° C. | 80° C. | 79° C. | 89° C. |

It was demonstrated that each of the oligonucleotides (6) according to the present invention had excellent capability of forming a double strand together with each of single-stranded DNA and single-stranded RNA, particularly single-stranded RNA. Accordingly, the oligonucleotides (6) according to the present invention are suitable for use in DNA- and RNA-targeting nucleic acid therapeutics and genetic diagnosis for which excellent double strand formation capability is required.

[Test Example 2] Measurement of Enzyme Resistance Capability of Oligonucleotides (1) Preparation of Oligonucleotides for Use in Measurement of Enzyme Resistance Capability Oligonucleotides shown in the table below were prepared in the same manner as in the above-mentioned Synthesis Examples of the oligonucleotides, each of which had a sequence represented by SEQ ID NO: 5 having such a structure that the sequence represented by SEQ ID NO: 8 (TTTTTTTTTT) or a portion thereof was modified.

TABLE 4

| No. | Name of oligonucleotide | Sequence (5'→3') | Length (mer) |
|---|---|---|---|
| 1 | DNA oligonucleotide | TTTTTTTTTT | 10 |
| 2 | S oligonucleotide | TTTTTTTTTT | 10 |
| 3 | NH-T oligonucleotide | TTTTTTTT$t^{\alpha}$T | 10 |
| 4 | NMe-T oligonucleotide | TTTTTTTT$t^{\beta}$T | 10 |
| 5 | LNA-T oligonucleotide | TTTTTTTTtT | 10 |
| 6 | (R)M-T oligonucleotide | TTTTTTTT$\underline{t}^{a}$T | 10 |
| 7 | (R)E-T oligonucleotide | TTTTTTTT$\underline{t}^{b}$T | 10 |
| 8 | (S)M-T oligonucleotide | TTTTTTTT$\underline{t}^{c}$T | 10 |
| 9 | OM-T oligonucleotide | TTTTTTTT$\underline{t}^{d}$T | 10 |
| 10 | (R)EDM-T oligonucleotide | TTTTTTTT$\underline{t}^{e}$T | 10 |

T = a unit represented by formula (7) wherein "Base" is a thymin-1-yl group and $R^a$ is H = a phosophorothioate bond $T^{\alpha}$ = a unit represented by formula (9) wherein "Base" is a thymin-1-yl group and $R^b$ is H $t^{\beta}$ = a unit represented by formula (9) wherein "Base" is a thymin-1-yl group and $R^b$ is Me t = a unit represented by formula (8) wherein "Base" is a thymin-1-yl group $\underline{t}^a$ = a unit represented by formula (6) wherein "Base" is a thymin-1-yl group, $A^1$ is a single bond, n is 1, $R^3$ is a methyl group, $R^4$ is a methyl group in the (R)-configuration, and $R^5$ is a hydrogen atom TABLE 4-continued

| No. | Name of oligonucleotide | Sequence (5'→3') | Length (mer) |
|---|---|---|---|

$\underline{t}^b$ = a unit represented by formula (6) wherein "Base" is a thymin-1-yl group, $A^1$ is a single bond, n is 1, $R^3$ is a methyl group, $R^4$ is an ethyl group in the (R)-configuration, and $R^5$ is a hydrogen atom $\underline{t}^c$ = a unit represented by formula (6) wherein "Base" is a thymin-1-yl group, $A^1$ is a single bond, n is 1, $R^3$ is a methyl group, $R^4$ is a methyl group in the (S)-configuration, and $R^5$ is a hydrogen atom.

$\underline{t}^d$ = a unit represented by formula (6) wherein "Base" is a thymin-1-yl group, $A^1$ is a single bond, n is 0, and $R^4$ is a methyl group $\underline{t}^e$ = a unit represented by formula (6) wherein "Base" is a thymin-1-yl group, $A^1$ is a single bond, n is 1, $R^3$ is a 3-(N,N-dimethylamino)propyl group, $R^4$ is an ethyl group in the (R)-configuration, and $R^5$ is a hydrogen atom (2) Preparation of Sample Solutions Sample solutions shown in the table below were prepared.

TABLE 5

| Reagent | Final concentration |
|---|---|
| Tris HCl pH 8.0 | 50 mM |
| $MgCl_2$ | 10 mM |
| Oligonucleotide | 7.5 μM |

(3) Enzymatic Reactions

The oligonucleotides Nos. 1 to 7 were subjected to procedure A ((1) to (4) mentioned below) at a temperature of 37° C. using a device (MD-MINI, manufactured by Major Science).

(1) The sample solution was incubated (for 5 minutes).

(2) An enzyme CAVP (*Crotalus adamanteus* Venom phosphodiesterase I) was added at a final concentration of 1.60 μg/mL or 5.00 μg/mL to initiate a reaction.

(3) EDTA was added in such a manner that the concentration of EDTA became 5.0 mM in a reaction solution at the time point of the completion of the reaction to terminate the reaction.

(4) The reaction times were 0 minute, 5 minutes, 10 minutes, 40 minutes and 80 minutes.

The oligonucleotides Nos. 1, 2, 4, 6 and 8 to 10 were subjected to procedure B in which the process was carried out in the same manner as in procedure A except that the enzyme CAVP was added at a final concentration of 4.38 μg/mL in (2).

(4) Evaluation of Enzyme Resistance Capability

Each of the sample solutions in each of which the enzymatic reaction in accordance with procedure A had been completed was subjected to a HPLC analysis under the following conditions.

(Conditions)

Device: LC-2010A HT (manufactured by Shimadzu Corporation)

Column: XBridge Oligonucleoties BEH $C_{18}$ column 130 Å, 2.5 μm, 4.6 mm×50 mm mobile phase Solution A: a 0.1M triethylammonium acetate buffer (pH 7.0)

Solution B: a 0.1M triethylammonium acetate buffer (pH 7.0):acetonitrile=1:1 (v/v) gradient: 5 to 30% ((v/v) solution B), 15 minutes)

Flow rate: 0.8 mL/min.

Column temperature: 50° C.

Detection wavelength: 268 nm

Injection amount: 15 μL (101.2 pmol)

The amount of each of the oligonucleotides which was undigested with the enzyme was measured from a HPLC analysis result, and a residual ratio of the undigested oligonucleotide at each of the reaction times was calculated in accordance with the following formula.

[Mathematical formula 1]

$$\text{Residual ratio (\%) of undigested oligonucleotide at each reaction time} = \frac{\text{area of undigested oligonucleotide at each rection time}}{\text{area of undigested oligonucleotide at rection time of 0 min}} \times 100$$

The sample solutions in which the enzymatic reaction in procedure B had been completed were subjected to an HPLC analysis in the same manner as mentioned above, except that Alliance e2695 (manufactured by Waters) was used as the device.

5) Results

Figure 1B:
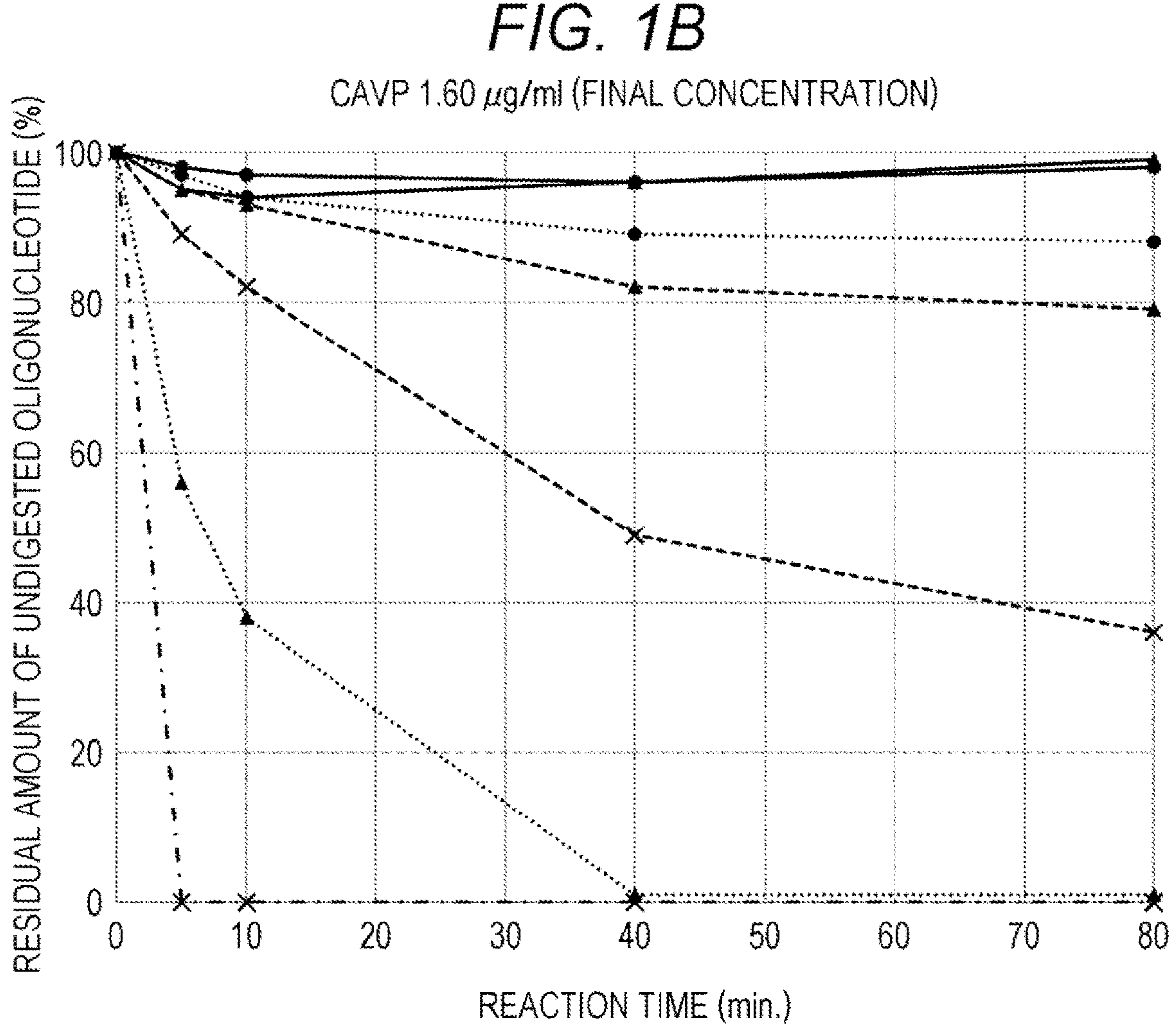
FIG. 1B shows graphs illustrating the relationship between the reaction time of a digestive enzyme at a final concentration of 1.6011 g/mL and the residual ratio of an undigested oligonucleotide.
Figure 1C:
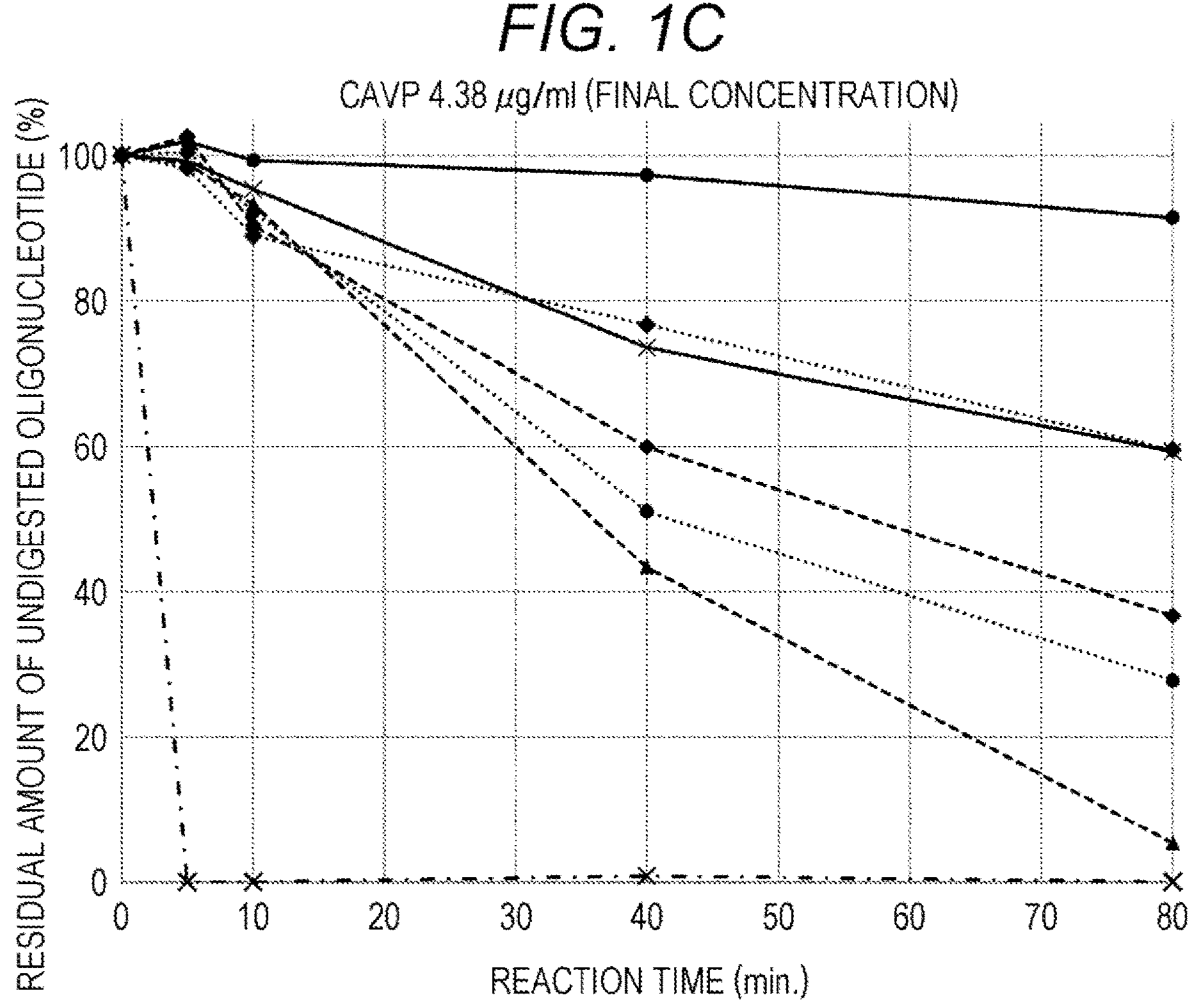
FIG. 1C shows graphs illustrating the relationship between the reaction time of a digestive enzyme at a final concentration of 4.3811 g/mL and the residual ratio of an undigested oligonucleotide.

The results obtained in the case where the final concentration of the enzyme CAVP was 5.00 μg/mL, the case where the final concentration of the enzyme CAVP was 1.60 μg/mL and the case where the final concentration of the enzyme CAVP was 4.38 μg/mL are shown in Table 6A and FIG. 1A, Table 6B and FIG. 1B, and Table 6C and FIG. 1C, respectively.

TABLE 6A

Residual ratio (%) of undigested oligonucleotide at each rection time: CAVP 5.00 μg/ml (final concentration)

| | | Reaction time | | | | |
|---|---|---|---|---|---|---|
| No. | Name of oligonucleotide | 0 min. | 5 min. | 10 min. | 40 min. | 80 min. |
| 1 | DNA oligonucleotide | 100 | 0 | 0 | 0 | 0 |
| 2 | S oligonucleotide | 100 | 81 | 74 | 40 | 26 |
| 3 | NH-T oligonucleotide | 100 | 42 | 31 | 1 | 0 |
| 4 | NMe-T oligonucleotide | 100 | 89 | 75 | 17 | 5 |
| 5 | LNA-T oligonucleotide | 100 | 0 | 0 | 0 | 0 |
| 6 | (R)M-T oligonucleotide | 100 | 95 | 93 | 87 | 87 |
| 7 | (R)E-T oligonucleotide | 100 | 90 | 87 | 79 | 79 |

TABLE 6B

Residual ratio (%) of undigested oligonucleotide at each rection time: CAVP 1.60 μg/ml (final concentration)

| | | Reaction time | | | | |
|---|---|---|---|---|---|---|
| No. | Name of oligonucleotide | 0 min. | 5 min. | 10 min. | 40 min. | 80 min. |
| 1 | DNA oligonucleotide | 100 | 0 | 0 | 0 | 0 |
| 2 | S oligonucleotide | 100 | 97 | 94 | 89 | 88 |
| 3 | NH-T oligonucleotide | 100 | 89 | 82 | 49 | 36 |
| 4 | NMe-T oligonucleotide | 100 | 95 | 93 | 82 | 79 |
| 5 | LNA-T oligonucleotide | 100 | 56 | 38 | 1 | 1 |
| 6 | (R)M-T oligonucleotide | 100 | 98 | 97 | 96 | 98 |
| 7 | (R)E-T oligonucleotide | 100 | 95 | 94 | 96 | 99 |

TABLE 6C

Residual ratio (%) of undigested oligonucleotide at each rection time: CAVP 4.38 μg/ml (final concentration)

| | | Reaction time | | | | |
|---|---|---|---|---|---|---|
| No. | Name of oligonucleotide | 0 min. | 5 min. | 10 min. | 40 min. | 80 min. |
| 1 | DNA oligonucleotide | 100 | 0 | 0 | 1 | 0 |
| 2 | S oligonucleotide | 100 | 101 | 92 | 51 | 28 |
| 4 | NMe-T oligonucleotide | 100 | 99 | 93 | 43 | 5 |
| 6 | (R)M-T oligonucleotide | 100 | 102 | 99 | 97 | 91 |
| 8 | (S)M-T oligonucleotide | 100 | 103 | 90 | 60 | 37 |
| 9 | OM-T oligonucleotide | 100 | 98 | 89 | 77 | 60 |
| 10 | (R)EDM-T oligonucleotide | 100 | 99 | 95 | 74 | 59 |

As apparent from the results, the oligonucleotides (6) according to the present invention had superior enzyme resistance compared with the naturally occurring types of these oligonucleotides and other non-naturally-occurring oligonucleotides.

What is claimed is:

1. A compound represented by formula (1) or a salt thereof:

(1)

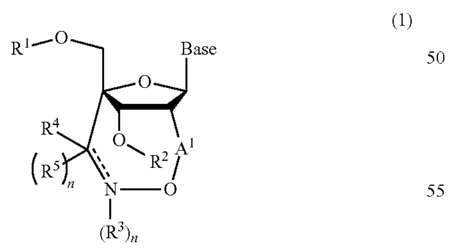

wherein:

"Base" represents an aromatic heterocyclic group which may have a substituent, or an aromatic hydrocarbon ring group which may have a substituent;

$A^1$ represents a single bond or an alkylene group;

$R^1$ and $R^2$ are the same as or different from each other and independently represent a hydrogen atom, an alkyl group which may have a substituent, an alkenyl group which may have a substituent, a cycloalkyl group which may have a substituent, a cycloalkenyl group which may have a substituent, an aryl group which may have a substituent, a protecting group for a hydroxyl group, a phosphino group which has a substituent, a dihydroxyphosphinyl group which may have a substituent, or a hydroxymercaptophosphinyl group which may have a substituent, or $R^1$, $R^2$, two oxygen atoms respectively adjacent to $R^1$ and $R^2$ and carbon atoms at position-3 to position-5 in a furanose together form a ring which may have a substituent;

$R^3$ represents a hydrogen atom, an alkyl group which may have a substituent, an alkenyl group which may have a substituent, a cycloalkyl group which may have a substituent, an aryl group which may have a substituent, an acyl group which may have a substituent, a sulfonyl group which has a substituent, a silyl group which has a substituent, a functional molecule unit substituent, or a group represented by the formula: $R^{31}$—X— wherein $R^{31}$ represents an amino group which may have a substituent; and X represents an alkylene group which may have a substituent, or a group having such a structure that at least one methylene group moiety in the alkylene group is substituted by —$N(R^{32})$— wherein $R^{32}$ represents a hydrogen atom or an alkyl group, —O— or —$S(=O)_k$— wherein k represents 0, 1 or 2;

$R^4$ represents a hydrogen atom, an alkyl group which may have a substituent, or an aryl group which may have a substituent;

$R^5$ represents a hydrogen atom, an alkyl group which may have a substituent, or an aryl group which may have a substituent;

$R^4$ and $R^5$ do not represent hydrogen atoms coincidentally;

a symbol represented by the following formula: represents a single bond or a double bond;

when the symbol represents a single bond, n represents 1; and when the symbol represents a double bond, n represents 0.

2. The compound or the salt thereof according to claim 1, wherein A represents a single bond.

3. The compound or the salt thereof according to claim 1, wherein the symbol represented by the following formula:

represents a single bond and n represents 1.

4. The compound or the salt thereof according to claim 1, wherein $R^4$ represents an alkyl group.

5. The compound or the salt thereof according to claim 1, wherein $R^5$ represents a hydrogen atom or an alkyl group.

6. The compound or the salt thereof according to claim 1, wherein $R^3$ represents a hydrogen atom, an alkyl group, an alkenyl group, a cycloalkyl group, an aryl group, an aralkyl group, an acyl group, an alkylsulfonyl group, an arylsulfonyl group, a group represented by the formula: —$Si(R^6)_3$ wherein $R^6$'s are the same as or different from each other and independently represent an alkyl group or an aryl group, a labeling functional group, a residue of an intercalator, a group having capability of binding to a nucleic acid, said group being a residue of a nucleic acid binding agent selected from the group consisting of netropsin, distamine and (pyrrole imidazole)polyamide, a functional group having a cleavage activity, a group having cellular or nuclear translocation capability, said group being a residue of a cellular or nuclear translocation signal peptide selected from the group consisting of twin-arginine translocation signal peptide, polyarginine, GalNac (N-acetylgalactosamine) and a signal peptide derived from SV40T antigen, or a group having metal chelating capability.

7. The compound or the salt thereof according to claim 1, wherein:

$R^3$ represents a group represented by the formula: $R^{31}$—X—;

$R^{31}$ represents a group represented by formula (A):

(A)

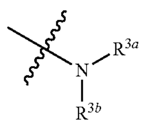

wherein:

$R^{3a}$ and $R^{3b}$ are the same as or different from each other and independently represent a hydrogen atom, an alkyl group which may have a substituent, an alkenyl group which may have a substituent, a cycloalkyl group which may have a substituent, a cycloalkenyl group which may have a substituent, an aryl group which may have a substituent, or a protecting group for an amino group, or $R^{3a}$, $R^{3b}$ and a nitrogen atom adjacent to $R^{3a}$ and $R^{3b}$ together form a ring which may have a substituent, or a group represented by formula (B):

(B)

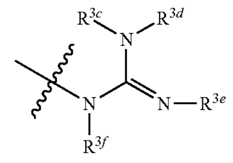

wherein $R^{3c}$ to $R^{3f}$ are the same as or different from each other and independently represent a hydrogen atom, an alkyl group, or a protecting group for an amino group; and X represents —$C_mH_{2m}$— wherein m represents an integer of 1 to 10.

8. The compound or the salt thereof according to claim 1, wherein:

$R^1$ and $R^2$ are the same as or different from each other and independently represent a hydrogen atom, an alkyl group which may have a substituent, an aryl group which may have a substituent, an alkylcarbonyl group, an arylcarbonyl group, an alkylsulfonyl group, an arylsulfonyl group, a group represented by the formula: —$Si(R^6)_3$ wherein $R^6$'s are the same as or different from each other and independently represent an alkyl group or an aryl group, a group represented by the formula: —$P(R^7)(R^8)$ wherein $R^7$ and $R^8$ are the same as or different from each other and independently represent a hydroxyl group, a mercapto group, an amino group, an alkoxy group, a haloalkoxy group, a cyanoalkoxy group, an alkylthio group, a haloalkylthio group, a cyanoalkylthio group, or an alkylamino group, a dihydroxyphosphinyl group, or a hydroxymercaptophosphinyl group; or $R^1$, $R^2$, two oxygen atoms respectively adjacent to $R^1$ and $R^2$ and carbon atoms at position-3 to position-5 in a furanose together form a ring which may have a substituent.

9. The compound or the salt thereof according to claim 1, wherein "Base" represents a 2,4-dioxo-1,2,3,4-tetrahydropyrimidin-1-yl group which may have a substituent, a 2-oxo-1,2-dihydropyrimidin-1-yl group which may have a substituent, a purin-9-yl group which may have a substituent, or a 6-oxo-1,6-dihydro-9H-purin-9-yl group which may have a substituent.

10. The compound or the salt thereof according to claim 1, wherein the compound or the salt thereof is a compound represented by formula (1A):

(1A)

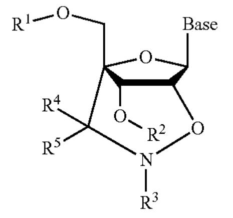

wherein "Base" and $R^1$ to $R^5$ are as defined above or a salt thereof.

11. The compound or the salt thereof according to claim 1, wherein the compound or the salt thereof is a compound represented by formula (1B):

(1B)

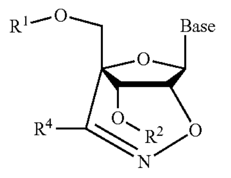

wherein "Base", $R^1$, $R^2$, and $R^4$ are as defined above or a salt thereof.

12. A method for producing the compound or the salt thereof according to claim 1, wherein n represents 0 or n represents 1 and $R^5$ represents a hydrogen atom, the method comprising:

(I) a step of reacting a compound represented by formula (1E):

(1E)

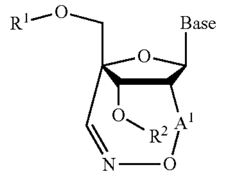

wherein "Base", $A^1$, $R^1$ and $R^2$ are as defined in claim 1 with radical represented by the formula: $R^4$ wherein $R^4$ is as defined in claim 1 or an organometallic reagent represented by the formula: $R^4M$ wherein M represents a metal atom or an atomic group comprising a metal atom; and $R^4$ is as defined in claim 1, in which the method may further comprise:

(II) a step of dehydrogenating a compound produced in the step (I);

(III) a step of dehydrogenating and then hydrogenating the compound produced in the step (I); or (IV) a step of reacting the compound produced in the step (I) or a compound produced by dehydrogenating and then hydrogenating the compound produced in the step (I) with a compound represented by the formula: $R^3$-L wherein L represents a leaving group; and $R^3$ is as defined in claim 1 but does not represent a hydrogen atom.

13. A method for producing the compound or the salt thereof according to claim 1, wherein n represents 1, $R^3$ represents a methyl group which may have one or two substituents and $R^5$ represents a hydrogen atom, the method comprising:

(I) a step of reacting a compound represented by formula (1E):

(1E)

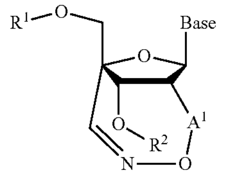

wherein "Base", $A^1$, $R^1$, and $R^2$ are as defined in claim 1 with radical represented by the formula: $R^4$ wherein $R^4$ is as defined in claim 1 or an organometallic reagent represented by the formula: $R^4M$ wherein M represents a metal atom or an atomic group comprising a metal atom; and $R^4$ is as defined in claim 1; and (II) a step of reacting the compound produced in the step (I) or a compound produced by dehydrogenating and then hydrogenating the compound produced in the step (I) with a carbonyl compound.

14. An oligonucleotide or a salt thereof, the oligonucleotide comprising a unit represented by formula (6):

(6)

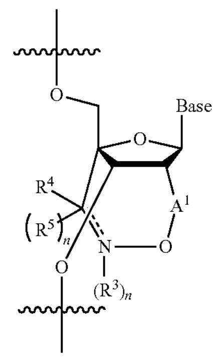

wherein:

"Base" represents an aromatic heterocyclic group which may have a substituent, or an aromatic hydrocarbon ring group which may have a substituent;

$A^1$ represents a single bond or an alkylene group;

$R^3$ represents a hydrogen atom, an alkyl group which may have a substituent, an alkenyl group which may have a substituent, a cycloalkyl group which may have a substituent, an aryl group which may have a substituent, an acyl group which may have a substituent, a sulfonyl group which has a substituent, a silyl group which has a substituent, a functional molecule unit substituent, or a group represented by the formula: $R^{31}$—X— wherein $R^{31}$ represents an amino group which may have a substituent; and X represents an alkylene group which may have a substituent, or a group having such a structure that at least one methylene group moiety in the alkylene group is substituted by —$N(R^{32})$— wherein $R^{32}$ represents a hydrogen atom or an alkyl group, —O— or —$S(=O)_k$— wherein k represents 0, 1 or 2;

$R^4$ represents a hydrogen atom, an alkyl group which may have a substituent, or an aryl group which may have a substituent;

$R^5$ represents a hydrogen atom, an alkyl group which may have a substituent, or an aryl group which may have a substituent;

$R^4$ and $R^5$ do not represent hydrogen atoms coincidentally;

a symbol represented by the following formula: ⎓ represents a single bond or a double bond;

when the symbol represents a single bond, n represents 1; and when the symbol represents a double bond, n represents 0.

15. A method for detecting a target nucleic acid, the method comprising:

(I) a step of amplifying the target nucleic acid selectively by a nucleic acid amplification method; and (II) a step of detecting the target nucleic acid that has been amplified in the step (I), in which an oligonucleotide that is used for the amplification or the detection comprises the oligonucleotide or the salt thereof according to claim 14.

16. A kit for detecting or selectively amplifying a target nucleic acid, in which:

(a) the kit comprises a primer and/or a probe, in which at least one of the primer and the probe comprises the oligonucleotide or the salt thereof according to claim 14; or (b) the kit comprises a clamp nucleic acid and a primer, in which at least one of the clamp nucleic acid and the primer comprises the oligonucleotide or the salt thereof according to claim 14.

17. A pharmaceutical composition which comprises the compound or the salt thereof according to claim 1.

18. A pharmaceutical composition which comprises the oligonucleotide or the salt thereof according to claim 14.

19. The compound or the salt thereof according to claim 6, wherein the residue of an intercalator is selected from the group consisting of a group having an anthracene skeleton, a group having a pyrene skeleton, a group having an anthraquinone skeleton, a group having an acridine skeleton, a group having a naphthalimide skeleton, and a residue of tamoxifen.

* * * * *

SEQUENCE LISTING

```
Sequence total quantity: 8
SEQ ID NO: 1            moltype = DNA  length = 12
FEATURE                 Location/Qualifiers
misc_feature            1..12
                        note = Antisense Strand
misc_feature            6
                        note = n is modified t
source                  1..12
                        mol_type = other DNA
                        organism = synthetic construct
```

-continued

```
SEQUENCE: 1
gcgttntttg ct                                                        12

SEQ ID NO: 2            moltype =   length =
SEQUENCE: 2
000

SEQ ID NO: 3            moltype =   length =
SEQUENCE: 3
000

SEQ ID NO: 4            moltype =   length =
SEQUENCE: 4
000

SEQ ID NO: 5            moltype =   length =
SEQUENCE: 5
000

SEQ ID NO: 6            moltype = DNA  length = 12
FEATURE                 Location/Qualifiers
misc_feature            1..12
                        note = Sense Strand
source                  1..12
                        mol_type = other DNA
                        organism = synthetic construct
SEQUENCE: 6
agcaaaaaac gc                                                        12

SEQ ID NO: 7            moltype = RNA  length = 12
FEATURE                 Location/Qualifiers
misc_feature            1..12
                        note = Sense Strand
source                  1..12
                        mol_type = other RNA
                        organism = synthetic construct
SEQUENCE: 7
agcaaaaaac gc                                                        12

SEQ ID NO: 8            moltype = DNA  length = 10
FEATURE                 Location/Qualifiers
misc_feature            1..10
                        note = Oligonucleotide
source                  1..10
                        mol_type = other DNA
                        organism = synthetic construct
SEQUENCE: 8
tttttttttt                                                           10
```